United States Patent
Singamaneni et al.

(10) Patent No.: US 10,729,988 B2
(45) Date of Patent: Aug. 4, 2020

(54) BILAYERED STRUCTURES FOR SOLAR STEAM GENERATION

(71) Applicants: Srikanth Singamaneni, St. Louis, MO (US); Qisheng Jiang, St. Louis, MO (US); Limei Tian, St. Louis, MO (US)

(72) Inventors: Srikanth Singamaneni, St. Louis, MO (US); Qisheng Jiang, St. Louis, MO (US); Limei Tian, St. Louis, MO (US)

(73) Assignee: Washington University, St. Louis, MO (US)

( * ) Notice: Subject to any disclaimer, the term of this patent is extended or adjusted under 35 U.S.C. 154(b) by 170 days.

(21) Appl. No.: 15/653,942

(22) Filed: Jul. 19, 2017

(65) Prior Publication Data

US 2018/0043278 A1    Feb. 15, 2018

Related U.S. Application Data

(60) Provisional application No. 62/426,979, filed on Nov. 28, 2016, provisional application No. 62/369,934, filed on Aug. 2, 2016.

(51) Int. Cl.
| | |
|---|---|
| B32B 23/00 | (2006.01) |
| B01D 3/38 | (2006.01) |
| B01D 1/00 | (2006.01) |
| C12P 19/04 | (2006.01) |
| C02F 1/14 | (2006.01) |
| C02F 1/04 | (2006.01) |
| B01D 5/00 | (2006.01) |
| F24S 70/10 | (2018.01) |
| C02F 1/10 | (2006.01) |
| B32B 1/00 | (2006.01) |
| F24S 80/00 | (2018.01) |

(52) U.S. Cl.
CPC ............. *B01D 3/38* (2013.01); *B01D 1/0035* (2013.01); *B01D 5/006* (2013.01); *B32B 1/00* (2013.01); *B32B 23/00* (2013.01); *C02F 1/048* (2013.01); *C02F 1/10* (2013.01); *C02F 1/14* (2013.01); *C12P 19/04* (2013.01); *F24S 70/10* (2018.05); *F24S 2080/017* (2018.05); *Y02A 20/212* (2018.01); *Y02P 20/134* (2015.11); *Y02P 20/136* (2015.11); *Y02P 20/59* (2015.11); *Y02W 10/37* (2015.05)

(58) Field of Classification Search
CPC ...................................................... B32B 23/00
See application file for complete search history.

(56) References Cited

U.S. PATENT DOCUMENTS

| | | | |
|---|---|---|---|
| 2015/0072133 A1 | 3/2015 | Ghasemi et al. | |
| 2015/0141711 A1* | 5/2015 | Chu | C07C 29/76 |
| | | | 568/918 |
| 2016/0084532 A1 | 3/2016 | Tsutsui et al. | |
| 2016/0192501 A1 | 6/2016 | Yan et al. | |
| 2016/0199767 A1* | 7/2016 | Agrahari | B01D 39/18 |
| | | | 55/486 |
| 2016/0235347 A1* | 8/2016 | Baig | A61B 5/4076 |
| 2016/0319176 A1* | 11/2016 | Konagaya | B32B 9/04 |
| 2017/0142975 A1* | 5/2017 | Shi | A01N 59/16 |

FOREIGN PATENT DOCUMENTS

| | | |
|---|---|---|
| WO | 2013076372 A1 | 5/2013 |
| WO | 2016071573 A1 | 5/2016 |

OTHER PUBLICATIONS

Ouyang, Wenzhu et al, "Scalable preparation of three-dimensional porous structures of reduced graphene oxide/cellulose composites and their application in supercapacitors", Carbon 62 (Jun. 25, 2013), pp. 501-509 (Year: 2013).*
Alagarasi A., "Introduction to nanomaterials," in Nanomaterials, Viswanathan B. (ed.), Alpha Science/Narosa Publishing House, 2009, Chapter 1, pp. 1-76.
Classification of Nanomaterials, The Four Main Types of Intentionally Produced Nanomaterials, sponsored by U.S. Environmental Protection Agency, Mar. 1, 2007, http://www.azonano.com/article.aspx?ArticleID=1872, 4 pages.
Ghasemi et al, "Solar steam generation by heat localization", Nature Communications, Jul. 21, 2014, 7 pages.
Ghasemi et al, "Solar steam generation by heat localization", Nature Communications, Jul. 21, 2014, Supplemental Material, 20 pages.
Ito et al, "Multifunctional Porous Graphene for High-Efficiency Steam Generation by Heat Localization", Advanced Materials, 2015, vol. 27, pp. 4302-4307.
Ito et al, "Multifunctional Porous Graphene for High-Efficiency Steam Generation by Heat Localization", Advanced Materials, 2015, vol. 27, Supporting Information, pp. 1-7.
Jiang et al., "Bilayered Biofoam for Highly Efficient Solar Steam Generation", Advanced Materials, 2016, vol. 28, Issue 42, pp. 1-8.
Jiang et al., "Bilayered Biofoam for Highly Efficient Solar Steam Generation", Advanced Materials, 2016, vol. 28, Issue 42, Supporting Information, 8 pages.
Jozala et al, "Bacterial nanocellulose production and application: a 10-year overview", Appl Microbiol Biotechnol, Jan. 8, 2016, 11 pages.
Liu et al., A Bioinspired, Reusable, Paper-Based System for High-Performance Large-Scale Evaporation, Advanced Materials, 2015, vol. 27, pp. 2768-2774.
Liu et al., A Bioinspired, Reusable, Paper-Based System for High-Performance Large-Scale Evaporation, Advanced Materials, 2015, vol. 27, Supporting Information, pp. 1-13.
Ultrafiltration, Nanofiltration and Reverse Osmosis, www.safewater.org, Jan. 2017, Fact Sheet, pp. 1-6.

* cited by examiner

*Primary Examiner* — Renee Robinson
(74) *Attorney, Agent, or Firm* — Armstrong Teasdale LLP

(57) ABSTRACT

The present disclosure is directed to steam generation through the efficient harvesting of solar energy. In particular, the present disclosure is directed to bilayered structures that are cost-effective, scalable and/or biodegradable that provide high steam-generation efficiency.

11 Claims, 33 Drawing Sheets

RGO/BNC:BNC Hydrogel

RGO/BNC:BNC Aerogel

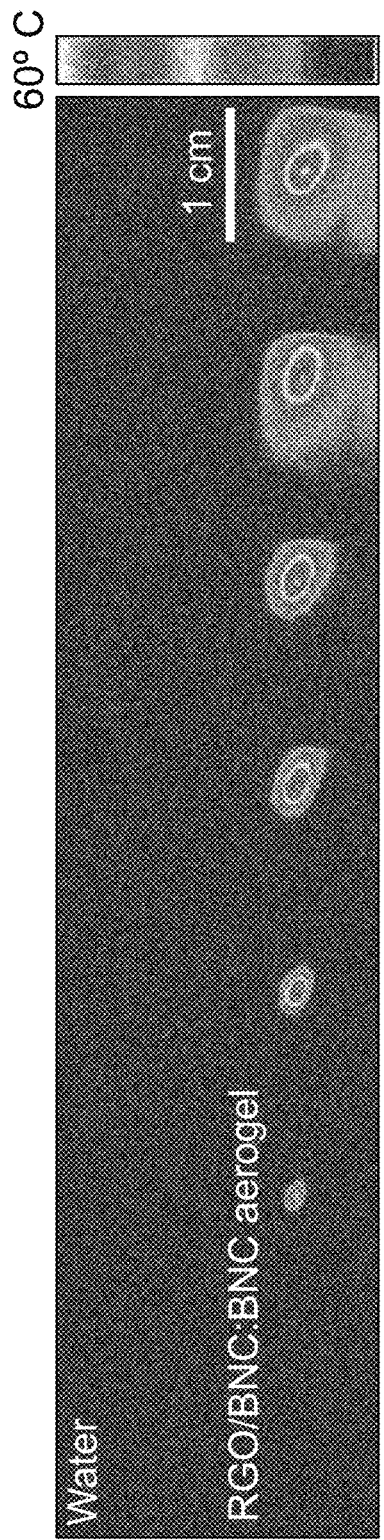
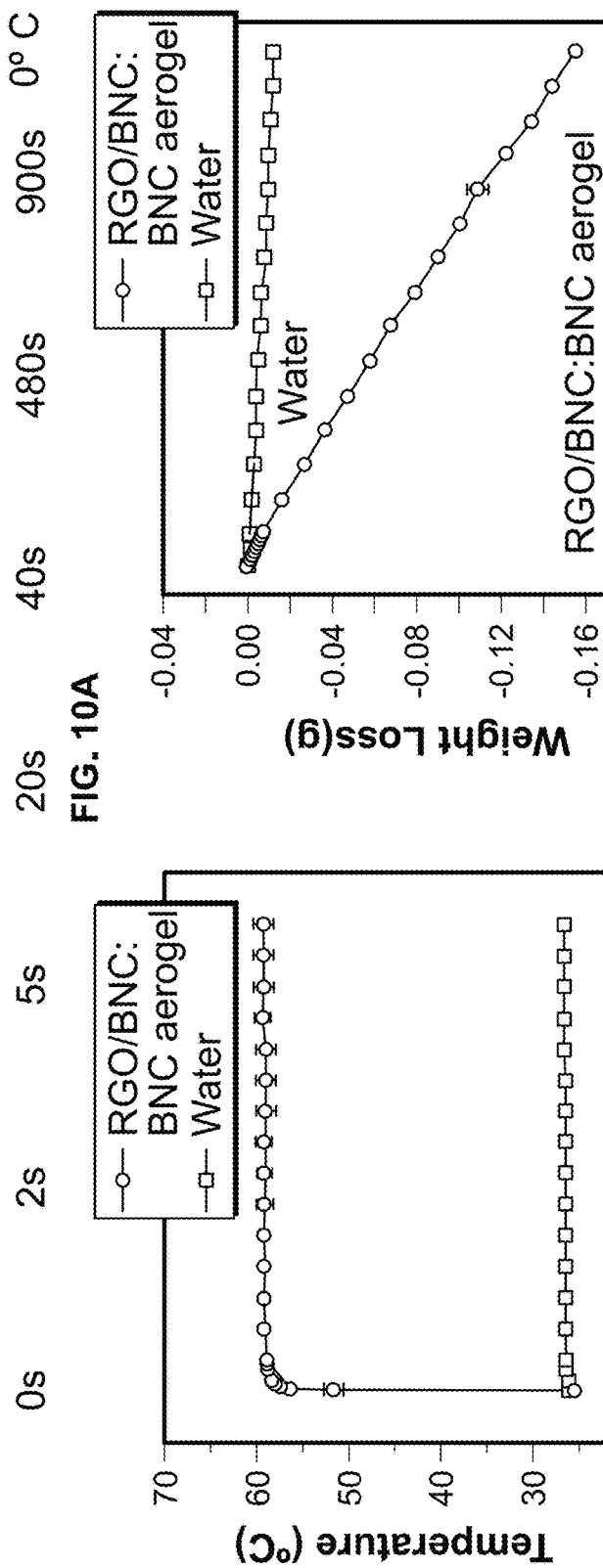
FIG. 10A
FIG. 10B
FIG. 10C

BILAYERED STRUCTURES FOR SOLAR STEAM GENERATION

CROSS-REFERENCE TO RELATED APPLICATIONS

This application claims priority to U.S. Provisional Application 62/369,934 filed on Aug. 2, 2016 and U.S. Provisional Application 62/426,979 filed on Nov. 28, 2016, both of which are incorporated by reference in their entirety.

STATEMENT REGARDING FEDERALLY SPONSORED RESEARCH & DEVELOPMENT

This invention was made with government support under grants FA9550-15-1-0228 and 12RX11COR awarded by the Air Force Office of Scientific Research. The U.S. government has certain rights in the invention.

BACKGROUND OF THE DISCLOSURE

Meeting the ever increasing fresh water needs of the growing world population is one of the most serious global challenges of the $21^{st}$ century. Apart from the improved use of existing fresh water resources, desalination and water reuse are considered to be critical to overcome water scarcity that is affecting roughly half of the world's population. Two methods, namely, thermal desalination and reverse osmosis technology have been widely employed for desalination of sea water, which represents a virtually unlimited source. Solar water desalination, which relies on a sustainable and renewable energy source, is a promising method to alleviate fresh water scarcity in parts of the world with ample sunlight with low environmental impact. Steam generation using solar energy has been proven to be technically feasible and considered to be highly promising for water purification using sustainable energy source. However, low efficiency due to the heat loss associated with heating the bulk water and the requirement for high optical concentration limit the utilization of solar desalination in stand-alone solar power applications.

Previous designs involve either expensive materials or complex fabrication methods, with poor prospects in terms of scalability. Thus, there is a need for cost-effective and scalable heat-localization layers that provide high steam-generation efficiency. Additionally, most of these materials have a finite lifetime owing to pore clogging, degradation of the photothermal properties, and alteration of the surface properties of the water transport layer. Disposal of these materials can quickly pose a significant threat to the environment and ecosystems. For example, degradation and leaching of nanoscale photothermal materials into marine ecosystems, where these materials are most likely deployed can have lasting negative consequences. Thus, there is a need for a biodegradable composition for solar steam generation that provides high steam generation efficiency.

BRIEF SUMMARY OF THE DISCLOSURE

In one embodiment of the present disclosure, a composition comprising cellulose and a nanomaterial is disclosed.

In another embodiment of the present disclosure, a method for generating steam is disclosed. The method comprises placing a composition comprising cellulose and at least one nanomaterial in water; and exposing the composition to radiation thereby generating steam.

In yet another embodiment of the present disclosure, a method for the preparation of potable water is disclosed. The method comprises placing a composition comprising cellulose and at least one nanomaterial in water; exposing the composition to radiation thereby generating steam; and, condensing the steam thereby preparing potable water.

In another embodiment of the present disclosure, a method for the preparation of a bilayered biofilm comprising nanocellulose and a nanomaterial is disclosed. The method comprises providing a bacterial culture of *Gluconacetobacter hansenii* in a growth media; incubating the bacterial culture and the nanomaterial until a first biofilm layer forms; adding additional growth media on top of the first biofilm layer, the additional growth media comprising the bacterial culture and not comprising a nanomaterial; and, incubating the bacterial culture until a second biofilm layer forms thereby forming a bilayered biofilm. One of the bacterial cultures in growth media further comprises a nanomaterial.

BRIEF DESCRIPTION OF THE DRAWINGS

FIG. 10A is an exemplary embodiment of IR images showing the temperature of water and an RGO/BNC:BNC aerogel upon irradiation in accordance with the present disclosure. FIG. 10B is an exemplary embodiment of a plot showing the surface temperature of water and an RGO/BNC:BNC aerogel as a function of irradiation time in accordance with the present disclosure. FIG. 10C is an exemplary embodiment of a plot showing the cumulative weight loss of water through water evaporation under solar illumination as a function of irradiation time in accordance with the present disclosure.

DETAILED DESCRIPTION OF THE DISCLOSURE

Figure 1A:
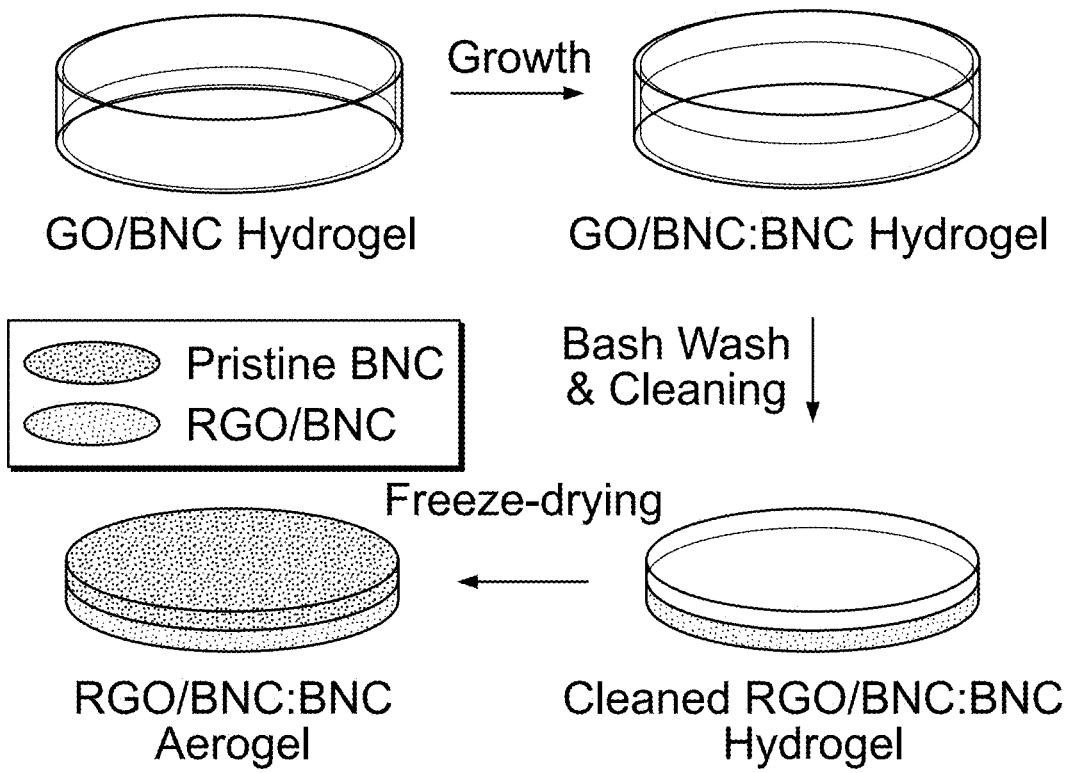
FIG. 1A is an exemplary embodiment of a schematic illustration showing the fabrication of RGO/BNC:BNC aerogel in accordance with the present disclosure.
Figure 1B:
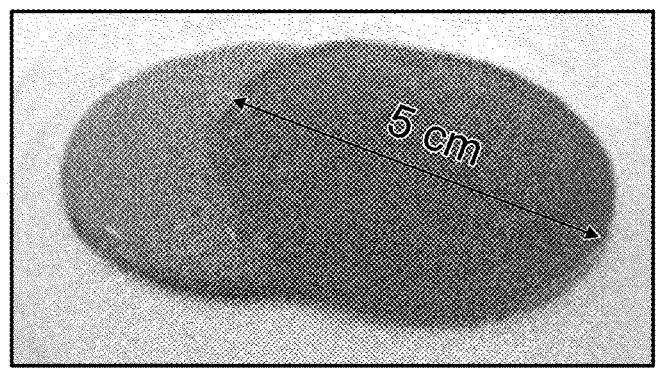
FIG. 1B is an exemplary embodiment of photographs of the cleaned RGO/BNC:BNC hydrogel and RGO/BNC:BNC aerogel in accordance with the present disclosure.
Figure 1B:
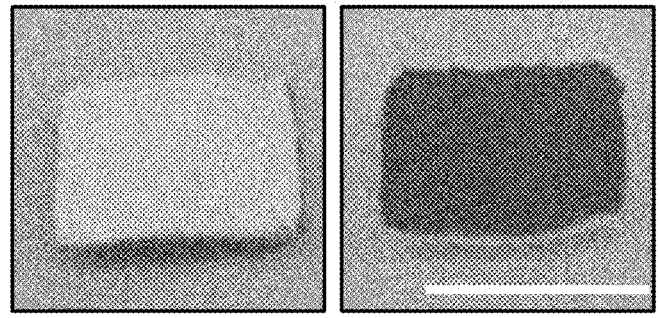
Figure 1C:
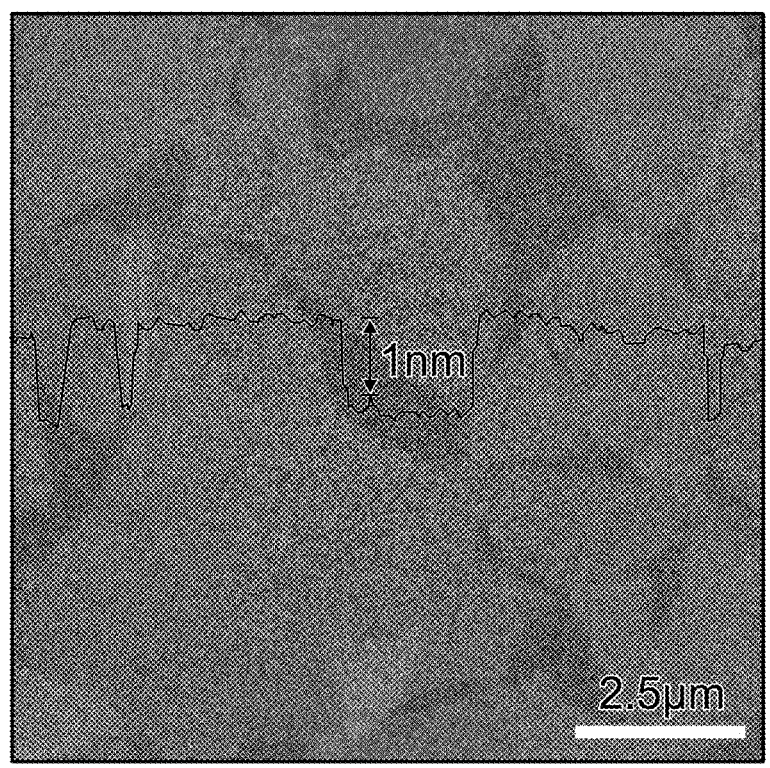
FIG. 1C is an exemplary embodiment of an AFM image of GO flakes deposited on a silicon substrate in accordance with the present disclosure.
Figure 1D:
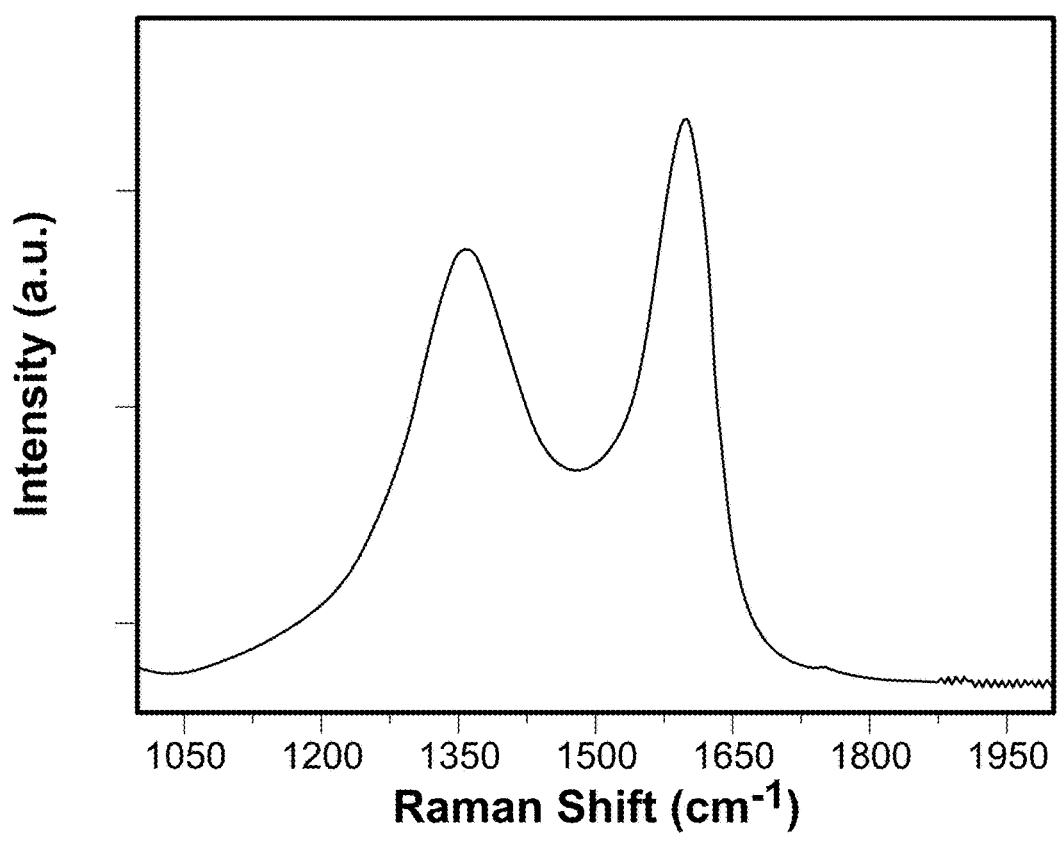
FIG. 1D is an exemplary embodiment of a Raman spectrum of GO flakes in accordance with the present disclosure.
Figure 2A:
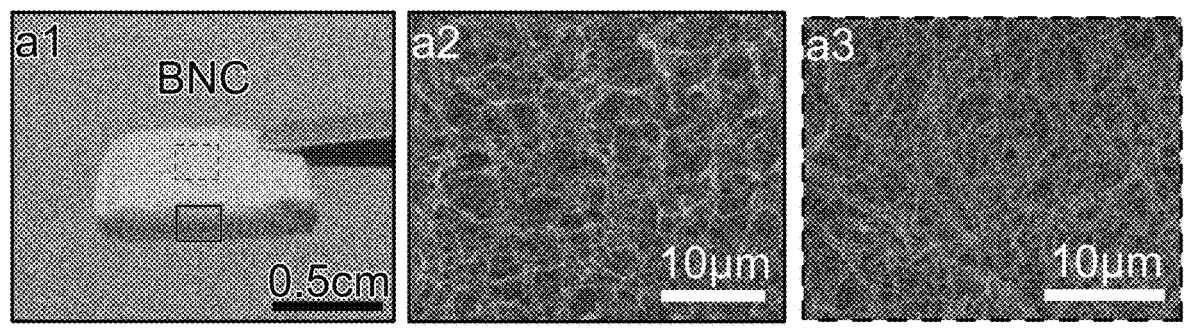
FIG. 2A is an exemplary embodiment of an optical image, an SEM image and a top surface image of a BNC aerogel in accordance with the present disclosure.
Figure 2B:
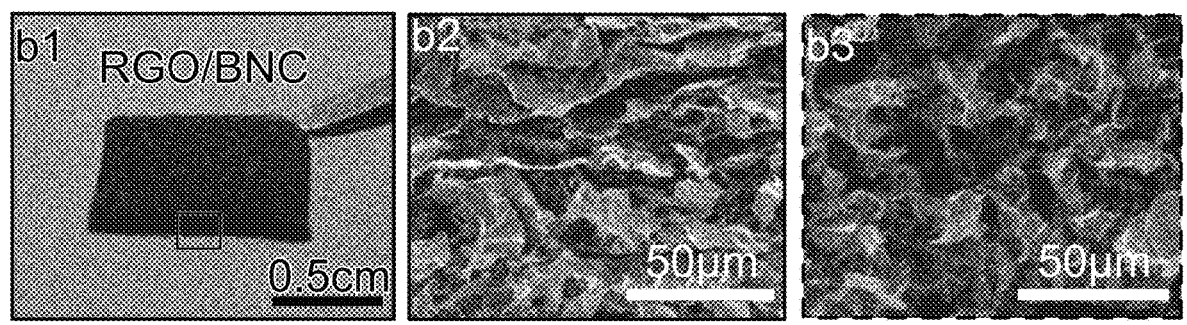
FIG. 2B is an exemplary embodiment of an optical image, an SEM image and a top surface image of an RGO/BNC aerogel in accordance with the present disclosure.
Figure 2C:
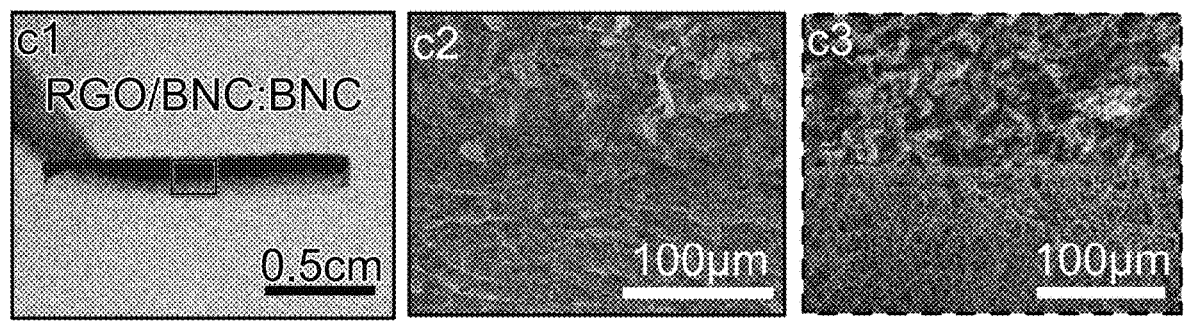
FIG. 2C is an exemplary embodiment of an optical image, an SEM image and a top surface image of an RBO/BNC:BNC aerogel in accordance with the present disclosure.

The present disclosure is directed to steam generation through the efficient harvesting of solar energy. In particular, the present disclosure is directed to bilayered structures that are cost-effective and scalable that provide high steam-generation efficiency. The bilayered structures include bilayered biofoams (e.g., RGO/BNC) and wood-graphene oxide composites. Steam generation through efficient harvesting of solar energy is highly promising for large-scale power generation, desalination, and water purification.

Confining heat to air/water interface (i.e., the evaporating surface) is considered to be a highly promising approach to improve the efficiency of evaporation and the steam-generation process. Steam generation through heat localization at the evaporation surface involves large optical absorption at the surface, photothermal (light-to-heat) conversion of incident light, confinement of heat to the evaporative surface, and transport of water from the bulk to the heat localization layer for efficient evaporation. Over the past several years, various heat localization layers have been demonstrated to significantly improve the steam-generation efficiency compared to conventional bulk heating methods.

A number of efforts have been dedicated to the use of novel nanomaterials as light absorbing and heat generating materials. For example, plasmonic nanostructures, which exhibit large absorption and scattering of light in the visible and near infrared (NIR) regions of the electromagnetic spectrum, have been demonstrated to be excellent candidates for steam generation. Owing to their photothermal properties, carbon-based materials such as graphene, carbon black nanoparticles and carbon foam have also been employed for solar steam generation.

Apart from the materials employed in the photothermal layers, support materials on which the photothermal layers are deposited are equally important for a high-efficiency solar steam generation. The key considerations for such support materials are hydrophilicity and porosity for efficient transport of water from the bulk to the evaporative surface, low thermal conductivity to impede the flow of heat from the evaporative surface to the bulk water, lightweight to ensure that the materials remain afloat on water surface, and cost-efficiency and scalability for real-world application. A number of materials such as anodic aluminum oxide (AAO) membrane, gauze, paper have been employed as the supporting materials for steam generation.

The present disclosure minimizes heat losses and improves the efficiency of water desalination by using a bilayered structure for solar steam generation. In a typical bilayered structure, the top layer is comprised of a photothermal material that efficiently absorbs light and converts it into heat. The bottom layer, typically with low thermal conductivity, serves as a thermal insulation layer to minimize the heat loss to the bulk water, thus improving the overall efficiency of the solar steam generation.

Yet another promising photothermal material, graphene oxide (GO), exhibits a broadband light absorption from visible to NIR range, making it excellent for steam generation applications. The unique optical properties of GO have been investigated for various optoelectronic and biomedical applications.

Disclosed herein is that a number of the inherent physical and chemical properties of wood such as high porosity, lightweight, low thermal conductivity and hydrophilicity, make it an excellent material for a solar steam generation. A wood-graphene oxide (GO) composite for solar steam generation enables heat localization at the evaporative surface and provides efficient transport of water to the evaporative surface through the microchannels of the wood. The unique properties of wood, as well as GO, are well-suited for high optical absorption, photothermal conversion, heat localization, water transport and rapid evaporation resulting in a highly efficient solar steam generation system. The wide availability of wood combined with the simple coating process makes the wood-GO composite demonstrated highly attractive for steam generation and water distillation in resource-limited settings with ample sunlight.

Additionally, a bilayered hybrid biofoam composed of bacterial nanocellulose (BNC) and reduced graphene oxide (RGO) for solar steam generation through heat localization at the evaporation surface is disclosed. BNC is composed of highly pure cellulose nanofibrils, produced from dextrose through a series of biochemical steps followed by the self-assembly of the secreted cellulose fibrils from bacteria in the culture medium. BNC is a highly attractive material for the fabrication of functional foams due to its large specific surface area, open microporous structure, excellent mechanical properties, and facile and scalable synthesis. So far, most of the functional foams based on BNC rely on either in situ growth or adsorption of functional nanostructures or infiltration of polymers in the porous cellulose network after harvesting the BNC from the culture. A novel approach for the fabrication of photothermally active biofoam involves the in situ incorporation of GO flakes into BNC during its growth. The bilayer structure of the functional foam is tailored for high optical absorption, photothermal conversion, heat localization, and water transport to the evaporation surface resulting in a highly efficient solar steam generation. The bilayer structure exhibits excellent stability even under vigorous mechanical agitation and harsh chemical conditions, which is quite surprising considering the simplicity of the manner of fabrication.

Graphene oxide (GO) exhibits a broad optical absorption over the visible and near infrared (NIR) parts of the electromagnetic spectrum and excellent photothermal transduction. Unlike graphene flakes, which tend to stack and aggregate in aqueous solutions, GO exhibits excellent water solubility. GO is essentially sheets of graphene with carboxylic functional groups at the edges and phenol hydroxyl and epoxide groups on the basal planes. Thus, the hydrophilicity of GO is attributed to the hydroxyl and epoxide groups on the basal planes and carboxyl functionalities at the edges. Crumpled graphene oxide and crumpled reduced graphene oxide produced by aerosol synthesis methods also exhibit excellent stability and hydrophilicity. Graphene-based materials have been extensively investigated for various optoelectronic applications, including transparent electrodes, photodetectors, and as electron- and hole-transport layers in photovoltaic devices. While being electrically conductive, a single layer of graphene exhibits only a small optical absorbance (≈3%), making it an excellent candidate for transparent electrodes. However, the cumulative optical absorbance of a few graphene monolayers in tandem can quickly add up, making graphene materials an excellent choice for applications demanding high optical absorption.

In accordance with some embodiments of the disclosure, a composition comprising cellulose and a nanomaterial is disclosed. In some embodiments, the cellulose is a gel that comprises nanocellulose, and the nanomaterial is graphene oxide, reduced graphene oxide or a combination thereof. This composition has numerous uses, including, but not limited to, localizing heat at the surface of water to efficiently generate steam using solar radiation. The water may or may not be suitable for human consumption prior to steam generation. In some embodiments, steam is condensed and collected thereby generating water that is suitable for human consumption.

In some embodiments, the composition comprises cellulose and graphene oxide, reduced graphene oxide or both. In some embodiments, the cellulose is wood. This composition has numerous uses including, but not limited to, localizing heat at the surface of water to efficiently generate steam using solar radiation. The water may or may not be suitable for human consumption prior to steam generation. In some embodiments, steam is condensed and collected thereby generating water that is suitable for human consumption.

Definitions

The term "aerogel" as used herein refers to the resulting composition when all of the liquid in a gel is replaced with a gas or mixture of gases (e.g., air). They are extremely low density solids having very low thermal conductivity.

The term "gel" as used herein is a group of polymeric materials whose structure renders them capable of holding large amounts of a liquid in their three-dimensional networks. By weight, gels are mostly liquid, yet they behave like solids due to a three-dimensional cross-linked network within the liquid. "Hydrogels" are gels in which the liquid is water.

The term "nanocellulose" as used herein refers to nanostructure cellulose composed of thixotropic nanosized cellulose fibrils with a high length to width ratio. They are prepared by different methods, including, but not limited to, bacterial growth and acid hydrolysis of native cellulose fibers.

The term "biodegradable" as used herein means capable of being broken down (decomposed) by the action of bacteria, microorganisms or other living organisms. In most instances, a substance is biodegradable if it is broken down into substances that are not harmful to the environment. It is recognized that the harm caused by decomposition products may not be recognized for many years after the break down occurs or additional research is performed. "Not harmful to the environment" as used herein refers to the state of the art as is known upon the submission of this application.

The term "steam" as used herein refers to water in the vapor phase. It is not limited to water at or above 100° C. at standard atmospheric pressure.

The terms "efficiency of steam generation" or "steam-generation efficiency" as used herein are interchangeable and is quantified by measuring the weight loss of water (due to water evaporation) as a function of irradiation time.

The term "evaporation efficiency" ($\eta$) as used herein is determined from the following equation:

$$\eta = \frac{mh_{LV}}{l}$$

where m is the evaporation rate, $h_{LV}$ is the total enthalpy of sensible heat (294 J/g, from 30 to 100° C. with a specific heat of 4.2 J·g/K and phase change of liquid to water (2256 J/g)), and l is the incident laser power density. It measures the photothermal efficiency in a system (i.e., light to heat conversion).

In some aspects of this disclosure, the cellulose is in the form of nanocellulose. In some embodiments, the nanocellulose is in the form of cellulose nanofibers, microfibrillated cellulose, nanocrystalline cellulose, bacterial nanocellulose and combinations thereof.

In some aspects, bacterial nanocellulose (BNC) is used. BNC is composed of highly pure cellulose nanofibrils. One method of production of BNC is from dextrose through a series of biochemical steps followed by the self-assembly of the secreted cellulose fibrils from bacteria in the culture medium. BNC is a highly attractive material for the fabrication of functional foams due to its large specific surface area, open microporous structure, excellent mechanical properties, and facile and scalable synthesis. Most of the functional foams based on BNC rely on either in situ growth or adsorption of functional nanomaterials or infiltration of polymers in the porous cellulose network after harvesting the BNC from the culture.

In some embodiments, the BNC is formed in the presence of at least one nanomaterial. The term "nanomaterial" as used herein refers to a solid material having one, two or three of its dimensions less than about 1000 nanometers, preferably about 500 nanometers, most preferably about 100 nanometers. Said materials can either occur naturally in nature or be manufactured. They comprise a variety of shapes, sizes and properties. Examples include, but are not limited to, fullerenes, carbon nanotubes, quantum dots, graphene oxide flakes, ceramics, clays, and metal nanoparticles (e.g., gold and silver). They are often divided into four categories: carbon-based, metal-based, dendrimers, and composites.

In some embodiments, BNC is formed in the presence of a nanomaterial thereby forming a nanocomposite material. As used herein, the term "nanocomposite material" means a composition comprising at least two phases, wherein at least one of the phases is a nanomaterial. For example, in some embodiments, the nanocomposite material comprises cellulose or nanocellulose and a nanomaterial such as molybdenum disulfide nanoparticles, functionalized carbon nanotubes, polydopamine nanoparticles, graphene, graphene oxide, reduced graphene oxide or a combination thereof. In some embodiments, the nanomaterial is polydopamine, graphene oxide, reduced graphene oxide or a combination of both. In some embodiments, the composition is an aerogel, a hydrogel, a colloid, a porous media, a polymer, a copolymer or combinations thereof. In some embodiments, the nanomaterial is preferably polydopamine. In yet another embodiment, the nanomaterial is preferably graphene oxide, reduced graphene oxide or a combination thereof.

When the BNC is formed in the presence of the nanomaterial, it provides a more robust nanocomposite material such that the nanomaterial is not easily removed from the BNC gel matrix. The BNC gel matrix comprising the nanomaterial is stable to sonication for at least about 10 minutes, at least about 20 minutes, at least about 30 minutes, at least about 45 minutes, at least about one hour, at least about two hours, or at least about five hours.

In some embodiments, the BNC is formed in the presence of graphene oxide (GO) flakes, reduced graphene oxide flakes or a combination thereof. Graphene oxide flakes can be commercially obtained or prepared by methods known in the art. In some embodiments, the graphene oxide flakes are reduced forming reduced graphene oxide (RGO). Formation of RGO from GO may be prior to, coinciding with, or subsequent to incorporation into the BNC. The graphene oxide may be partially or completely reduced. In some embodiments, none of the graphene oxide is reduced. In some embodiments, over about 10% of the graphene oxide is reduced, over about 15% of the graphene oxide is reduced, over about 20% of the graphene oxide is reduced, over about 25% of the graphene oxide is reduced, over about 30% of the graphene oxide is reduced, over about 35% of the graphene oxide is reduced, over about 40% of the graphene oxide is reduced, over about 45% of the graphene oxide is reduced, over about 50% of the graphene oxide is reduced, over about 55% of the graphene oxide is reduced, over about 60% of the graphene oxide is reduced, over about 65% of the graphene oxide is reduced, over about 70% of the graphene oxide is reduced, over about 75% of the graphene oxide is reduced, over about 80% of the graphene oxide is reduced, over about 85% of the graphene oxide is reduced, over about 90% of the graphene oxide is reduced, over about 95% of the graphene oxide is reduced, or about 100% of the graphene oxide is reduced.

The concentration of graphene oxide or reduced graphene oxide in the cellulose matrix is determined by the amount of graphene oxide added during formation of the gel. In some embodiments, the GO or RGO concentration, as measured by thermogravimetric analysis, is from about 2 wt. % to about 50 wt. %, about 3 wt. % to about 48 wt. %, about 4 wt. % to about 45 wt. %, about 7 wt. % to about 40 wt. %, about 10 wt. % to about 38 wt. %, about 13 wt. % to about 35 wt. %, about 15 wt. % to about 32 wt. %, about 20 wt. % to about 30 wt. %, about 25 wt. % to about 30 wt. %. In some embodiments the GO or RGO concentration is about 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, 35 wt. %, 36 wt. %, 37 wt. %, 38 wt. %, 39 wt. %, 40 wt. %.

In some embodiments, the BNC is formed in the presence of polydopamine nanoparticles. Polydopamine (PDA), formed by the oxidation of dopamine, is an important eumelanin-like biopolymer known for its versatile adhesion properties and universal surface modification. PDA particles can be obtained by methods known in the art. The size of the PDA particles may be controlled during the polymerization reaction by altering the concentration of ammonia in the reaction. In some embodiments, the PDA particles are about 0.05 μm in diameter, 0.1 μm in diameter, 0.2 μm in diameter, 0.3 μm in diameter, 0.4 μm in diameter, 0.5 μm in diameter, 0.75 μm in diameter, 1.0 μm in diameter, 1.25 μm in diameter, 1.5 μm in diameter, 1.75 μm in diameter, 2 μm in diameter, 3 μm in diameter, 4 μm in diameter, 5 μm in diameter, 7.5 μm in diameter, 10 μm in diameter, 15 μm in diameter, 20 μm in diameter.

The concentration of PDA in the cellulose matrix is determined by the amount of PDA added during formation of the gel. In some embodiments, the PDA concentration, as measured by thermogravimetric analysis, is from about 2 wt. % to about 60 wt. %, about 3 wt. % to about 58 wt. %, about 4 wt. % to about 55 wt. %, about 7 wt. % to about 50 wt. %, about 10 wt. % to about 48 wt. %, about 13 wt. % to about 45 wt. %, about 15 wt. % to about 42 wt. %, about 20 wt. % to about 40 wt. %, about 25 wt. % to about 40 wt. %. In some embodiments the PDA concentration is about 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, 35 wt. %, 36 wt. %, 37 wt. %, 38 wt. %, 39 wt. %, 40 wt. %, 41 wt. %, 42 wt. %, 43 wt. %, 44 wt. %, 45 wt. %, 46 wt. %, 47 wt. %, 48 wt. %, 49 wt. %, 50 wt. %, 51 wt. %, 52 wt. %, 53 wt. %, 54 wt. %, 55 wt. %, 56 wt. %, 57 wt. %, 58 wt. %, 59 wt. %, 60 wt. %.

In yet another aspect, the BNC and nanocomposite material is biodegradable or comprises mostly biodegradable materials. Mostly in this instances means that at least 75% of the composition comprises biodegradable materials. In still yet another aspect, the BNC and nanocomposite material is comprises only biodegradable materials. PDA is a biodegradable polymer. In some embodiments, the biodegradable composition comprises or consists essentially of BNC and PDA.

Bacteria capable of producing cellulose or nanocellulose include, but are not limited to *Gluconacetobacter hansenii* (ATCC 23769 or ATCC 53582), *Gluconacetobacter xylinus* (formerly named *Acetobacter xylinum*), *Escherichia coli*, *Agrobacterium tumefaciens*, *Acetobacter pasteurianus*, *Asaia bogorensis*, *Rhizobium* spp., *Sarcina ventriculli*, and *Gluconacetobacter sacchari*. In some embodiments, the bacteria for producing nanocellulose is *Gluconacetobacter hansenii*, *Acetobacter pasteurianus*, or *Gluconacetobacter xylinus*. In some embodiments, the bacteria is *Gluconacetobacter hansenii*. The fabrication of a bilayer structure involves growing *Gluconacetobacter hansenii* bacteria in the presence of GO, RGO or a combination thereof.

In some embodiments, the bacterial culture is grown in the presence of GO or RGO flakes until a bacterial film of nanocellulose is formed that incorporates the GO or RGO flakes (BNC/GO or BNC/RGO). In another embodiment, the bacterial culture is grown in the presence of PDA particles until a bacterial film of nanocellulose is formed that incorporates the PDA particles (PDA/BNC). In some embodiments, only one layer is formed while in yet another aspect, more than one layer is formed. Additional layers of the nanocellulose may be formed by adding additional bacterial growth media that comprises the bacterial culture on the surface of the previously formed nanocellulose layer. The additional grown media may or may not comprise the nanomaterial. Each individual layer may or may not comprise the nanomaterial, and the nanomaterial may be the same or different between different layers. This process may be repeated until a plurality of layers is formed. In some embodiments, the final composition will comprise from one to fifty layers, from two to forty layers, from two to thirty layers, from two to twenty layers, from two to ten layers, from two to five layers. Each individual layer may or may not comprise a nanomaterial. In one embodiment, the final composition has two layers wherein one layer comprises the nanomaterial and one layer does not comprise a nanomaterial. In another embodiment, the final composition comprises two layers wherein one layer comprises BNC without any nanomaterial, and the second layer comprises BNC and graphene oxide, reduced graphene oxide, polydopamine or any combination thereof. In some embodiments of the bilayered composition, the first layer formed comprises the nanomaterial and the second formed layer does not comprise a nanomaterial. In yet another embodiment, this is reversed. The first layer formed does not comprise the nanomaterial while the second formed layer does comprise the nanomaterial. In some aspects, the composition comprises only one nanomaterial. In yet another aspect, the composition comprises more than one nanomaterial.

In some embodiments, the nanomaterial is selected from the group consisting of graphene oxide, reduced graphene oxide, molybdenum disulfide ($MoS_2$), polydopamine (PDA, melanin), functionalized multiwalled carbon nanotubes (e.g., —OH, —COOH modified) and combinations thereof.

In some embodiments, each layer of the nanocellulose biofilm has a thickness of from about 0.1 to about 50 mm, from about 0.2 to about 45 mm, from about 0.5 to about 40 mm, from about 0.8 to about 35 mm, from about 1.0 to about 30 mm, from about 1.2 to about 25 mm, from about 1.5 to about 20 mm, from about 1.7 to about 15 mm, or from about 2.0 to about 10 mm.

In another aspect of this disclosure, a method of making steam is presented utilizing the cellulose and nanomaterial composition as disclosed elsewhere herein. By placing the composition on water and exposing said composition to radiation, heat is generated via photothermal conversion of the radiation into heat. The heat is localized within or near the composition thereby heating the water. The amount of steam generated is a function of the amount of heat generated and may be measured as a function of time. In some embodiments, the water is condensed. The condensation of the water may be into a separate physical location as the source water thereby affecting a distillation or purification of the source water. If the source water is not suitable for human consumption, this method may be utilized to prepare potable water.

The steady state evaporation rate of water comprising the cellulose and nanomaterial composition is a function of its structure and manner in which the exposure to radiation is done. A nonlimiting list of factors that affect the steady state evaporation rate of water include cellulose type, nanomaterial identity, nanomaterial concentration, number of layers of the composition, thickness of the composition, and strength and nature of the radiation used. The steady state evaporation rate is determined as described in the Examples herein. In some embodiments, the steady state evaporation rate under simulated solar irradiation (e.g., 10 kW/m$^2$) is greater than greater than about 6 kg/m$^2$·h, greater than about 7 kg/m$^2$·h, greater than about 8 kg/m$^2$·h, greater than about 9 kg/m$^2$·h, greater than about 10 kg/m$^2$·h, greater than about 11 kg/m$^2$·h, greater than about 12 kg/m$^2$·h, greater than about 13 kg/m$^2$·h, greater than about 15 kg/m$^2$·h, greater than about 20 kg/m$^2$·h, or greater than about 25 kg/m$^2$·h.

In some embodiments, the steady state evaporation rate under a simulated solar beam irradiation (e.g., 10 kW/m$^2$) is 1.5 times greater than that compared to an equivalent sample under identical conditions without the cellulose and nanomaterial composition present. In some embodiments, the steady state evaporation rate is about 1.6 times greater, about 1.7 times greater, about 1.8 times greater, about 1.9 times greater, about 2.0 times greater, about 2.1 times greater, about 2.2 times greater, about 2.3 times greater, about 2.4 times greater, about 2.5 times greater, about 2.75 times greater, about 3.0 times greater, about 5 times greater, about 10 times greater, or about 15 times greater.

The evaporation efficiency of water comprising a BNC/RGO composition is a function of layered structure. In some embodiments the evaporation efficiency is greater than about 30%, greater than about 40%, greater than about 50%, greater than about 60%, greater than about 70%, greater than about 80%, greater than about 90%, or greater than about 95%.

The evaporation efficiency of water comprising a PDA/BNC composition is a function of layered structure. In some embodiments the evaporation efficiency is greater than about 30%, greater than about 40%, greater than about 50%, greater than about 60%, greater than about 70%, greater than about 80%, greater than about 90%, or greater than about 95%.

Aerogels have very low thermal conductivity due to their high degree of porosity. This acts as an insulating layer and reduces heat transfer from the surface of the liquid where the aerogel floats into the bulk liquid below thereby increasing heat localization at the surface of the liquid. In some embodiments, the porosity of at least one of the layers in the cellulose and nanomaterial composition is greater than about 60%, greater than about 65%, greater than about 70%, greater than about 75%, greater than about 80%, greater than about 85%, greater than about 90%, greater than about 95%, greater than about 96%, greater than about 97%, or greater than about 98%.

Figure 3A:
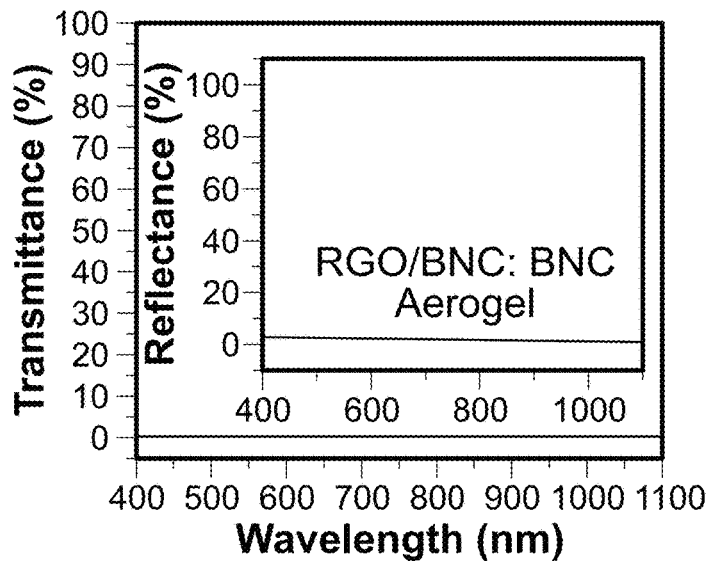
FIG. 3A is an exemplary embodiment of the transmittance and reflectance spectra of an RGO/BNC:BNC aerogel in accordance with the present disclosure.
Figure 3B:
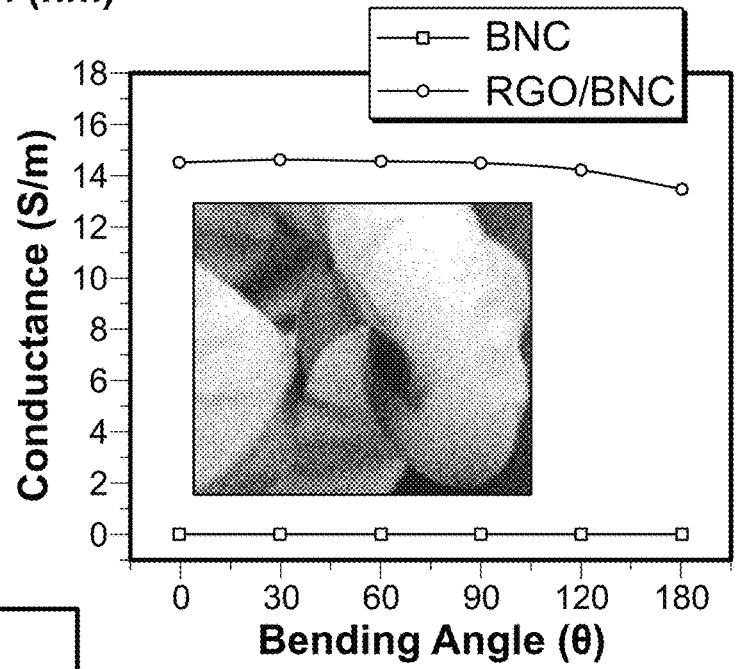
FIG. 3B is an exemplary embodiment of the conductance of an air-dried RGO/BNC:BNC film under various degrees of bending in accordance with the present disclosure.

In some embodiments, the composition is in the form of a bilayer comprising one layer of nanocellulose without a nanomaterial and one layer comprising nanocellulose and a nanomaterial. It (with a thickness of 2.1 mm) exhibits an extremely small optical transmittance (~1.5%) and reflectance (~2.5%) in the visible and near infrared regions, indicating the large optical extinction (~96%) of the bilayer (FIG. 3A). The large extinction of the composition owes to the optical absorption of the RGO flakes and the light scattering from the nanoscale cellulose fibers that increase the optical path length within the bilayer. Such large optical extinction of the bilayer structures combined with the excellent photothermal activity of RGO makes RGO/BNC:BNC excellent for solar steam generation. Natural drying of the RGO/BNC hydrogel (as opposed to freeze drying) resulted in the collapse of the 3D BNC structure into a flexible thin film. This bilayered thin film appeared light gray in color and exhibited a metallic luster, indicating the partial reduction of GO. The electrical conductivity of the thin film was measured on both sides (i.e., RGO/BNC and pristine BNC) under different bending angles (FIG. 3B). The pristine BNC exhibited extremely small electrical conductivity (~2.4×10$^{-6}$ S/m) while the RGO/BNC exhibited significantly higher electrical conductivity (~14.5 S/m), which was found to be insensitive to the bending angle of the flexible film (inset of FIG. 3B). The electrical conductivity of the RGO/BNC film without any special reduction procedure was higher compared to a BNC/silk/multiwalled carbon nanotube (MWCNT) composite membrane (0.2 S/m) and a BNC/polyaniline (PANI) nanocomposite membrane (5 S/m), and was comparable to that of a previous BNC/RGO nanocomposite (23.8 S/m). The naturally dried composition exhibits a decreased steam generation efficiency compared to the freeze dried compositions; however the steam generation efficiency of the naturally dried composition is still greatly improved when compared to water with no cellulose/nanomaterial composition present. The naturally dried composition is still useful if freeze drying is not possible during production.

In some embodiments, bacteria are cultured in a bacterial growth media in the presence of a nanomaterial. In some embodiments, the nanomaterial is PDA, graphene oxide, reduced graphene oxide or a combination thereof. The amount of the nanomaterial is as described elsewhere herein. The bacterial growth media is selected based factors that promote optimal growth of the bacteria and the bacterial film. Those factors are known in the art. The bacteria is grown, for example, in an incubator or other suitable location in order to control temperature, humidity and other factors known in the art to affect bacterial growth. The composition is prepared by providing a bacterial culture in a media suitable for bacterial growth, dispersing a nanomaterial solution into said media, and incubating the bacteria for a predetermined time period or until the bacterial film achieves reaches a specific thickness. In some embodiments, the bacterial film is bacterial nanocellulose.

In some embodiments, the method of preparing the composition comprises forming a plurality of layers where each individual layer may or may not comprise a nanomaterial. When there are a plurality of layers, the nanomaterials may be the same or different than that in the adjacent layer or layers. In some embodiments, there are two layers where one layer comprises a nanomaterial and one layer does not comprise a nanomaterial.

In some embodiments, the bacterium is selected from the group consisting of *Gluconacetobacter hansenii* (ATCC 23769 or ATCC 53582), *Gluconacetobacter xylinus* (formerly named *Acetobacter xylinum*), *Escherichia coli*, *Agrobacterium tumefaciens*, *Acetobacter pasteurianus*, *Asaia bogorensis*, *Rhizobium* spp., *Sarcina ventriculli*, and *Gluconacetobacter sacchari*. Other bacteria that produce bacterial nanocellulose may be used also.

In some embodiments, the bacteria is grown under conditions suitable for bacterial grown for at least about one hour, at least about 1 day, at least about 2 days, at least about 3 days, at least about 4 days, at least about 5 days, at least about 6 days, at least about 7 days, at least about 10 days, at least about 14 days, at least about 21 days. Optionally, after a predetermined number of days, an additional aliquot of bacterial growth solution is added on top of the first biofilm layer. This is optionally repeated after a predetermined time period to create a film having a plurality of layers. The additional aliquots of bacterial growth solution may or may not have a nanomaterial at the same or different concentrations as the previous aliquots. The time period between the addition of additional aliquots may be the same or different as previous time periods and are selected independently from each other based on the desired characteristics of the biofilm.

In some embodiments, after bacterial growth and film formation, the film is harvested. In some embodiments the film is washed with a solvent. The solvent is at room temperature or any temperature up to, and including, the boiling temperature of the solvent. For example, the film may be washed with room temperature or boiling water. The solvent for washing may be pure water, or it may be acidic or basic. In some embodiments, the film is washed with a hot sodium hydroxide solution. One or more washings may be performed, and each wash solvent may be the same or different than other wash solvents, and the temperature may be the same or different than other washings.

In some embodiments, the harvested film is in the form of a hydrogel. The hydrogel may be washed with water that is neutral, acidic or basic one or more times. The washing may be at any temperature where the water remains a liquid up to, and including, boiling temperature. One or more washings may be performed, and each wash solvent may be the same or different than other wash solvents, and the temperature may be the same or different than other washings.

Harvesting of the bacterial film is done when a predetermined thickness is reached. In some embodiments the thickness is from about 0.1 to about 50 mm, from about 0.2 to about 45 mm, from about 0.5 to about 40 mm, from about 0.8 to about 35 mm, from about 1.0 to about 30 mm, from about 1.2 to about 25 mm, from about 1.5 to about 20 mm, from about 1.7 to about 15 mm, or from about 2.0 to about 10 mm.

In some embodiments, the harvested film is freeze dried. The freeze drying may be performed on the washed film or hydrogel or before the film or hydrogel is washed. Freeze drying is performed using standard techniques as are known in the art. The film or hydrogel may be cut into different sizes or shapes before or after freeze drying. Freeze drying may be before or after washing.

In some embodiments, the harvested film is naturally dried—as in placed in a location where the solvent present is permitted to naturally drain and/or evaporate. The temperature may be at any temperature up to, and including the boiling temperature of the solvent. In some embodiments, the solvent is water and the film is dried at ambient temperature. Drying may be before or after washing.

The harvested biofilm comprising nanocellulose and nanomaterial may also be dialyzed to remove residual growth media or other undesired components that may remain after washing. In some embodiments, the composition is dialyzed one or more times in water. The water may be deionized water, distilled water, double distilled water or nanopure water. The composition may be dialyzed one or more times, and the same or different water purity may be used each time. Each time the composition is dialyzed, the dialysis may last for from 30 minutes to five days with any increment of time in between. The time period and number of times for dialysis will be selected based on the degree of purity desired for the composition. A greater number of dialysis steps with a higher degree of water purity will result in a greater level of purity of the composition.

In some embodiments, the cellulose and nanomaterial composition disclosed herein is used to purify water. The water may be pure or impure, or the purity may not be known. "Impure" as used herein refers to water that is not suitable for human and/or animal consumption without purification. Examples of impure water include, but are not limited to, salt water (e.g., from the ocean), septic or sewage waste water, storm water runoff, or any other water that is not suitable for consumption by a human without purification or treatment. Examples of pure water include, but are not limited to, water from a faucet, a tap or a well that is suitable for human consumption without additional purification or treatment.

Because the density of a hydrogel or an aerogel is much less than most liquids, the composition will often float on the surface of the liquid. However the composition may have a higher or lower density than the liquid, or it may have neutral buoyancy. In some embodiments, the composition has a lower density than the liquid and floats.

In some embodiments, a method of heating water may be used to purify water in, for example, a desalinization process. Other uses for this method of heating water include the preparation of potable water that is suitable for human consumption wherein the liquid is an impure water source, including, but not limited to, salt water, brackish water, waste water, storm drain runoff, sewage treatment waste, river or lake water, contaminated water due to improper purification, contaminated water due to improper handling and/or transport. The preparation of potable water can be used after a natural occurrence when traditional safe water supplies have been compromised. In another embodiment, the preparation of potable water is used in rural or developing communities where access to safe drinking water supplies is limited.

Wood-Graphene Oxide Composite

Figure 11:
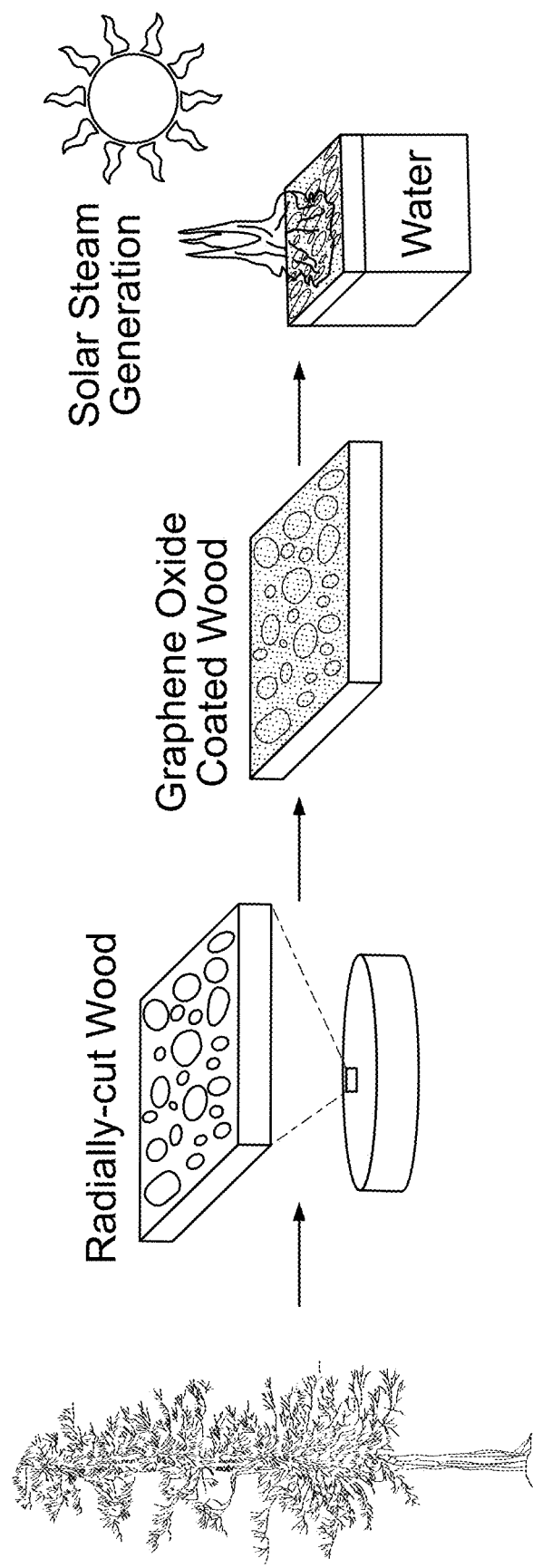
FIG. 11 is an exemplary embodiment of a schematic illustration depicting the fabrication of a wood-GO composite and set-up for solar steam generation in accordance with the present disclosure.
Figure 12A:
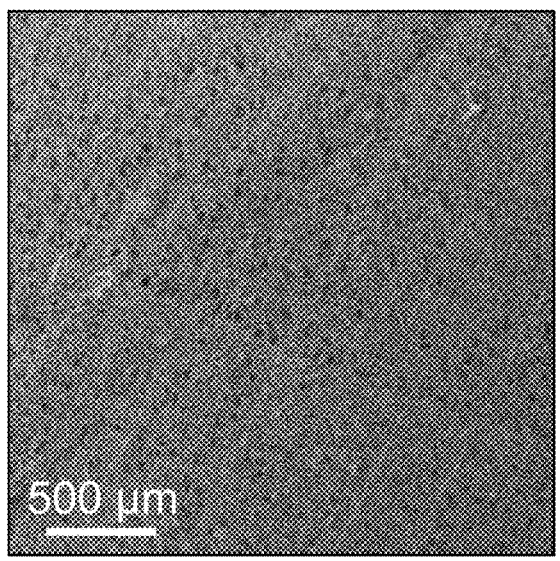
FIG. 12A is an exemplary embodiment of a low-magnification SEM image of a wood cross-section of the microchannel structures of wood in accordance with the present disclosure.
Figure 12B:
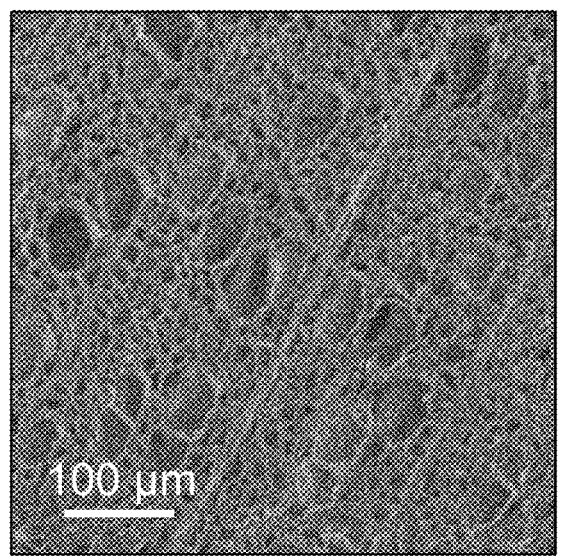
FIG. 12B is an exemplary embodiment of a high-magnification SEM image of a wood cross-section of the microchannel structures of wood in accordance with the present disclosure.
Figure 12C:
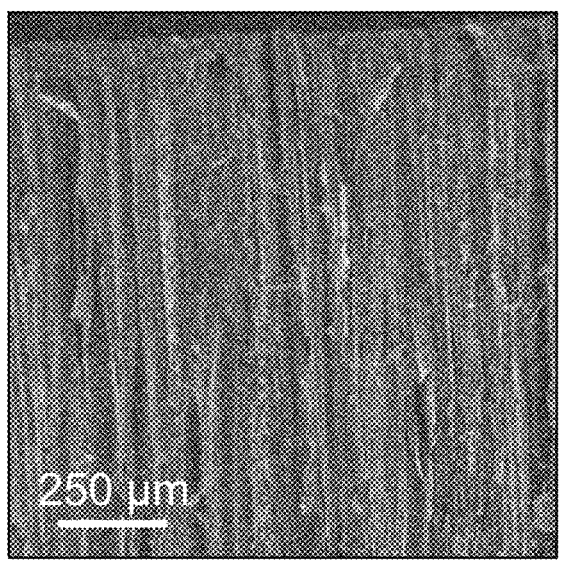
FIG. 12C is an exemplary embodiment of an SEM image of microchannels in wood in accordance with the present disclosure.
Figure 12D:
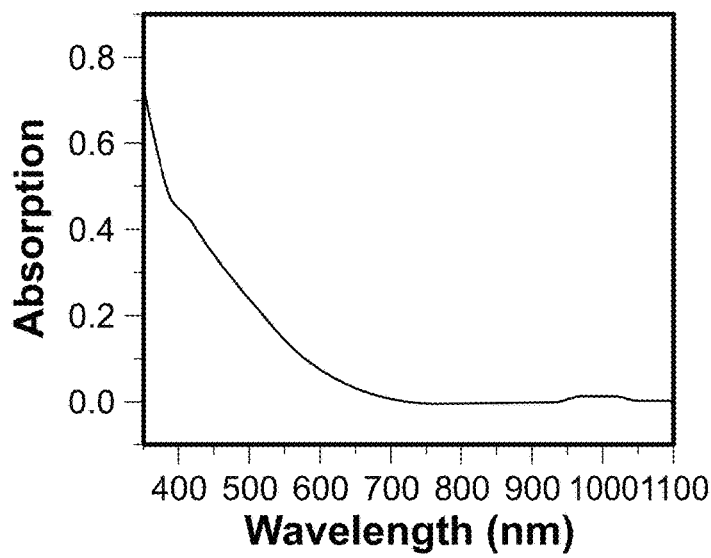
FIG. 12D is an exemplary embodiment of an absorption spectrum of radially-cut wood in accordance with the present disclosure.

Owing to its abundance, biocompatibility, and natural vessel structure, wood has attracted significant attention in various advanced applications including green electronics, biological devices, bioenergy and energy storage. The fabrication of wood-GO composite involves the deposition of GO flakes on the surface of a radially cut piece of wood (FIG. 11). SEM image of the top surface of the wood depicts the highly porous microstructure of wood (FIGS. 12A, 12B). Cross-sectional SEM image reveals long cylindrical microchannels with a diameter of a few tens of microns (FIG. 12C). It is known that wood cells (axial tracheids) exhibit cylindrical structure with a high aspect ratio and primarily run parallel to the trunk of the tree. These high aspect ratio microchannels combined with ray cells that run radially from the heartwood to the bark, form a continuous porous network that enables the transport of water and nutrients. This disclosure exploits the microchannel network in the wood to transport water from the bulk to the photothermally active layer at the evaporative surface. The extinction spectrum of the wood depicts the broad optical absorption in the visible part of the electromagnetic spectrum (FIG. 12D). The broad optical absorption of wood has an appreciable overlap with the solar spectrum causing a significant temperature under solar illumination.

Figure 12E:
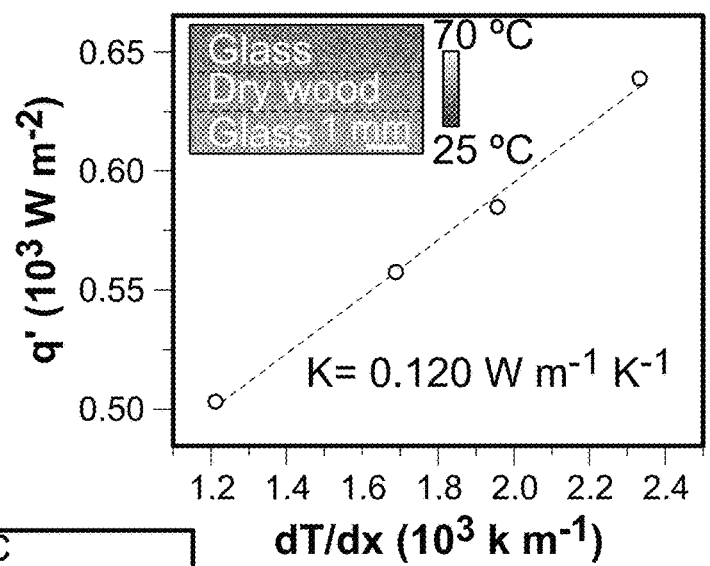
FIG. 12E is an exemplary embodiment of the thermal conductivity of wood in a dry-state.

A low thermal conductivity of the support layer is important to ensure confinement of the photothermally generated heat to the evaporative surface. To investigate the ability of wood to confine heat at the evaporative surface, the thermal conductivity of wood in both wet and dry states was determined. It was obtained using infrared images of wood sandwiched between two glass slides held at two different temperatures. The IR images of the wood show a gradient in the temperature along the thickness of the sample (inset of FIG. 12E). The thermal conductivity of wood in the dry state was found to be 0.120 W/m·K, which is higher than that of air (0.024 W/m·K at room temperature) and significantly lower than that of water (0.600 W/m·K) (FIG. 12E).

Figure 12F:
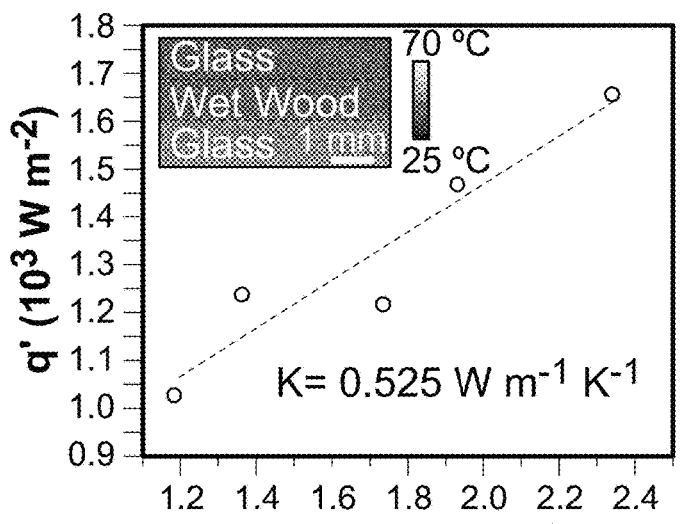
FIG. 12F is an exemplary embodiment of the thermal conductivity of wood in a wet-state. The insets in FIGS. 12E and 12F depict the temperature gradient along the thickness of wood in accordance with the present disclosure.

Wood as a support material with a low thermal conductivity, efficiently suppressed photothermal heat transfer to the bulk water and improve the solar steam generation efficiency. Since the wood is in a hydrated state during solar steam generation, the thermal conductivity in the wet state was determined. For the wet wood, the thermal conductivity was found to be 0.525 W/m·K (FIG. 12F), which is larger than that in the dry state but is still lower than the thermal conductivity of water and seawater. The thermal conductivity of wood in the wet state is comparable to the heat-insulating materials reported in recent literature for solar steam generation. This value is lower than an exfoliated graphite layer with water (0.959 W/m·K), which has been employed for solar steam generation.

Figures 13A, 13B:
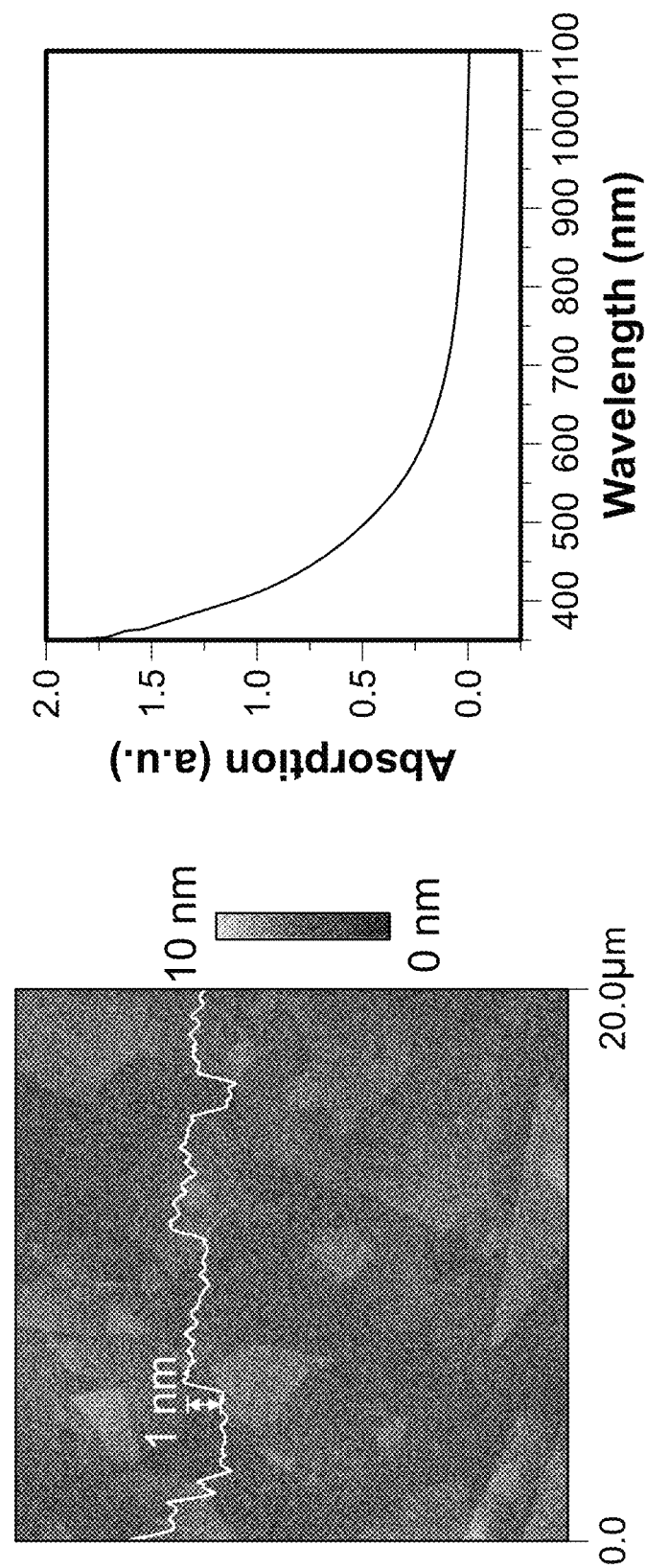
FIG. 13A is an exemplary embodiment of an AFM image of GO flakes deposited on a silicon substrate in accordance with the present disclosure.
FIG. 13B is an exemplary embodiment of an absorption spectrum of GO flakes dispersed in water in accordance with the present disclosure.

GO flakes were synthesized using a method reported by Tour and co-workers. Atomic force microscopy (AFM) image revealed the thickness of GO flakes deposited on a silicon substrate to be ~1.0 nm (FIG. 13A). The thickness of GO flakes corresponds to monolayer and bilayers of GO. The Raman spectrum of GO flakes revealed the characteristic graphite band (G-band) at ~1580-1600 $cm^{-1}$ and defect band (D-band) at ~1330-1350 $cm^{-1}$. GO flakes dispersed in water exhibited a broad optical absorption in the visible and NIR parts of the electromagnetic spectrum (FIG. 13B).

Figure 14A:
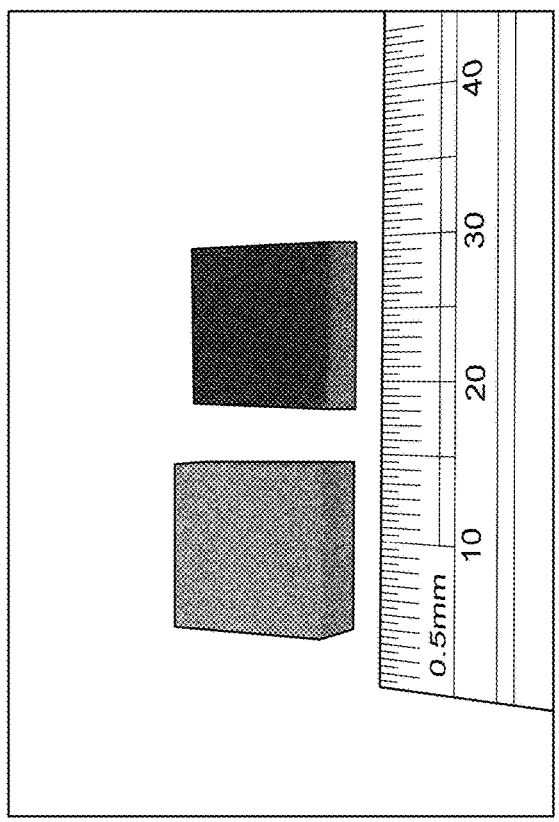
FIG. 14A is an exemplary embodiment of an optical image of wood with and without GO flakes in accordance with the present disclosure.
Figure 14C:
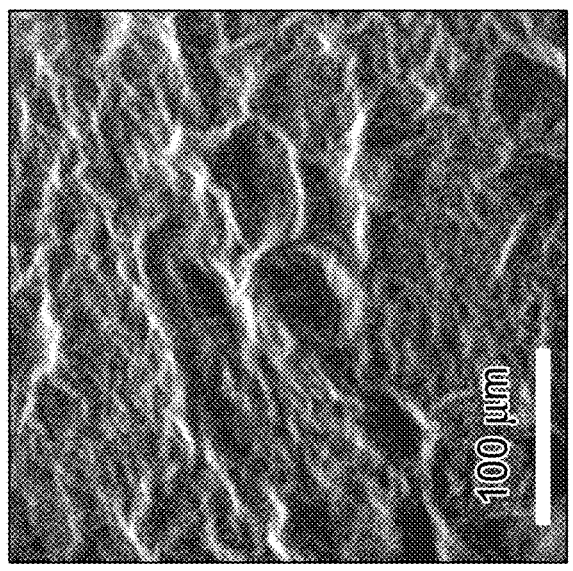
FIG. 14C is an exemplary embodiment of an SEM image of a wood cross-section with GO on the surface of the microporous structure in accordance with the present disclosure.
Figure 14B:
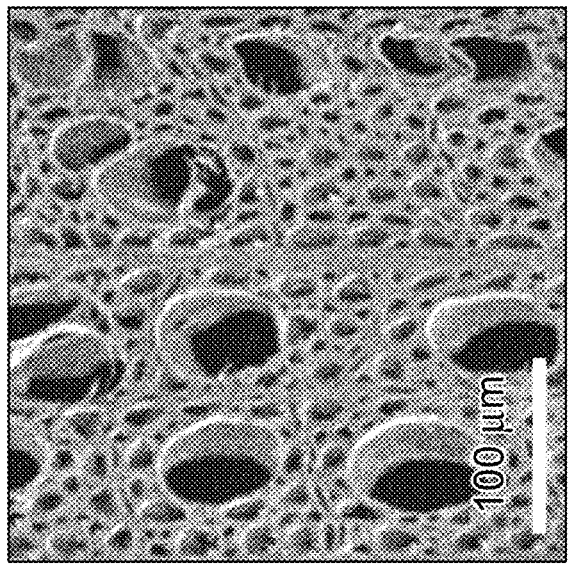
FIG. 14B is an exemplary embodiment of an SEM image of a wood cross-section without GO on the surface of the microporous structure in accordance with the present disclosure.
Figure 14E:
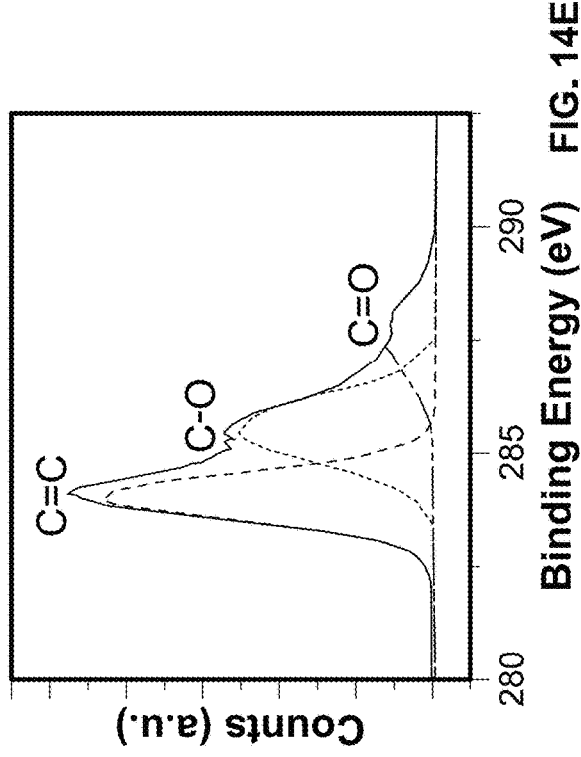
FIG. 14E is an exemplary embodiment of an XPS spectrum of wood in accordance with the present disclosure.
Figure 14D:
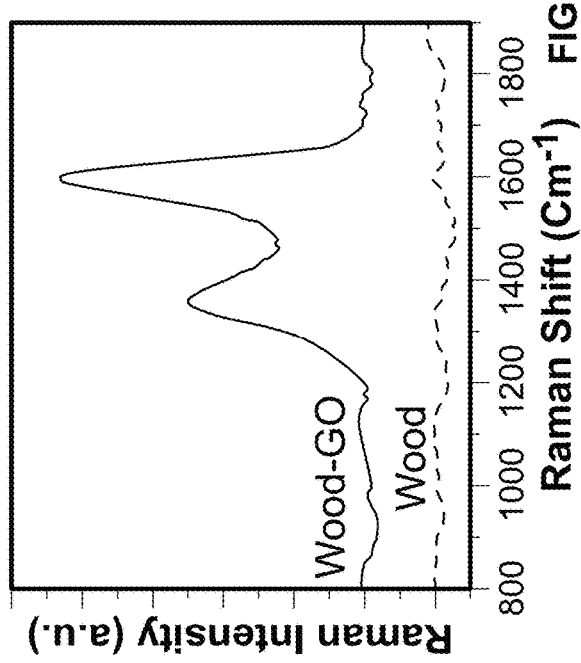
FIG. 14D is an exemplary embodiment of a Raman spectrum of wood with and without GO flakes coating on the surface in accordance with the present disclosure.
Figure 14F:
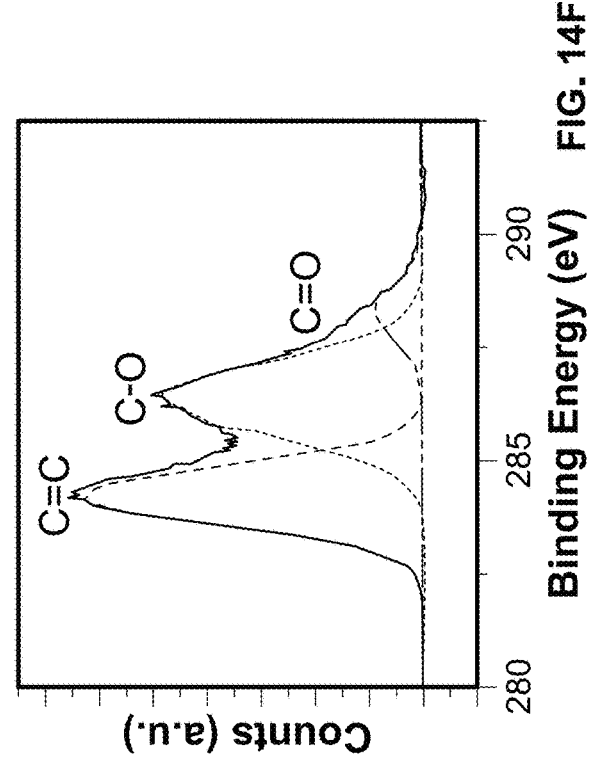
FIG. 14F is an exemplary embodiment of an XPS spectrum of a wood-GO composite in accordance with the present disclosure.

Wood-GO composites were prepared by depositing an aqueous GO solution on the surface of the wood followed by natural drying. Following deposition on the wood surface, the bilayered structure is evident from dark layer on the light colored wood (FIG. 14A). SEM images revealed the complete and conformal coverage of the microporous structure of wood with the GO layer (FIGS. 14B, 14C). The thickness of the GO layer was around 1.1 µm. It has been recently demonstrated that even for thick GO layers, an unimpeded permeation of water occurs through nanoscale pores, which has been employed for water filtration. This large permeation of the water is highly advantageous for solar steam generation when the GO layers are suspended on porous and thermally insulating support layers such as wood. Raman spectra of wood-GO composite revealed the characteristic G-band (~1580-1600 $cm^{-1}$) and D-band (~1330-1350 $cm^{-1}$) corresponding to GO (FIG. 14D). X-ray photoelectron spectroscopy (XPS) was employed to investigate the surface chemical composition of wood and wood-GO composite (FIGS. 14E, 14F). The 1 s spectra of carbon was deconvoluted into three peaks corresponding to the $sp^2$ domains (C=C with a binding energy of 284.5-285 eV and the $sp^3$ domains (C—O with a binding energy of 286 eV and C=O with a binding energy of 288 eV). The C/O ratio obtained from the area under the peaks corresponding to $sp^2$ domains and oxidized $sp^3$ domains, show a decrease in the C/O ratio from wood sample (C/O=1.96) to wood-GO sample (C/O=1.90). The increase in the oxygen bearing groups at the surface confirmed the successful deposition of GO on the surface of the wood.

Figure 15A:
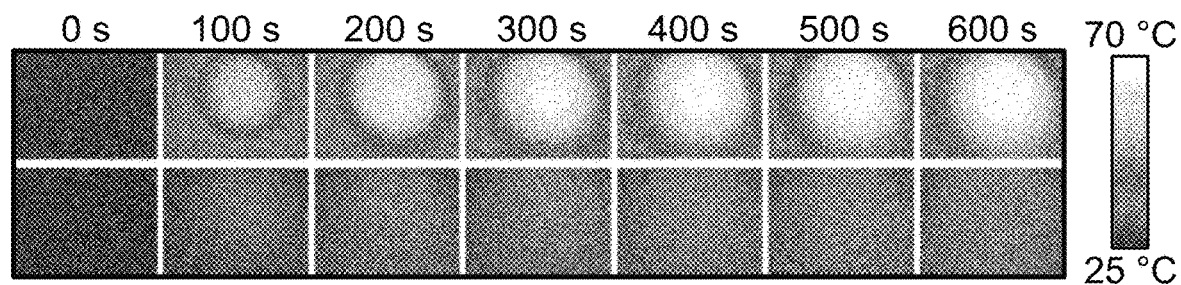
FIG. 15A is an exemplary embodiment of IR images showing the temperature of a wood-GO (top panel) and wood (bottom panel) under laser illumination in accordance with the present disclosure.
Figure 15B:
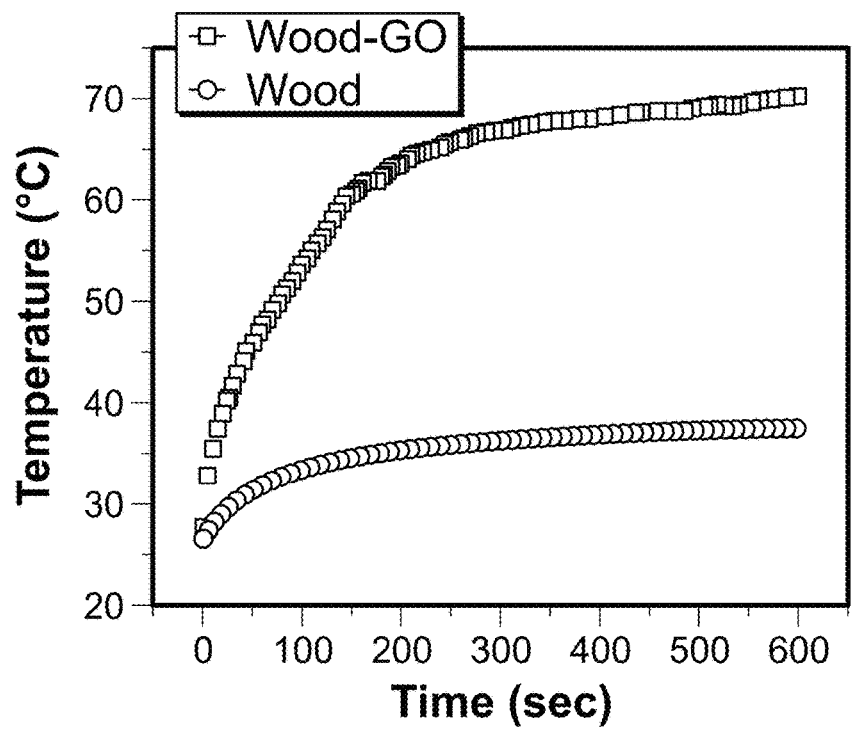
FIG. 15B is an exemplary embodiment of a plot showing the surface temperature of a wood-GO composite and wood under laser illumination in accordance with the present disclosure.

The photothermally induced temperature rise associated with wood and wood-GO under near-infrared (NIR) laser illumination (808 nm, power density of 5 $kW/m^2$) in a dry state (FIG. 15A) was investigated. Upon laser irradiation, the temperature of wood-GO rapidly increased from room temperature (27° C.) to around 70° C., while the temperature of wood reached around 37° C. under identical irradiation conditions (FIG. 15B). The large temperature rise of wood-GO ($\Delta T=43°$ C.) compared to the relatively small increase in the temperature of wood ($\Delta T=12°$ C.) upon laser irradiation demonstrates the high optical absorption and effective photothermal conversion efficiency of GO under NIR illumination.

Figure 15C:
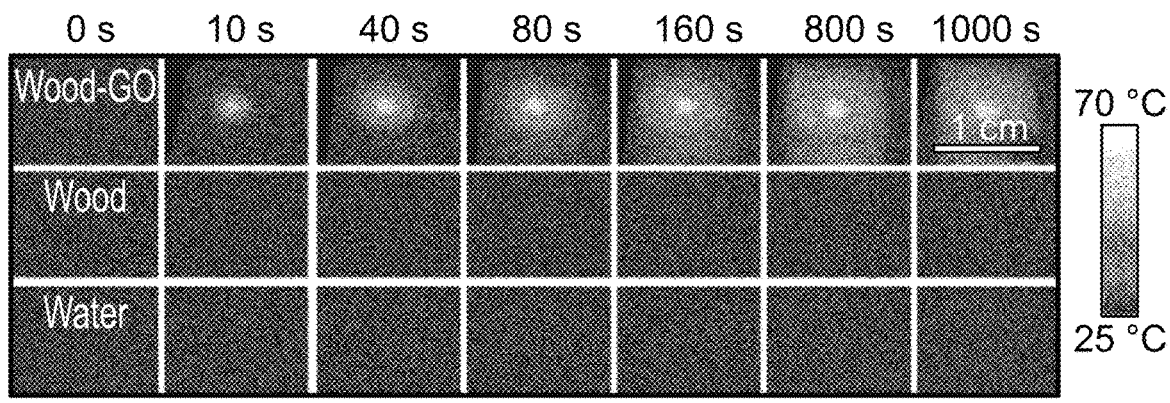
FIG. 15C is an exemplary embodiment of IR images of a wood-GO composite (top panel), wood (middle panel) and water under laser illumination in accordance with the present disclosure.
Figure 15D:
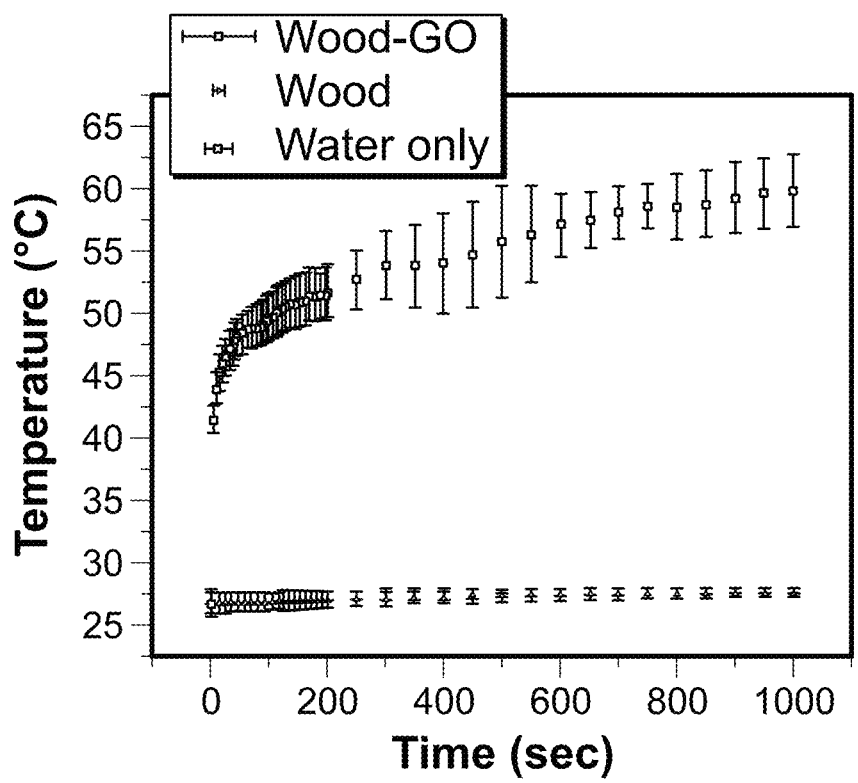
FIG. 15D is an exemplary embodiment of a plot showing the surface temperature of a wood-GO composite, wood and water under laser illumination in accordance with the present disclosure.
Figure 15E:
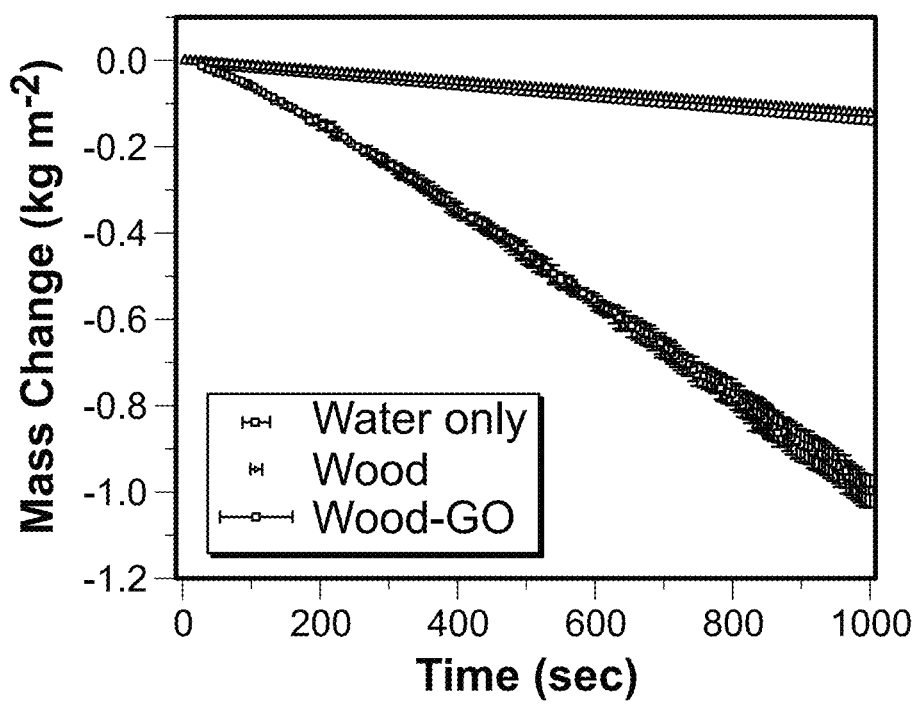
FIG. 15E is an exemplary embodiment of a plot showing cumulative mass change through water evaporation for a wood-GO composite, wood and water under laser illumination in accordance with the present disclosure.

Additionally, the photothermal activity of wood-GO in the wet state was investigated because the wood-GO composite is in a hydrated state during solar steam generation. IR images reveal the temperature of the wood and wood-GO floated on the surface of water under 808 nm laser illumination (power density of 5 $kW/m^2$) at various time points (FIG. 15C). Upon laser irradiation, the temperature of wood-GO floating on water rapidly increased from room temperature (27° C.) to around 60° C. (FIG. 15D). In comparison, the temperature of wood and water did not exhibit a significant increase within an irradiation time of 1000 sec (FIG. 15D). The mass change of water as a function of irradiation time was employed to quantify the steam generation efficiency of the wood-GO composite and wood. Over 1000 sec laser irradiation, the mass change of water from wood-GO floated on water was found to be around 1 kg/m², which is nearly seven times higher compared to that observed for wood on water (0.14 kg/m²) and water (0.12 kg/m²) (FIG. 15E). This was significantly higher steam generation efficiency of wood-GO composite compared to wood stems from the higher NIR light absorption of GO compared to wood, with the latter predominantly absorbing in the visible part of the electromagnetic spectrum (as shown in FIG. 13B).

Figure 16A:
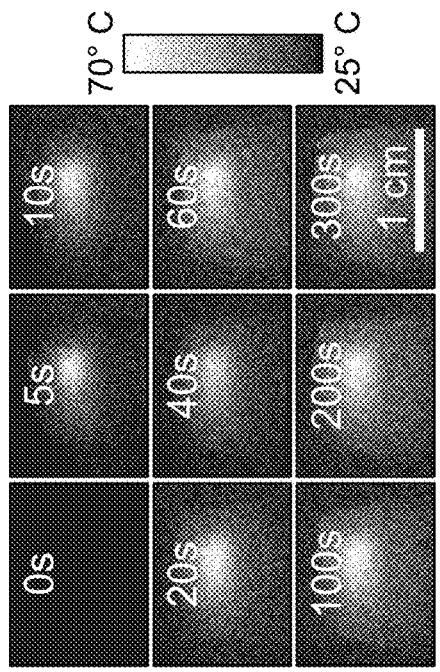
FIG. 16A is an exemplary embodiment of IR images showing the temperature of a wood-GO composite floated at an air/saline interface under solar illumination in accordance with the present disclosure.
Figure 16B:
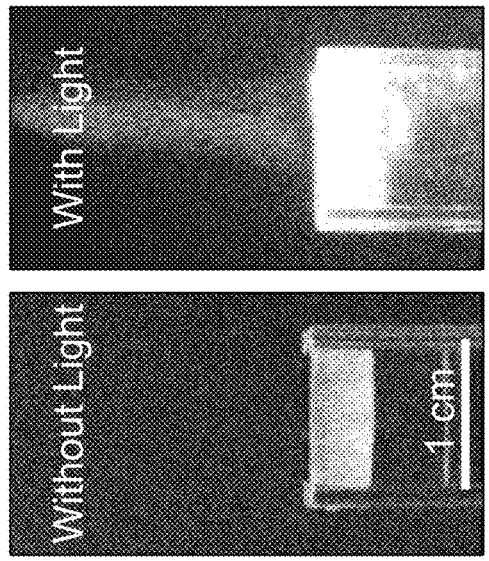
FIG. 16B is an exemplary embodiment of optical images of a wood-GO composite floated at an air/saline water interface and steam generation under solar illumination in accordance with the present disclosure.
Figure 16D:
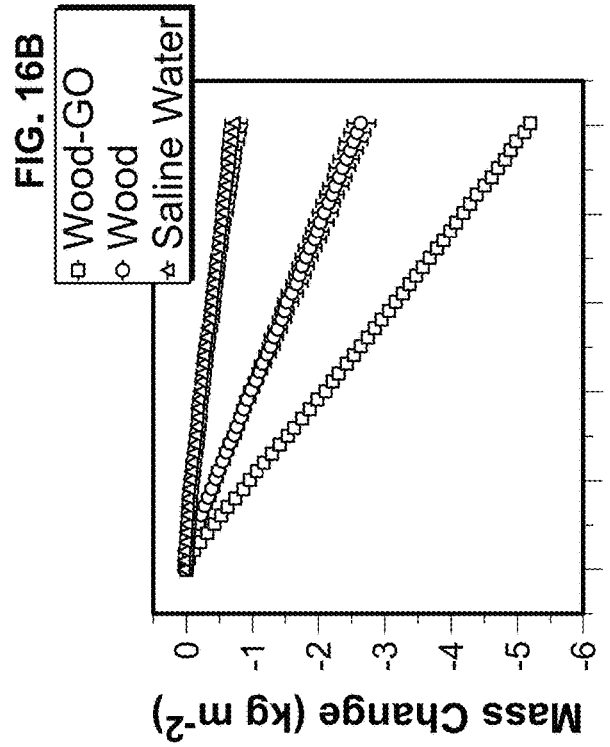
FIG. 16D is an exemplary embodiment of a plot showing cumulative mass change through water evaporation of a wood-GO composite, wood and saline water under solar illumination in accordance with the present disclosure.
Figure 16C:
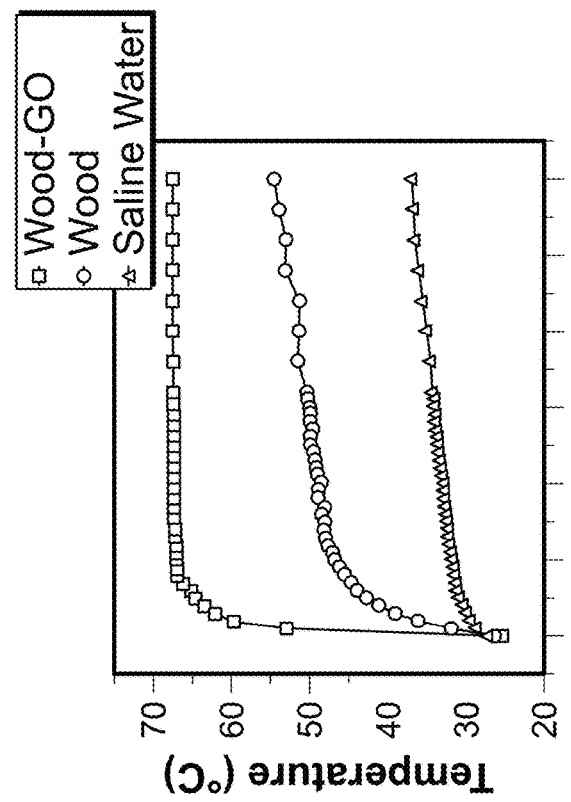
FIG. 16C is an exemplary embodiment of a plot showing the surface temperature of a wood-GO composite, wood and saline water under solar illumination in accordance with the present disclosure.

To evaluate the steam-generation efficiency and the desalination ability of wood-GO composite under simulated solar illumination (power density of 12 kW/m²), the weight loss of saline water due to the water evaporation (3% salinity) was measured (FIGS. 16A-16D). GO flakes exhibit a broad optical absorption over visible and NIR parts of the electromagnetic spectrum. Combined with the absorption of wood in the visible region, the large temperature rise of the wood-GO composite under simulated solar illumination resulted in the appearance of steam above the cuvette, which signifies the rapid evaporation of water (FIGS. 16A, 16B). The temperature of the wood-GO composite rapidly increased from room temperature to around 67° C. within tens of seconds after the onset of simulated solar irradiation and remained constant over the remaining irradiation time (FIG. 16C). In the case of pristine wood (i.e. in the absence of GO layer), the temperature raised from 27° C. to 54° C. Compared to 808 nm laser, the larger temperature rise for pristine wood under simulated solar illumination may be attributed to the higher optical absorption of wood in the visible part of the electromagnetic spectrum that exhibits a large significant overlap with the solar spectrum. On the other hand, the temperature rise of saline water itself was found to be significantly smaller ($\Delta T=\sim 10°$ C.).

Under solar illumination, the cumulative weight loss was found to increase linearly with the irradiation time (FIG. 16D). The weight loss over a duration of 1000 s was found to be 5.2 kg/m² for wood-GO composite. Over 200 s of solar irradiation, the steady-state evaporation rate was calculated to be 14.02 kg/m²·h for wood-GO composite. In the case of pristine wood, the steady-state evaporation rate was calculated to be 10.08 kg/m²·h. Without considering the optical concentration losses in the analysis, such as surface radiation and reflection, the evaporation efficiency of the wood-GO composite was calculated to be 82.8% at a power density of 12 kW/m². In the case of pristine wood, the evaporation efficiency was found to be around 59.5%. These results demonstrate the excellent photothermal capabilities of wood-GO composite and its application in solar steam generation.

Figure 17A:
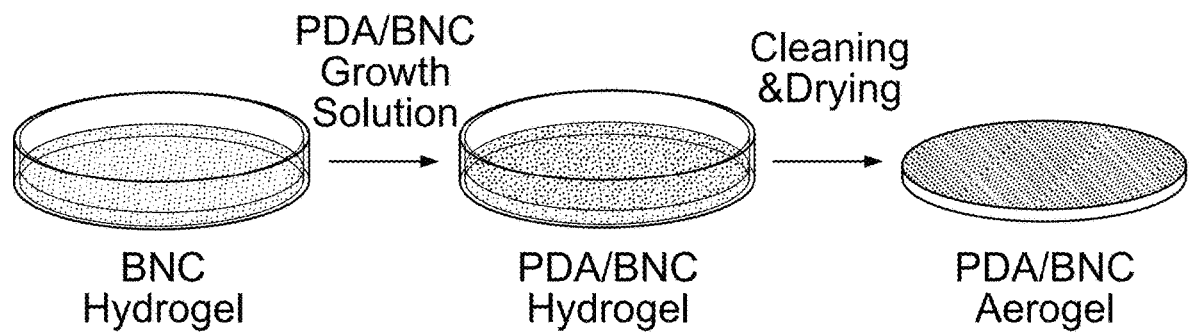
FIG. 17A illustrates the fabrication of a PDA/BNC hydrogel.
Figure 17B:
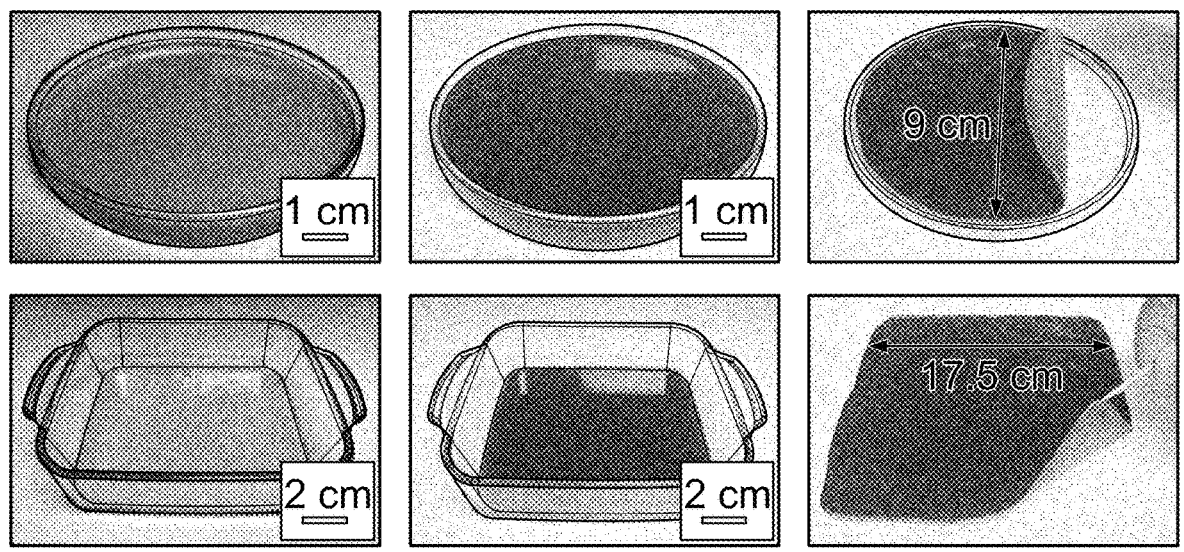
FIG. 17B illustrates the PDA/BNC hydrogel with tunable sizes and shapes.
Figure 18A:
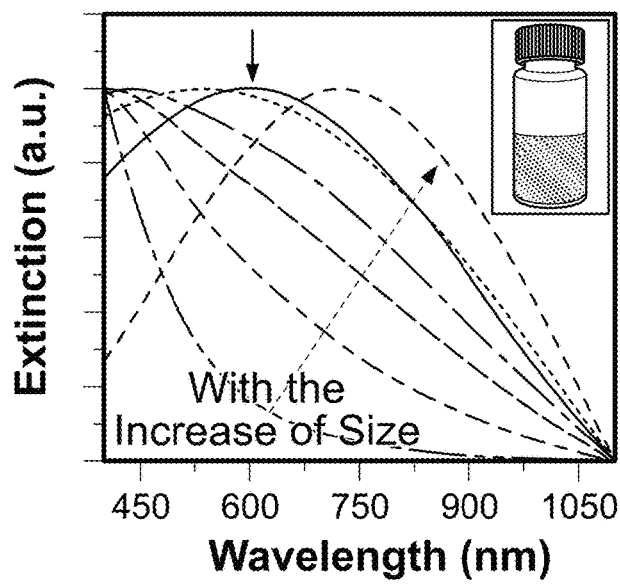
FIG. 18A is the Vis-NIR extinction spectra of PDA particles with varying sizes (inset is the photograph of PDA particles solution.
Figure 18B:
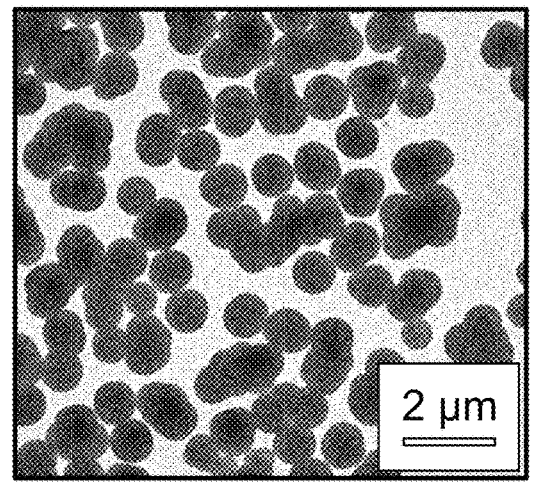
FIG. 18B is the TEM image of PDA particles.
Figure 18C:
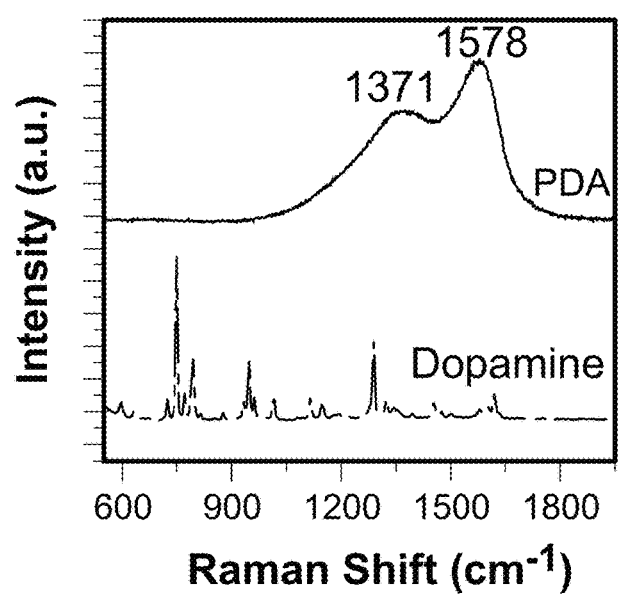
FIG. 18C is the Raman spectra of Dopamine and PDA.
Figure 18D:
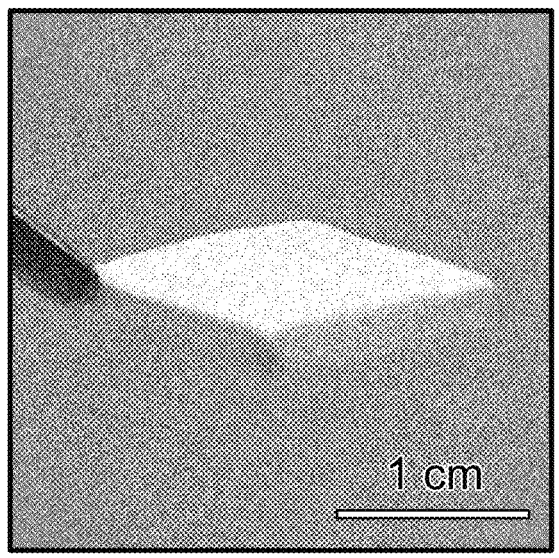
FIGS. 18D and 18E are optical and SEM images of the surface (inset is the image of higher resolution) and cross-section (FIG. 18F) of a pristine BNC foam.

In yet another aspect, the fabrication of and interfacial solar steam generator with desired size and shape involves a two-step BNC growth under aerobic and static growth conditions (FIG. 17 and Example 8). PDA particles were obtained using a method reported by Lu and co-workers, infra, through oxidation and self-polymerization of dopamine monomers in a mixture of water, ethanol and ammonia at room temperature. The size of PDA particles, which alters the optical properties, was tuned by varying the ratio of ammonia to dopamine monomers. The size of the PDA particles was optimized to efficiently trap PDA particles within the BNC fiber matrix and to ensure significant overlap between the optical absorption of the PDA particles and the solar spectrum in the visible and near infrared region (FIG. 18A). Transmission electron microscopy (TEM) and scanning electron microscopy (SEM) images revealed that the PDA particles were spherical in shape with a diameter of ~1 μm (FIG. 18B). Dynamic light scattering (DLS) also revealed the hydrodynamic size of the PDA particles to be ~1 μm. Raman spectrum of dopamine monomers showed characteristic bands of C—C stretching (724, 948, 1324, and 1422 cm-1), C—O stretching (1290 cm-1), and C—N stretching (795 cm-1). The Raman spectrum of PDA particles exhibited two broad bands (1371 and 1578 cm-1), suggesting catechol deformation. This provides an additional confirmation of successful PDA particles synthesis (FIG. 18C).

Figure 18E:
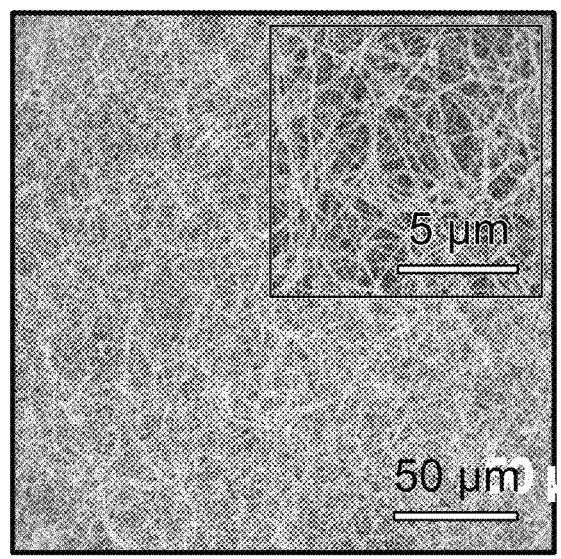
Figure 18F:
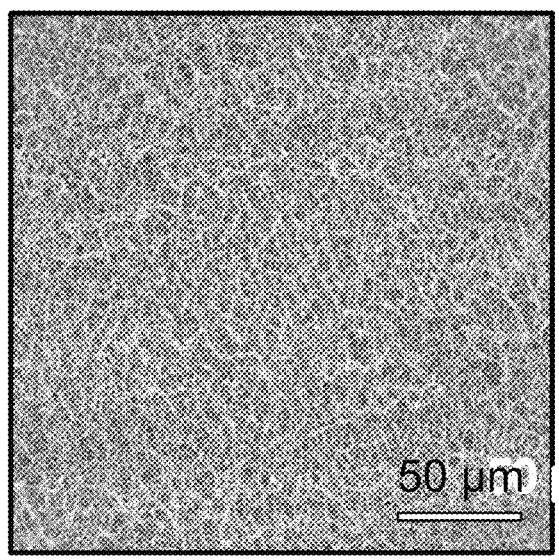
FIGS. 18G and 18H are optical and SEM images of the surface (inset is the image of higher magnification) and cross-section (FIG. 18I) of a PDA/BNC foam.
Figure 18G:
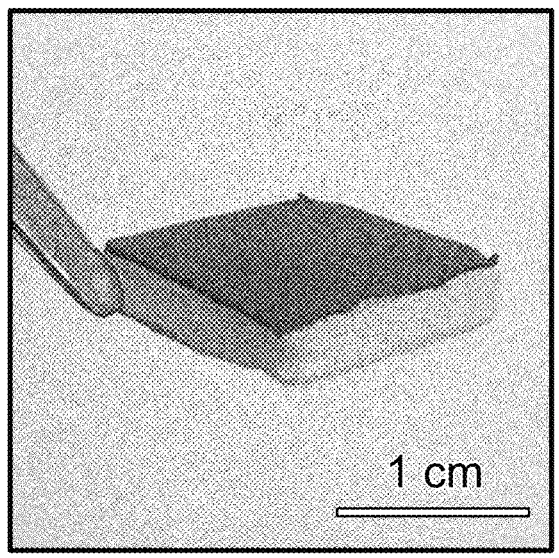
Figure 18H:
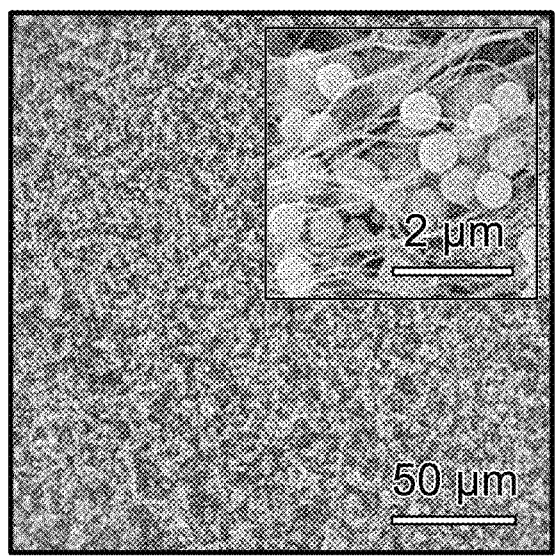
Figure 18I:
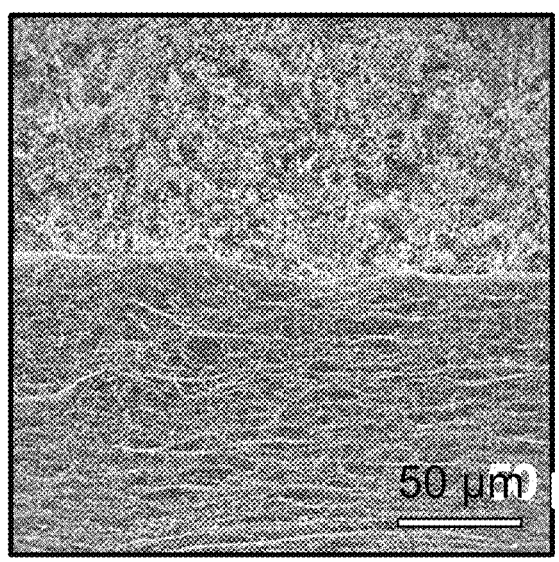
Figure 19A:
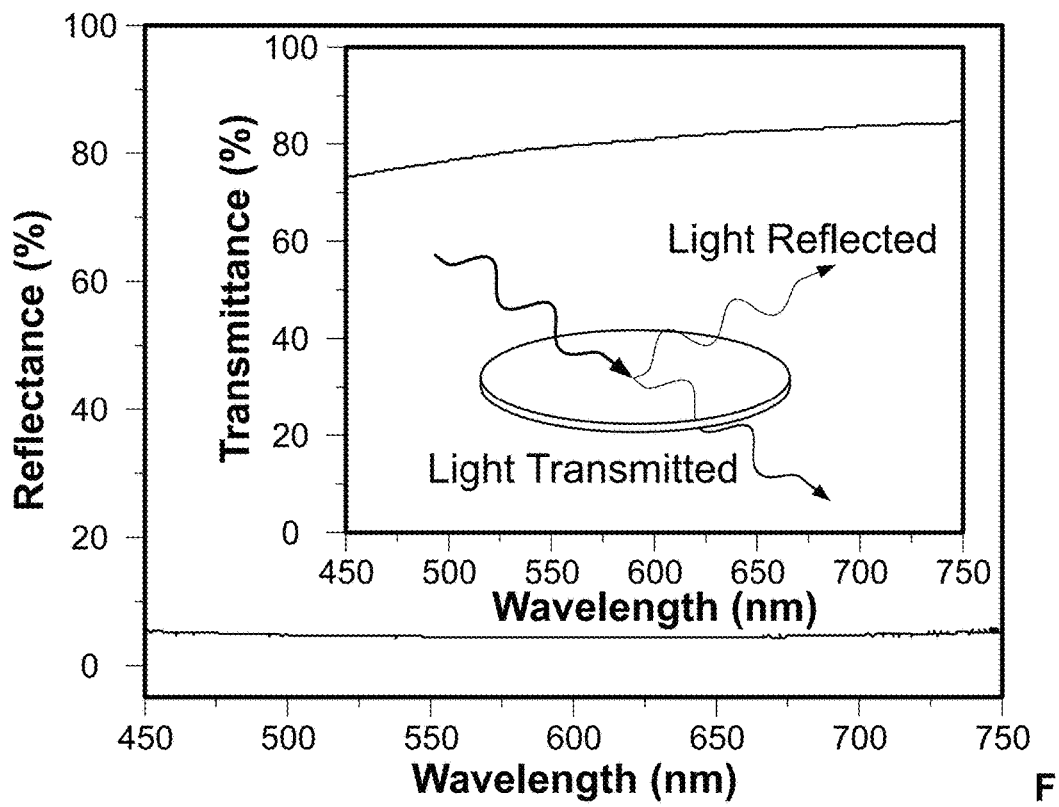
FIG. 19A is the transmittance and reflectance spectra of a BNC hydrogel.
Figure 19B:
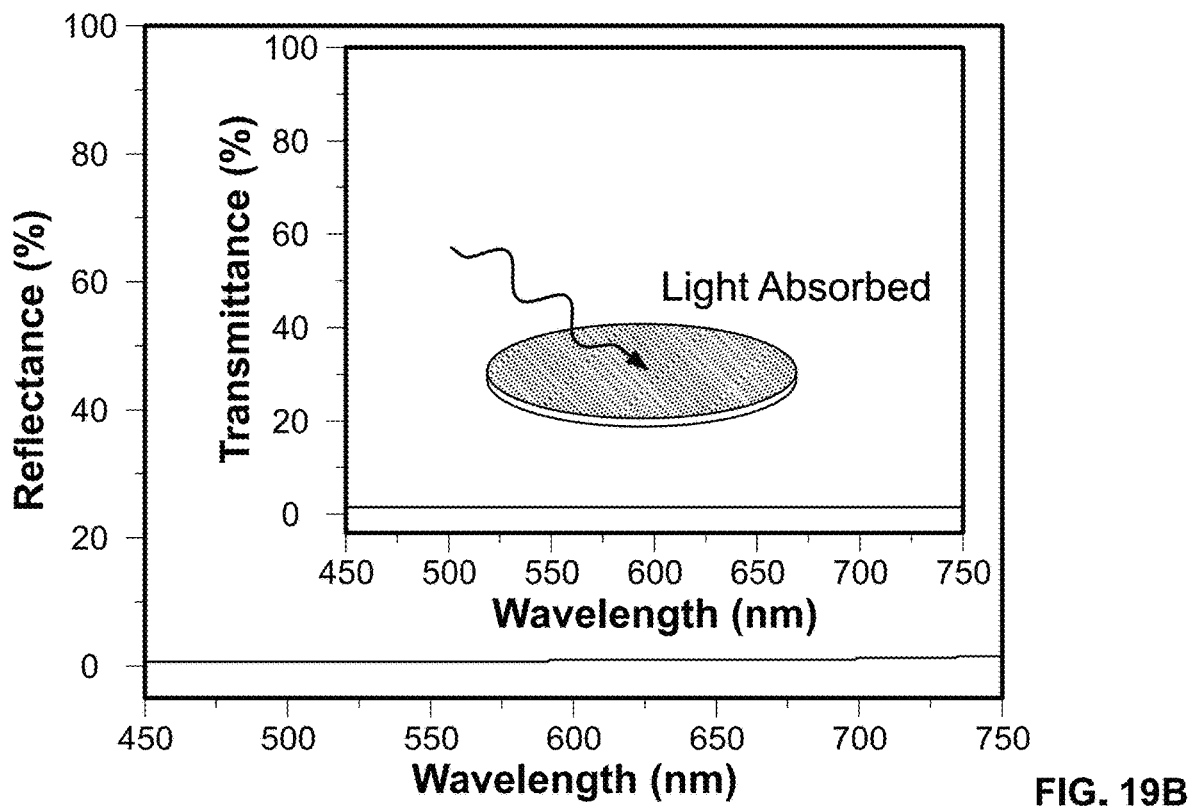
FIG. 19B is the transmittance and reflectance spectra of a PDA/BNC hydrogel.
Figure 19C:
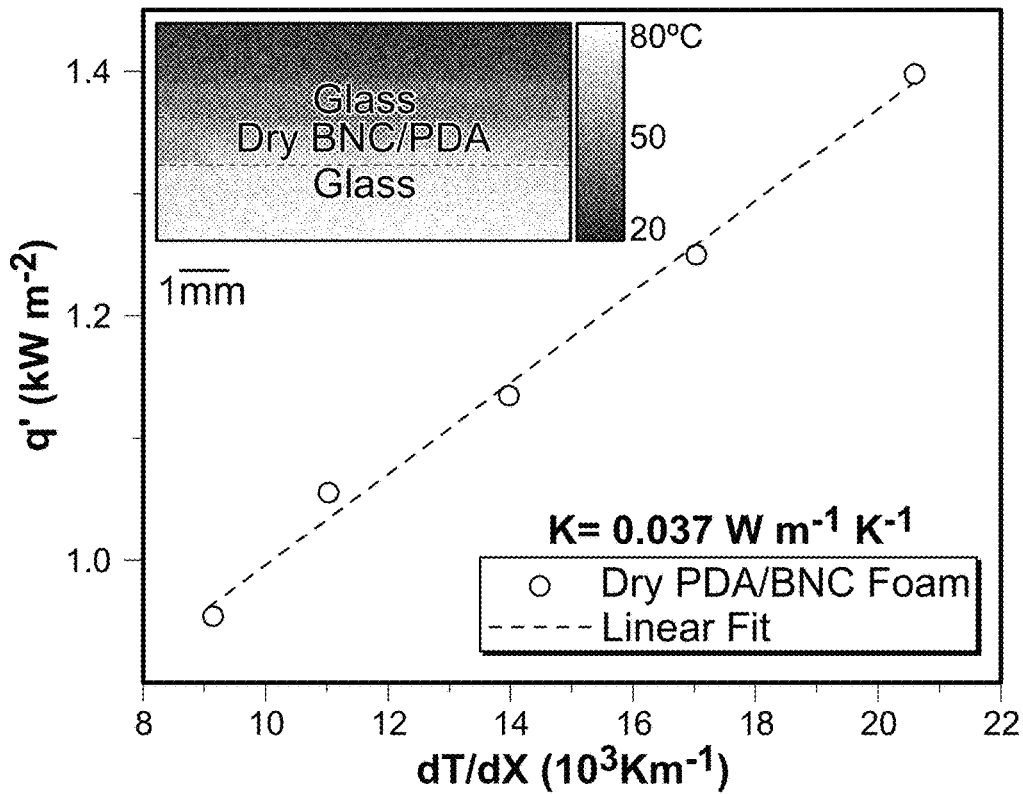
FIGS. 19C and 19D are the thermal conductivities of dry PDA/BNC foam and wet PDA/BNC hydrogel. Insets in FIGS. 19C and 19D are representative IR images showing the temperature gradient along the thickness of the samples.
Figure 19D:
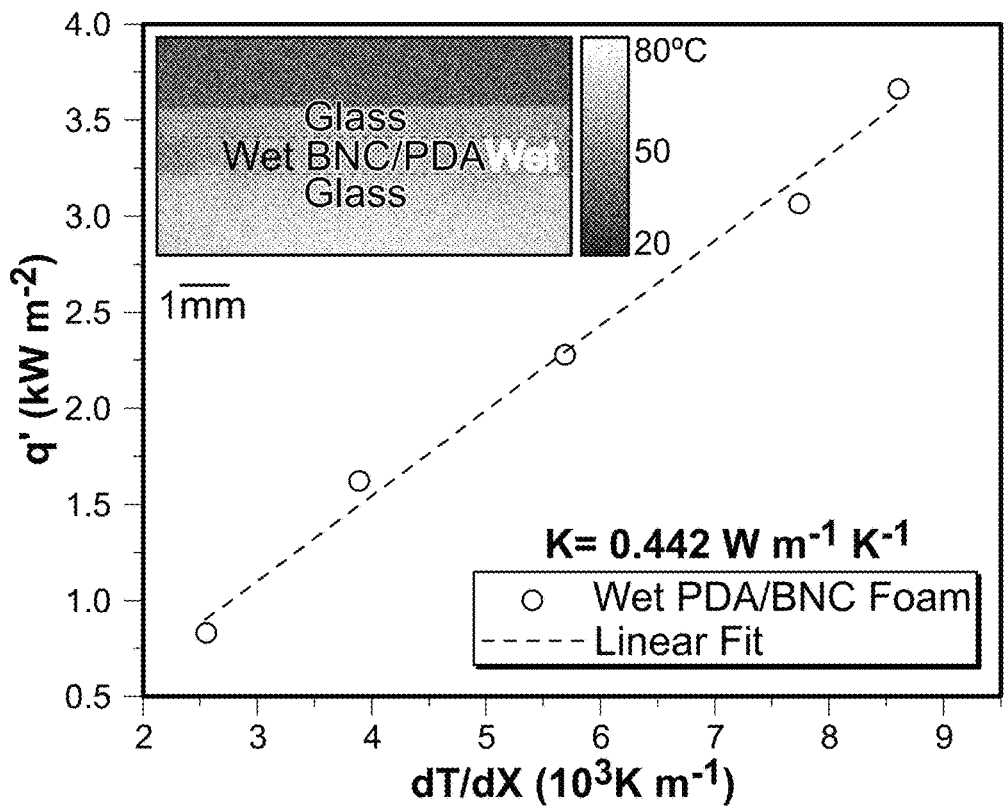
Figure 23:
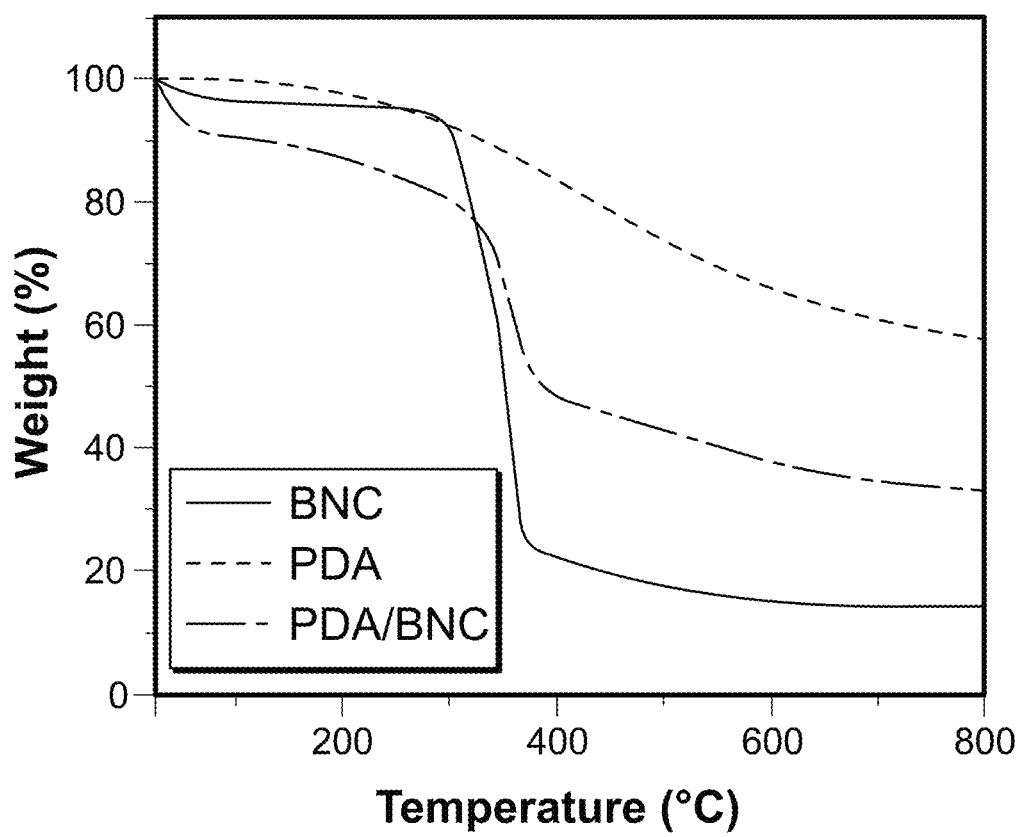
FIG. 23 is the thermogravimetric analysis of pristine BNC, pristine PDA, and PDA/BNC.
Figure 24A:
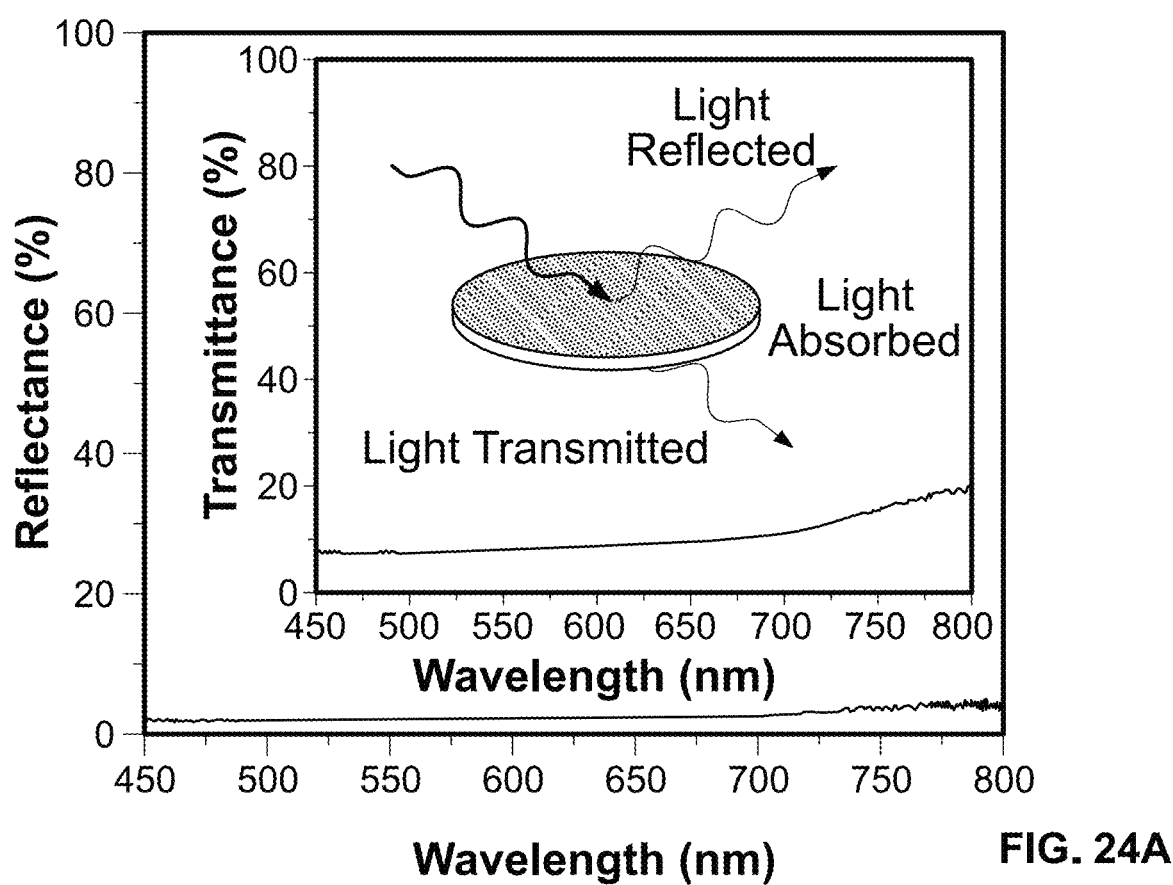
FIG. 24A is the transmittance and reflectance spectra of PDA coated BNC hydrogel.
Figure 24B:
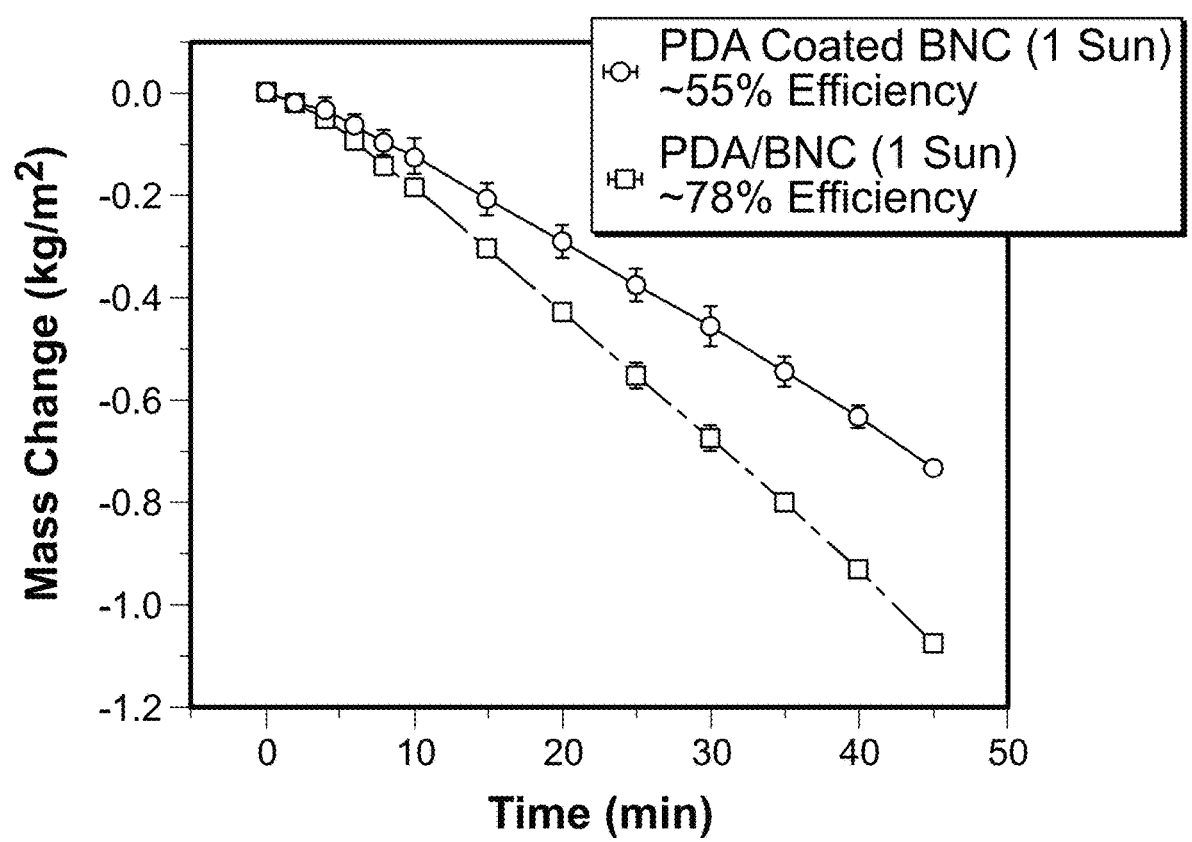
FIG. 24B is a graph of the solar steam generation performance of PDA-coated BNC compared with PDA/BNC via in situ growth method.

Pristine BNC aerogel exhibited ~98% porosity, ultralow density (~20 kg/m³) and extremely large specific surface area (FIG. 19D). Furthermore, BNC aerogel forms a highly open microporous non-woven 3D network of cellulose nanofibrils (diameter of 20-100 nm) with highly abundant hydroxyl groups, promoting high hydrophilicity (FIG. 18E, FIG. 18F). Thus, the nature of the BNC aerogel facilitates the transport of water to the evaporative surface, making it as an ideal supporting material for an interfacial solar steam generator. The bilayered structure of PDA/BNC was achieved by growing a thin BNC layer (~100 μm) with PDA particles on top of a thick pristine BNC hydrogel (~4 mm, as a heat insulation and water transport layer) (FIG. 18G). As the bacteria produces a dense entangled layer of cellulose fiber network at the air/bacteria-growth medium interface, the high density of PDA particles may be loaded within the top layer, as shown in the surface and cross-sectional SEM images (FIG. 18H, FIG. 18I). A cross-sectional SEM image also shows the sharp interface between the PDA-loaded and pristine BNC layers. Thermogravimetric analysis determined that the loading of PDA particles to be around 43% (FIG. 23).

To evaluate the light absorption properties of PDA/BNC, the optical transmittance and reflectance of BNC and PDA/BNC was measured. Pristine BNC hydrogel (~4 mm) showed high transmittance (~80%) and reflectance (~4.8%) in the visible region, which translates to relatively small light extinction (~15.2%) (FIG. 19A). On the other hand, the PDA/BNC hydrogel (with thickness of ~4.1 mm) exhibited extremely small optical transmittance (~1.2%) and reflectance (~0.96%) in the visible region, indicating a large optical extinction (~98%) of the bilayer (FIG. 19B). The large light extinction of the PDA/BNC results from the light absorption corresponding to the densely loaded PDA particles and the light scattering from the nanoscale cellulose fibers, which increases the optical path length within the bilayer.

PDA adheres to a broad range of materials with widely different surface chemistries. It is possible to coat PDA on BNC via self-polymerization under oxidative condition in order to prepare a PDA/BNC interfacial solar evaporator. After five polymerization cycles (each for over 12 hours), the PDA/BNC hydrogel exhibited a light extinction of ~87% (FIG. 23). The coating process via polymerization results in a thin layer of PDA on the nanofibers of the highly porous BNC. The lower amount of PDA in the PDA-coated BNC compared to that in PDA particle-filled BNC results in a lower light extinction of the former compared to the latter.

Figure 20A:
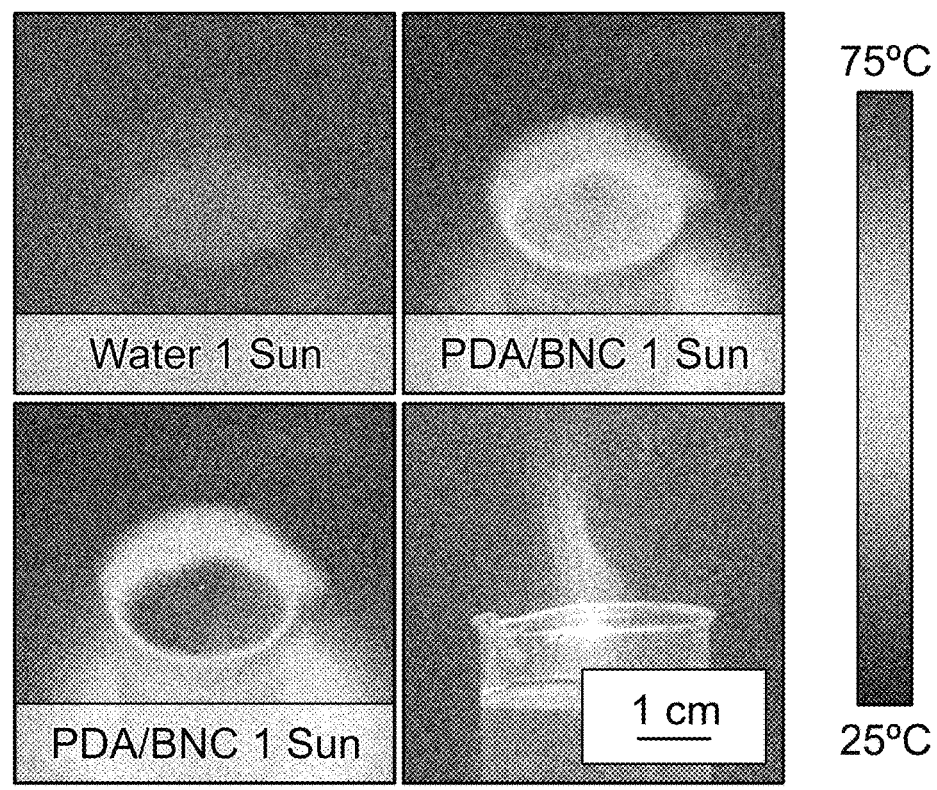
FIG. 20A illustrates IR images of water under 1 kW/m² solar irradiation, PDA/BNC under 1 kW/m² and 3 kW/m² solar irradiation and optical image, showing visible steam generation under 3 kW/m².
Figure 20B:
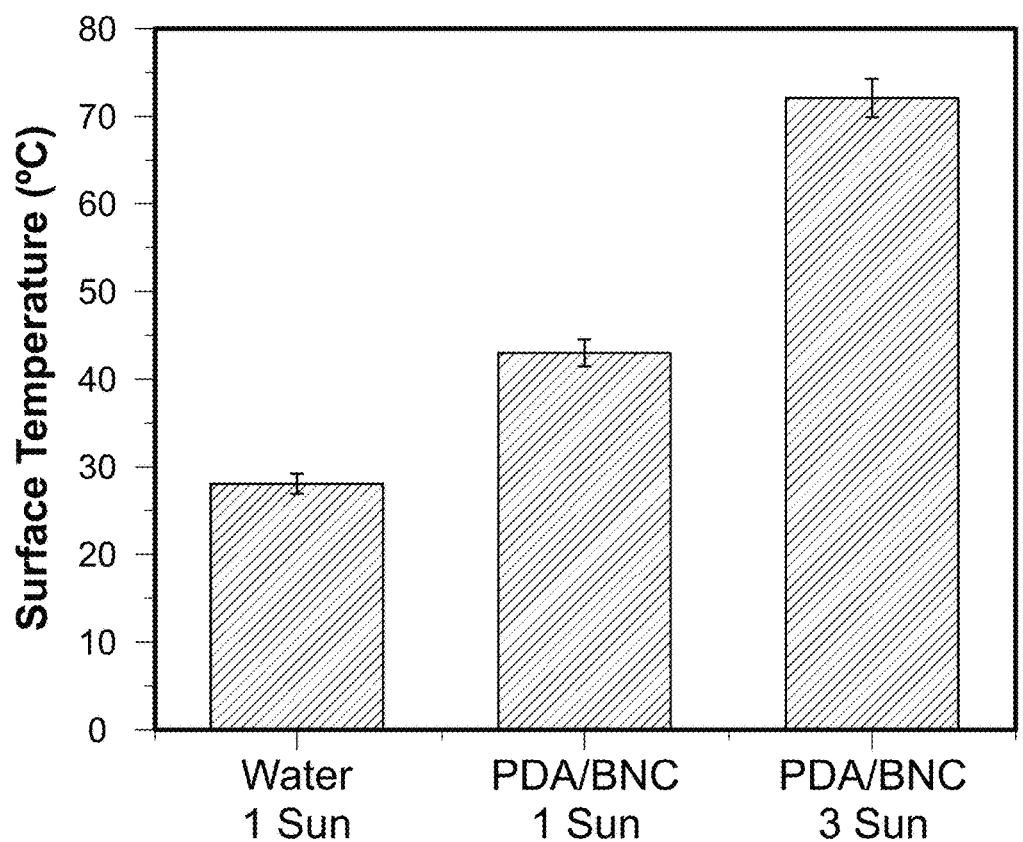
FIG. 20B is a graph of the surface temperatures of water and PDA/BNC foam under 1 and 3 kW/m² irradiations.

The solar steam generation performance of the PDA/BNC under 1 kW/m² (approximately one sun) and kW/m² (approximately three sun) was evaluated. IR imaging was employed to monitor the temperature rise in the PDA/BNC floated at air/water interface upon irradiation with a simulated solar beam (power density of 1 kW/m² or 3 kW/m²). Upon irradiation, the temperature of the PDA/BNC rapidly increased from room temperature (25° C.) to ~4° C. (3 kW/m²) and to ~72° C. (kW/m²) (FIGS. 20A,20 B). The temperature rise of water in the absence of PDA/BNC layer was only 2-4° C. The large rise in temperature of PDA/BNC film under 3 kW/m² illumination resulted in the appearance of steam above the 100-mL beaker, evidencing the rapid evaporation of water (FIG. 20A).

Figure 20C:
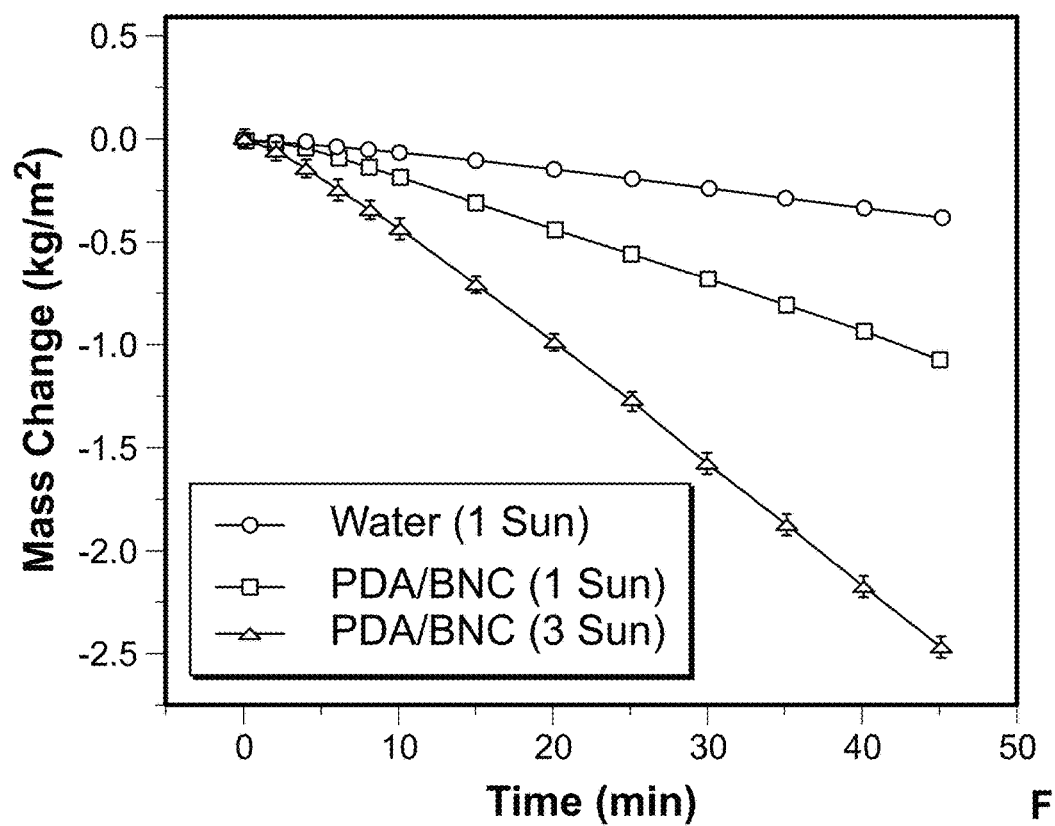
FIG. 20C is a plot showing the cumulative weight losses through water evaporation of water and PDA/BNC foam under different solar irradiations.
Figure 20D:
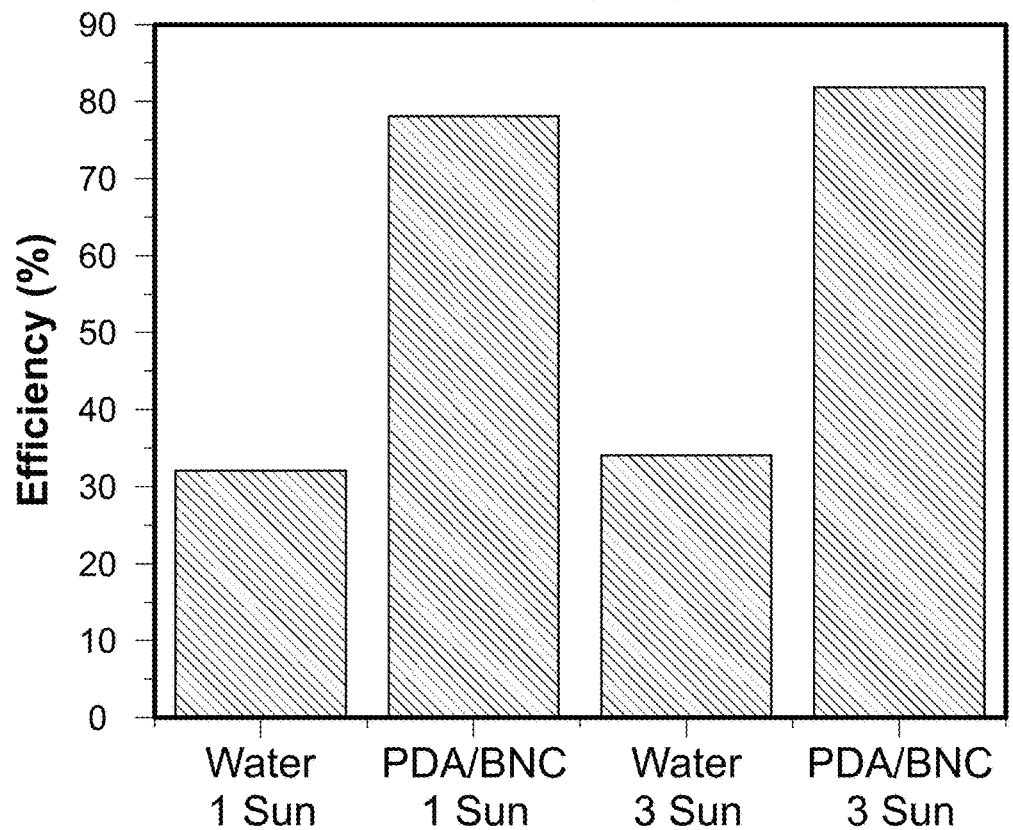
FIG. 20D compares the steam generation efficiencies of water and PDA/BNC foam under different solar irradiations.

The efficiency of the PDA/BNC interfacial evaporator was quantified by measuring the weight loss (due to water evaporation) as a function of irradiation time (all tests were performed for 45 min). The cumulative weight loss increased linearly with irradiation time (FIG. 20C). Under one sun irradiation, the evaporation rate was 1.13 kg/m²·h. In the absence of the PDA/BNC steam generator, the evaporation rate of water under identical irradiation was 0.46 kg/m²·h. The steady state evaporation rate under 3 kW/m² with PDA/BNC is 3 kg/m²·h. In the tested embodiment, the evaporation efficiency of PDA/BNC was calculated to be 78% under one sun. The evaporation efficiency of unaided water is only 32% due to the poor photothermal conversion and the large energy loss associated with bulk water heating. With increasing solar power density, the evaporation efficiency increased to 82% under 3 kW/m² (FIG. 20D).

Figure 21A:
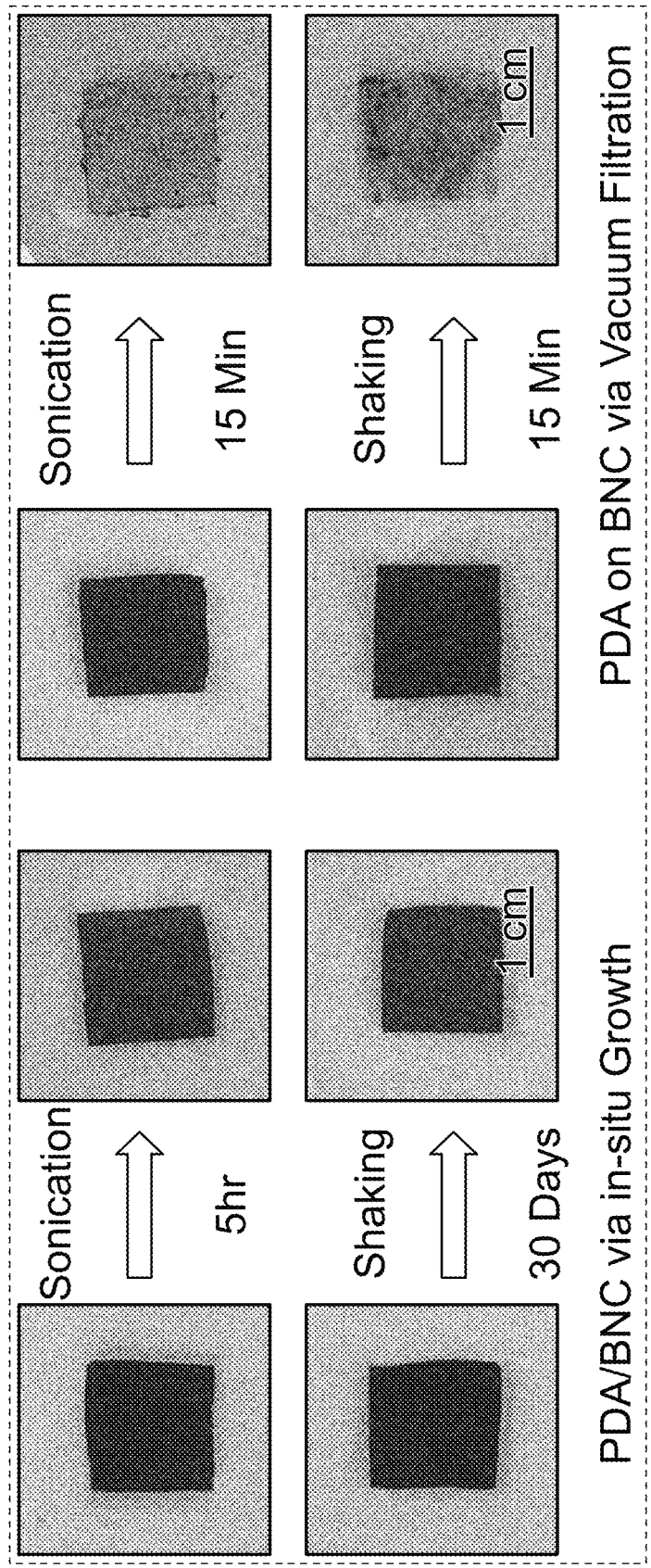
FIG. 21A is optical images of PDA/BNC foam achieved via in situ growth and vacuum filtration that have been subjected to sonication and shaking for extended duration.
Figure 21B:
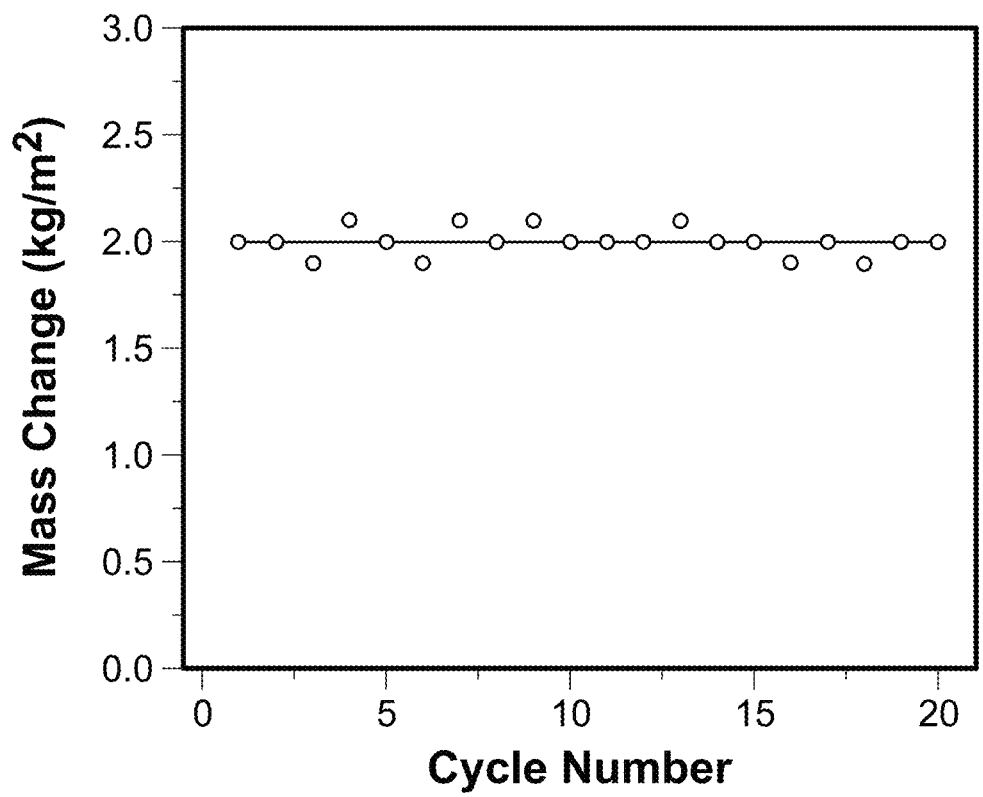
FIG. 21B graphs the cycling of solar steam generation tests under 7 kW/m² solar irradiation for 15 min over 20 cycles.
Figure 21C:
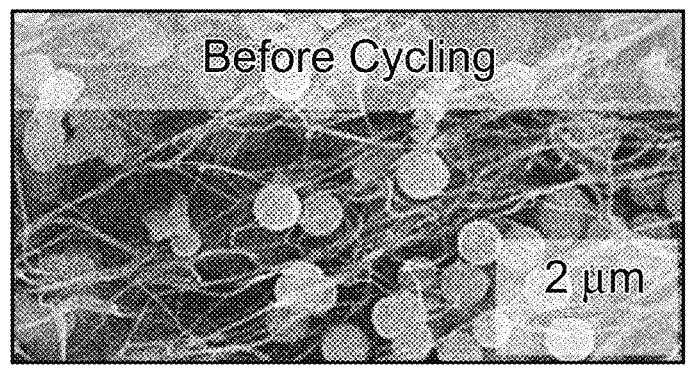
FIG. 21C is high-resolution SEM images of the PDA/BNC surface before and after 20 cycles of solar steam generation depicting the intact structure of the PDA/BNC foam.
Figure 21C:
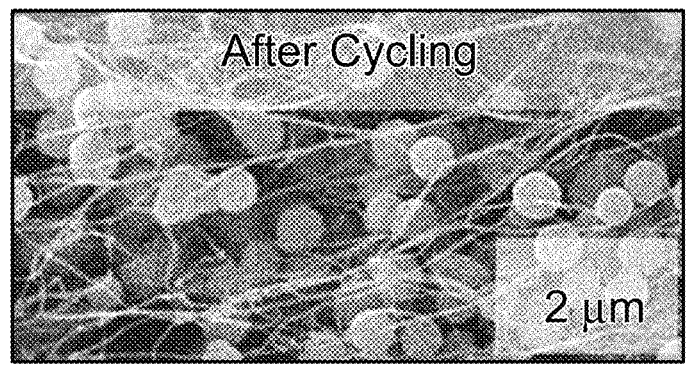
Figure 22A:
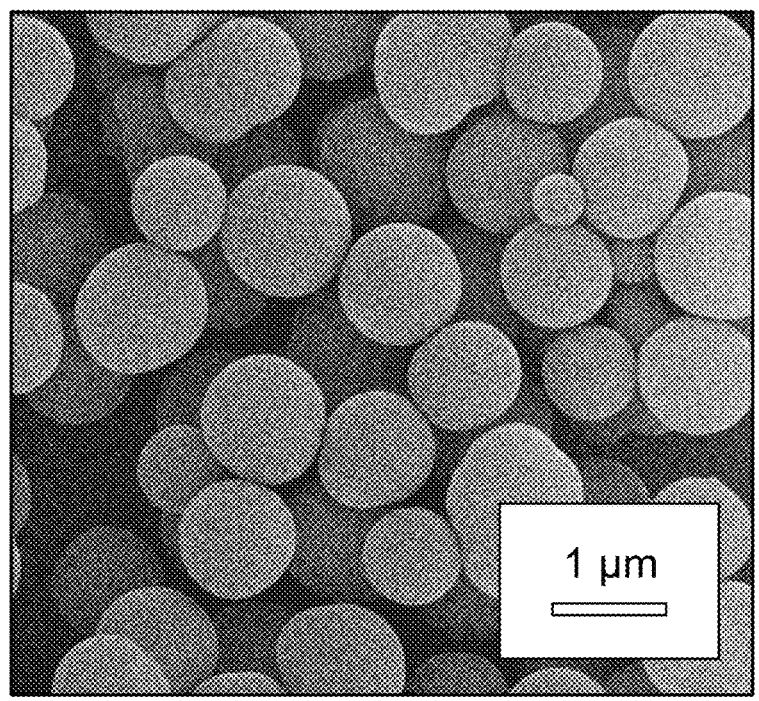
FIG. 22A is an SEM image of PDA particles.
Figure 22B:
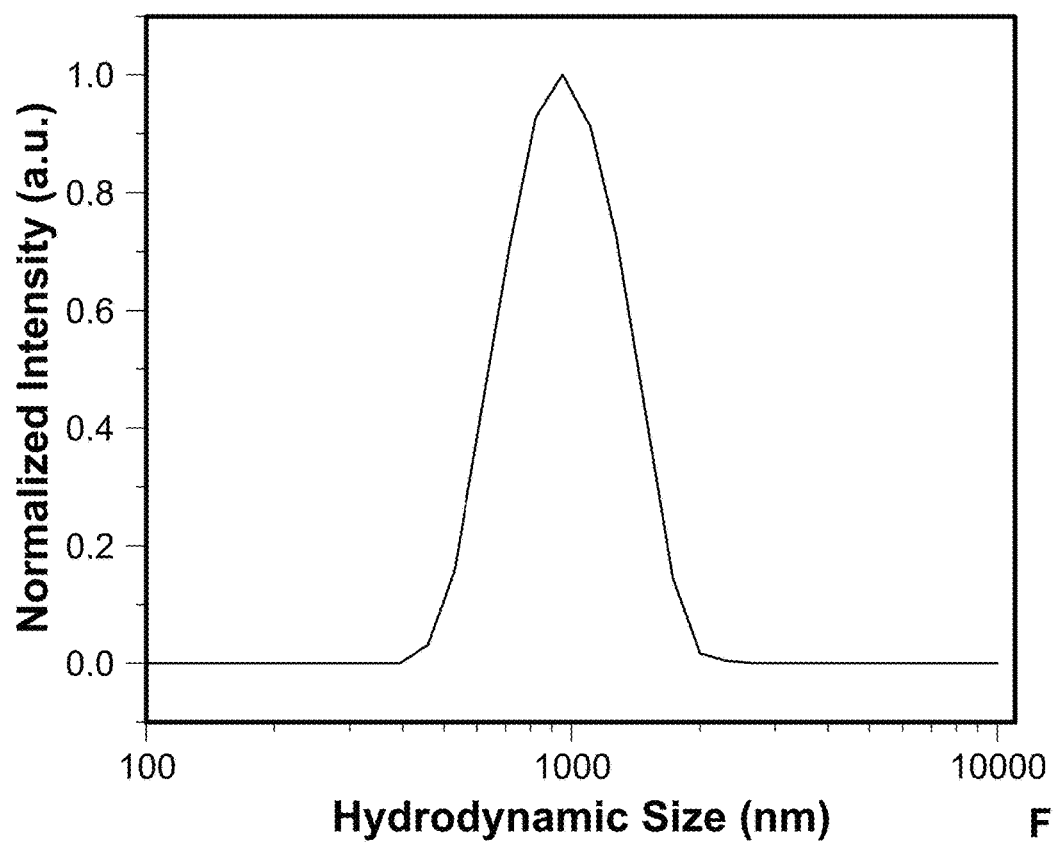
FIG. 22B is a graph of the hydrodynamic size of PDA particles measured by DLS.

To test the robustness of the PDA/BNC foam, it was subjected to rigorous mechanical agitation and boiling for 2 hours during a cleaning procedure to remove the bacteria and culture medium residue. Despite the strong mechanical agitation, the tested embodiment did not exhibit any signs of disintegration or loss of PDA particles. To further test its stability, the PDA/BNC was subjected to ultrasonic agitation (483 W) for 5 hours with vigorous shaking for 30 days. The membrane did not exhibit any signs of disintegration or loss of PDA particles (FIG. 21A, left part). The robustness of the PDA/BNC solar steam generator allows for reuse multiple times without any noticeable degradation of the structure or steam generation ability. Over 20 cycles of reuse, the steady-state evaporation rate and cumulative weight loss over 15 min irradiations (even under a higher power density, 7 kW/m²) was found to exhibit less than 6% variation (FIG. 21B). The structure of the PDA/BNC evaporator remained unaltered after cycling tests (involving around 5 h high temperature solar exposure), which is evident from SEM images of the PDA/BNC surface before and after cycling (FIG. 21C). TGA results also suggested the excellent thermal stability of BNC (up to 280° C.) and PDA (with 58% left up to 800° C.).

The thermal conductivity of interfacial solar evaporator plays a key role in confining the heat to the evaporative surface so the thermal conductivity of the PDA/BNC under both dry and wet conditions was tested. PDA/BNC samples were sandwiched between two glass slides maintained at different temperatures at both ends. The gradient in the temperature along the thickness of samples was observed using an IR camera (insets of FIG. 19C, 19D). The thermal conductivity of dry PDA/BNC (0.037 W/m·K) is just slightly higher than air (FIG. 19C). The low thermal conductivity of dry PDA/BNC owes to the large porosity (i.e., filled with air pockets with a thermal conductivity of 0.024 W/m·K at room temperature) of the structure. Wet PDA/BNC exhibited a thermal conductivity (0.442 W/m·K) lower than water (0.600 W/m·K at room temperature) (FIG. 19D).

EXAMPLES

The following Examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Examples.

Example 1: Preparation of RGO/BNC Aerogel

*Gluconacetobacter hansenii* (ATCC 53582) was cultured in test tubes containing 16 mL of #1765 medium at 30° C. under shaking at 250 rpm. The #1765 medium was composed of 2% (w/v) glucose, 0.5% (w/v) yeast extract, 0.5% (w/v) peptone, 0.27% (w/v) disodium phosphate, and 0.5% (w/v) citric acid. Graphene oxide was synthesized using methods known in the art. Graphene oxide solution (28 mL of 0.1 wt. %) was centrifuged and redispersed in #1765 medium and then centrifuged again to leave a wet mixture of GO and medium after decanting supernatant. Bacterial culture solution (incubated 3 d) was added to the GO/medium wet mixture to make it to a total 7 mL (with GO concentration of 0.4 wt. %). The solution was subsequently transferred to a Petri dish and incubated at room temperature without disturbance. After 5 d, a thin film of GO/BNC was formed at the liquid/air interface. Subsequently, 7 mL of bacterial growth solution was added on top of the GO/BNC film. After another 5 d, a bilayer of BNC and GO/BNC film was formed. For purification, the film was harvested from the Petri dish and washed in a 500 mL of 0.1 M NaOH aqueous solution under boiling conditions for 2 h. The obtained RGO/BNC:BNC hydrogel was then dialyzed in nanopure water for 2 d. The purified RGO/BNC:BNC hydrogel was then cut into desired dimensions, typically 1 cm×1 cm with a thickness of 2.1 mm, and then freeze-dried for 12 h.

Microstructure Characterization and Properties Measurements

SEM images were obtained using a FEI Nova 2300 field-emission scanning electron microscope at an acceleration voltage of 10 kV. AFM images were obtained using Dimension 3000 (Bruker Inc.) in light tapping mode. A Shimadzu UV-1800 spectrophotometer was employed for collecting the UV-vis extinction spectra in transmission mode. The Raman spectra were obtained using a Renishaw inVia confocal Raman spectrometer mounted on a Leica microscope with a 20× objective and a 514 nm wavelength diode laser as an illumination source. The FTIR spectra were recorded using a Nicolette Nexus 470 spectrometer. XPS analysis was performed using a Physical Electronics 5000 VersaProbe II Scanning ESCA (XPS) Microprobe. The specific surface areas of the GO/BNC bilayer aerogel were measured by the Brunauer-Emmett-Teller method using an Autosorb-1C (AX1C-MP-LP) at 298 K.

Thermogravimetric Analysis (TGA) to Measure RGO Loading in RGO/BNC:BNC

TGA was used to measure the weight fraction of RGO in the RGO/BNC:BNC structure. TGA was performed for both BNC film and the air-dried RGO/BNC:BNC bilayer film. The BNC film showed an initial mass loss (2-3%) at 100° C., which was attributed to absorbed water, a mass loss (~70%) at ~280° C. due to the degradation of the cellulose and a mass loss (~25%) at ~390° C. due to the decomposition of the cellulose residual, which generated $CO_2$ and $H_2O$. In the case of RGO/BNC:BNC, the initial mass loss (~2%) at ~100° C. was due to the loss of absorbed water, the second mass loss (~3%) at ~200° C. was due to the decomposition of functional groups of GO, the third mass loss (~52%) at 280° C. was due to the degradation of cellulose, and the final mass loss (~40%) at 390° C. was due to the decomposition of the cellulose residual and sublimation or burning of the damaged graphitic regions. Based on the TGA results, the mass loading of RGO in RGO/BNC:BNC was calculated to be ~27 wt. %.

Example 2: Stability of RGO/BNC:BNC

As the RGO/BNC:BNC hydrogel was base-washed during cleaning, it proved its stability in strongly basic environments. For the stability in an acidic environment, one RGO/BNC:BNC hydrogel was put in a Petri dish filled with pH 1.5 solution and sonicated for 1 h and the hydrogel was still intact.

Example 3: Reduction of GO to RGO

Figure 3C:
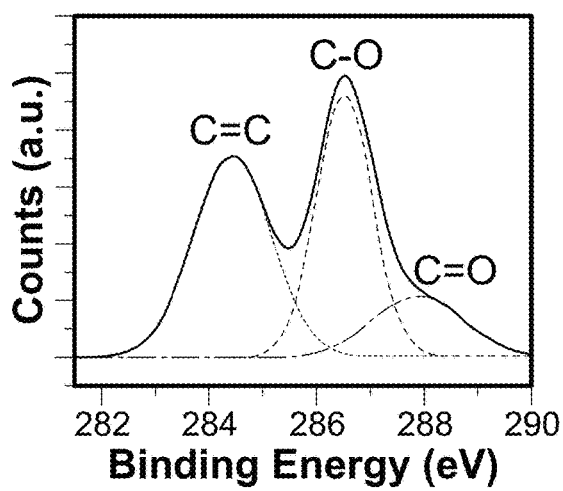
FIG. 3C is an exemplary embodiment of an XPS spectrum of pristine GO in accordance with the present disclosure.
Figure 3D:
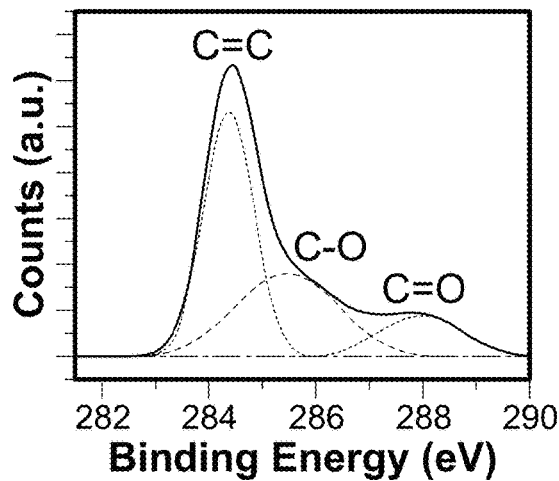
FIG. 3D is an exemplary embodiment of an XPS spectrum of base-washed RGO in accordance with the present disclosure.
Figure 3E:
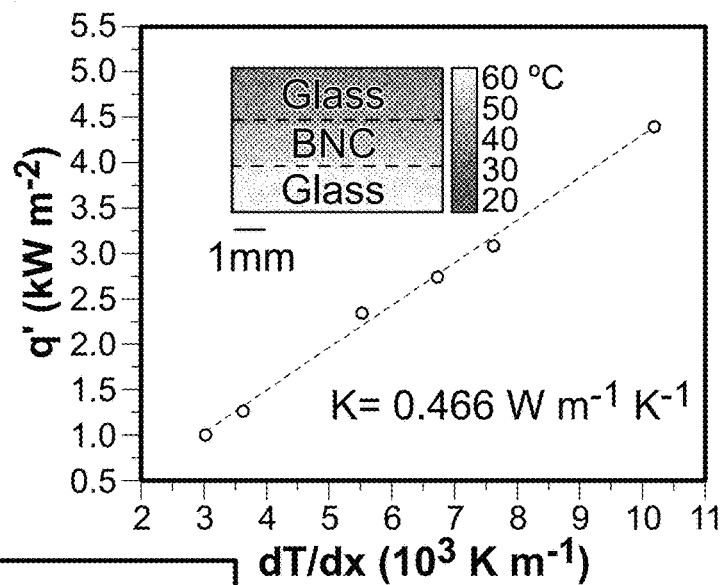
FIG. 3E is an exemplary embodiment of the thermal conductivity of a wet BNC aerogel in accordance with the present disclosure.
Figure 3F:
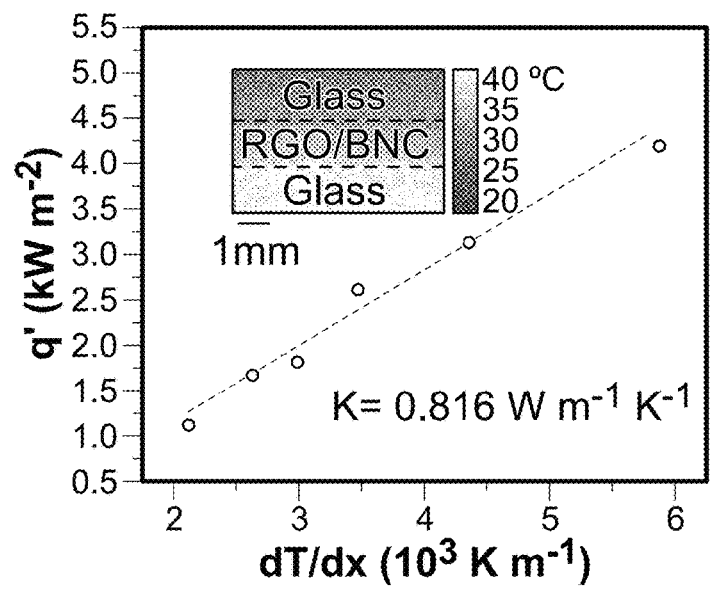
FIG. 3F is an exemplary embodiment of a wet RGO/BNC aerogel in accordance with the present disclosure. The insets in FIGS. 3E and 3F depict IR images showing the temperature gradient along the thickness of the hydrated BNC and RGO/BNC layers.
Figure 4A:
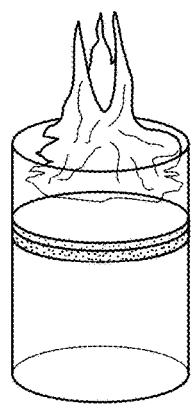
FIG. 4A is an exemplary embodiment of a schematic illustration of steam generation with an RGO/BNC:BNC biofoam in accordance with the present disclosure.
Figure 4B:
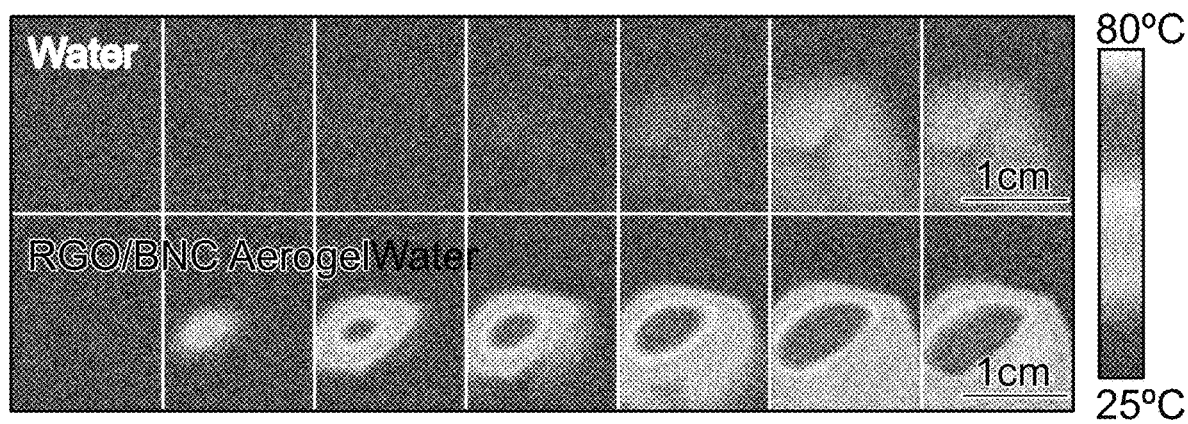
FIG. 4B is an exemplary embodiment of IR images showing the temperature of water and an RGO/BNC:BNC aerogel in accordance with the present disclosure.
Figure 4C:
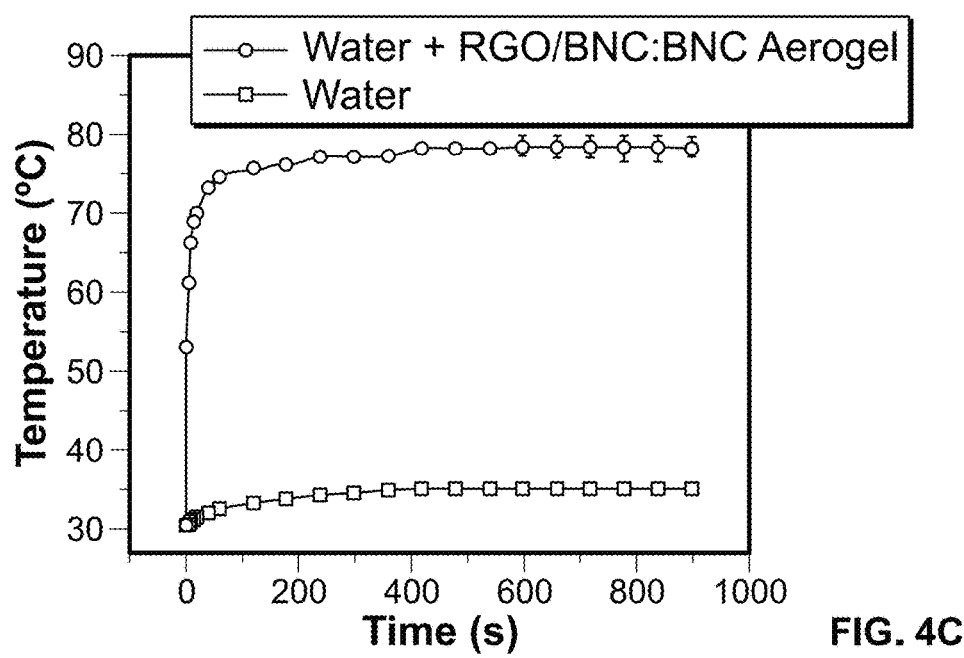
FIG. 4C is an exemplary embodiment of a plot showing the surface temperature of water and an RGO/BNC:BNC aerogel in accordance with the present disclosure.
Figure 4D:
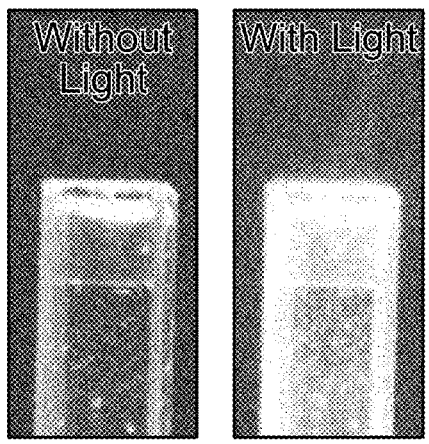
FIG. 4D is an exemplary embodiment of a photograph showing an RGO/BNC:BNC aerogel and steam generation under simulated solar illumination in accordance with the present disclosure.
Figure 4E:
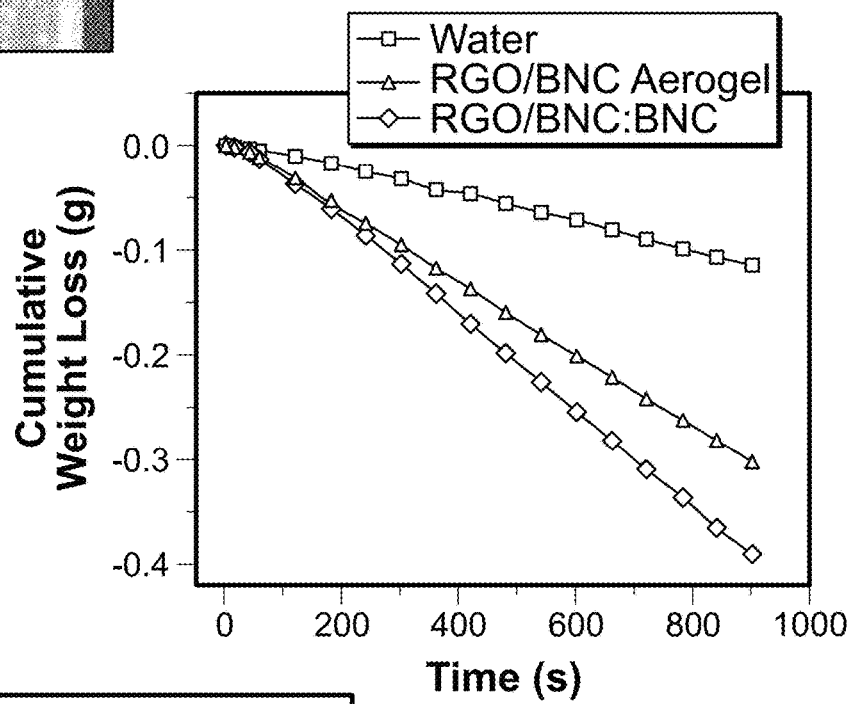
FIG. 4E is an exemplary embodiment of a plot showing the cumulative weight loss through water evaporation under solar illumination as a function of irradiation time in accordance with the present disclosure.
Figure 4F:
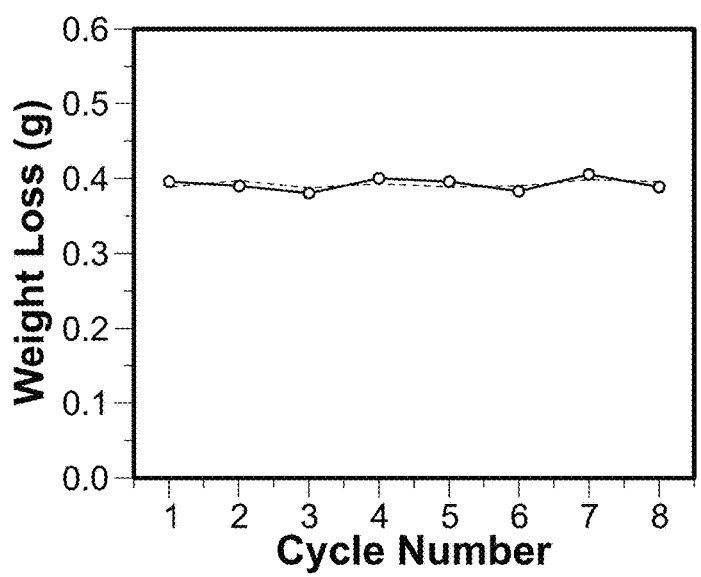
FIG. 4F is an exemplary embodiment of weight loss through water evaporation after irradiation of the RGO/BNC layer in accordance with the present disclosure.
Figure 5:
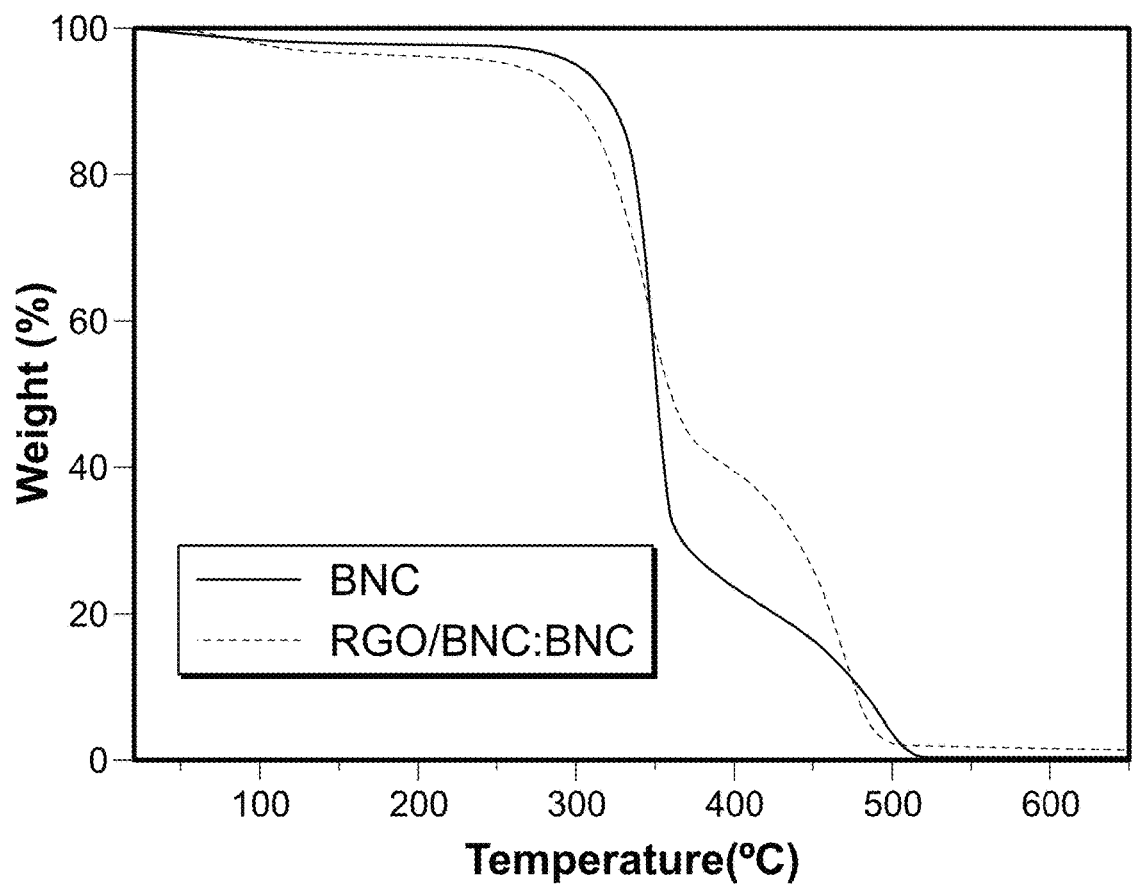
FIG. 5 is an exemplary embodiment of TGA curves for a BNC film and an air-dried RGO/BNC:BNC film in accordance with the present disclosure.
Figure 6A:
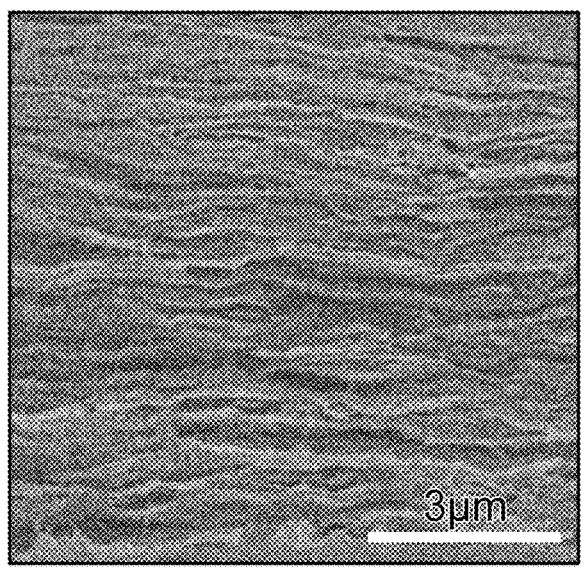
FIG. 6A is an exemplary embodiment of a cross-sectional SEM image of an air-dried RGO/BNC film in accordance with the present disclosure.
Figure 6B:
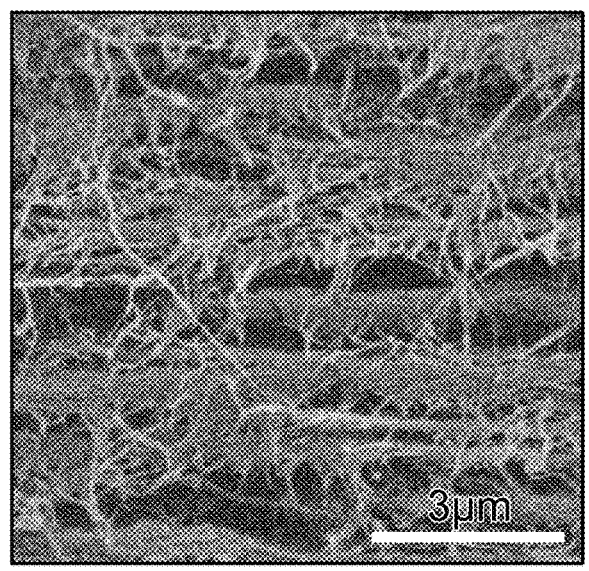
FIG. 6B is an exemplary embodiment of a cross-sectional SEM image of a BNC film in accordance with the present disclosure.
Figure 7:
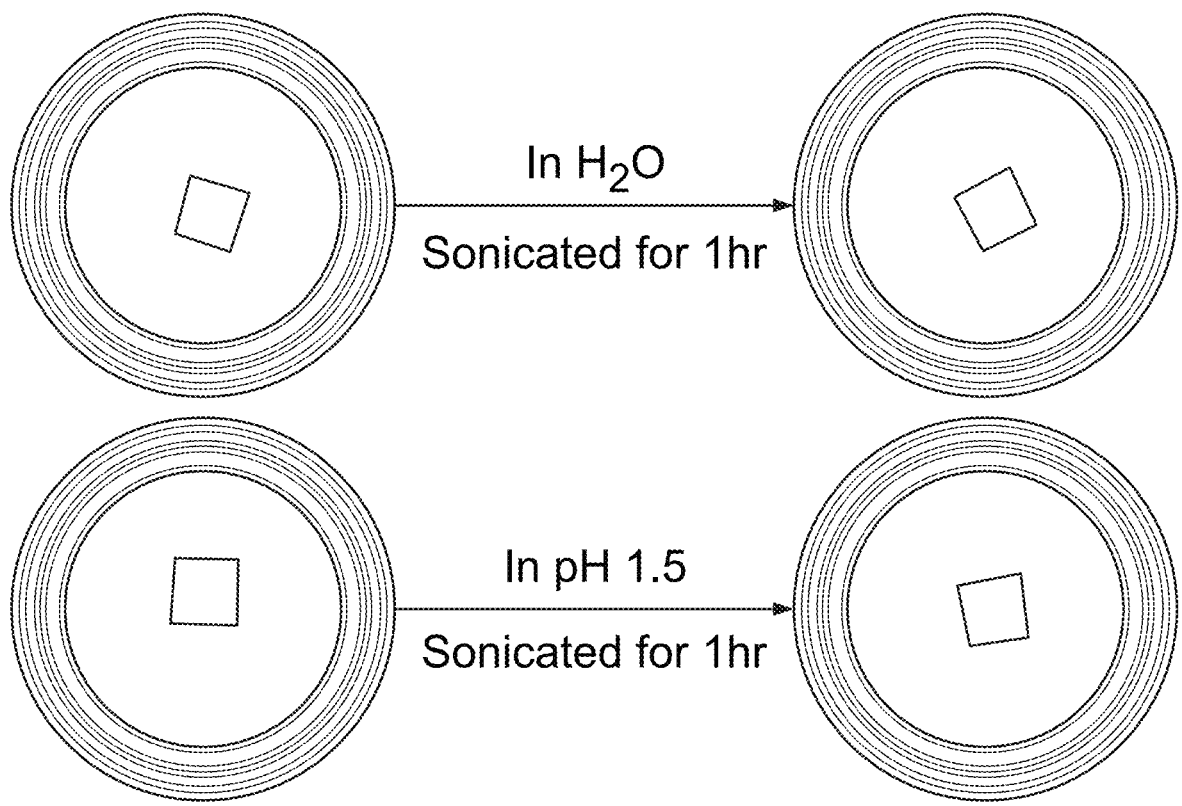
FIG. 7 is an exemplary embodiment of a photograph of the stability of an RGO/BNC:BNC film in accordance with the present disclosure.
Figure 8:
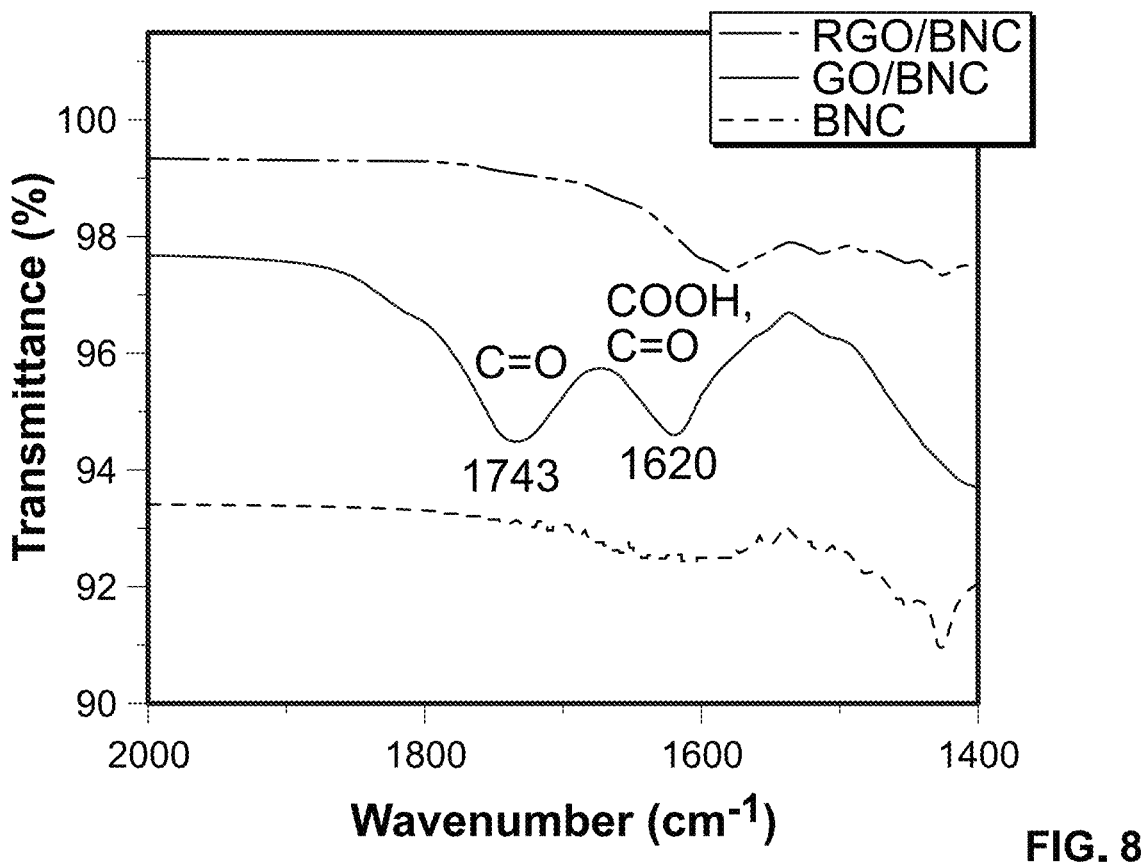
FIG. 8 is an exemplary embodiment of FTIR spectra of RGO/BNC, GO/BNC and BNC dry films in accordance with the present disclosure.
Figure 9A:
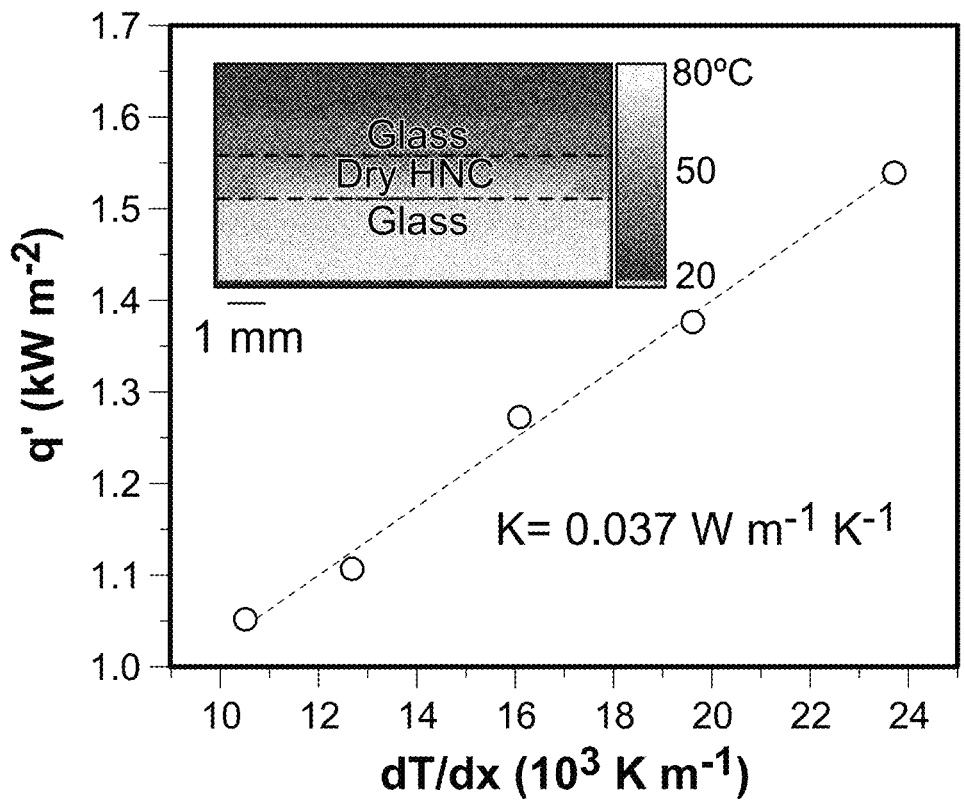
FIG. 9A is an exemplary embodiment of the thermal conductivity of a dry BNC film in accordance with the present disclosure.
Figure 9B:
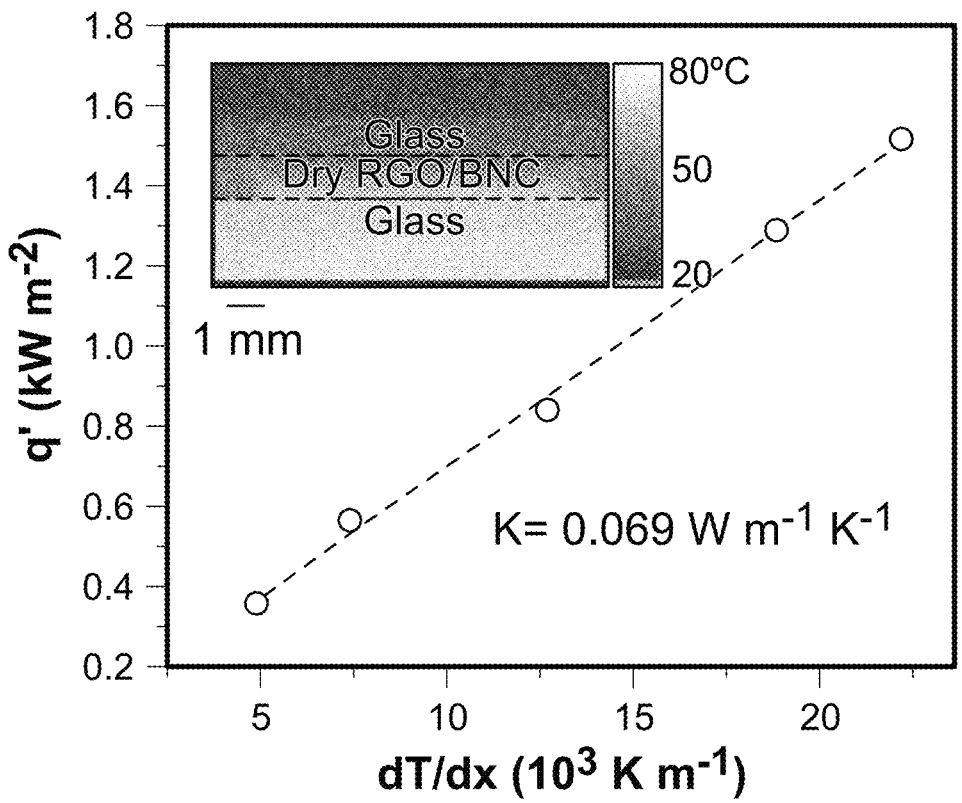
FIG. 9B is an exemplary embodiment of the thermal conductivity of an RGO/BNC foam in accordance with the present disclosure.

After harvesting the hydrogel comprising BNC and GO, the composition was subjected to a high temperature base wash to remove residual oxidative debris from the graphene oxide flakes. The composition changed from a clear brown suspension to a black aggregate confirming that chemical modification had occurred. The sample was analyzed using X-ray photoelectron spectroscopy (XPS) and Fourier Transform Infrared Spectroscopy (FTIR), and the results are shown in FIGS. 3C and 3D and FIG. 8.

Example 4: Thermal Conductivity Measurements of Wet/Dry RGO/BNC Aerogel and Bare BNC The thermal conductivities of the wet/dry RGO/BNC aerogel and the BNC aerogel were measured by sandwiching the materials between two glass microscope slides. The sandwich was placed between a hot plate and a glass slide with ice on top. The temperature distribution along the thickness was monitored using an IR camera (ICI 7320 USB camera). The emissivity coefficient of glass slide and sample to be 0.9 to obtain the temperature distribution. The Fourier equation was used to calculate the thermal conductivity of each sample:

$$q' = K \frac{\Delta T}{\Delta X}$$

Since the thermal conductivity (K) is known for glass slides (1.05 W/m·K was used), the heat flux (q') per unit area was calculated. Assuming the samples and the glass slides were experiencing the same heat flux, the thermal conductivity of the samples was calculated.

Example 5: Solar-Steam-Generation Experiment

A 1 cm×1 cm two layer aerogel with a thickness of around 21 mm was floated on water in a plastic cuvette with dimensions of 12.5 mm (W)×12.5 mm (D)×49 mm (H). The solar beam from a solar simulator (Newport AM1.5) was concentrated using a magnifying lens and illuminated onto the floating aerogel. The power density of the solar beam at the sample surface was controlled to be 10 kW/m². Each sample was illuminated for 15 min and the weight loss over the entire duration was recorded. The temperature was measured using an IR camera and the weight change from evaporation was measured using an electronic mass balance with an accuracy of 0.1 mg. The steam was generated at 100° C. under 10 kW/m² illumination. The evaporation efficiency (η) is given by:

$$\eta = \frac{mh_{LV}}{l}$$

where m is the evaporation rate, $h_{LV}$ is the total enthalpy of sensible heat (294 J/g, from 30 to 100° C. with a specific heat of 4.2 J·g/K and phase change of liquid to water (2257 J/g), and l is the incident laser power density. FIGS. 10B and 10C graph the temperature increase and the mass of water evaporated as a function of time.

Example 6. Preparation of Wood-GO Composite

Graphene oxide was synthesized using the method reported by Tour. The wood-GO composite was prepared by drop casting an aqueous GO solution (0.3 wt %) on the surface of the radially-cut wood and set aside for the GO solution to naturally dry.

Material Characterization

Scanning electron microscopy (SEM) images were obtained on a FEI Nova NanoSEM 2300 at an acceleration voltage of 10 kV. AFM images were obtained using Dimension 3000 (Bruker Inc.) in light tapping mode. The Raman spectra were obtained using a Renishaw inVia confocal Raman spectrometer mounted on a Leica microscope with a 50× objective and a 514 nm wavelength laser as an excitation source. Absorption spectra were collected using a Shimadzu UV-1800 UV-VIS spectrophotometer. XPS spectra were obtained using a Physical Electronics 5000 VersaProbe II Scanning ESCA (XPS) Microprobe.

Thermal Conductivity Measurements

The thermal conductivity of wood in the dry and wet state was measured by sandwiching the wood between two glass slides. The sandwich structure was placed on a hot plate with ice on the top side of glass. The temperature distribution along the cross-section of the sandwich structure was monitored using an IR camera (ICI 7320 P-Series). The Fourier equation was used to calculate the thermal conductivity using Equation (1):

$$q' = K \frac{\Delta T}{\Delta X} \quad \text{Equation (1)}$$

where q' is heat flux per unit area, K is thermal conductivity of glass (1.05 W/m·K), ΔT is temperature difference, ΔX is distance difference. The calculation of thermal conductivity was based on the assumptions that the sample and the glass slides were experiencing the same heat flux, and the emissivity coefficient of sample and glass slide was 0.9.

Example 7. Steam Generation Measurements

The temperature change and weight loss from evaporation of water for wood-GO, wood and water were measured under the irradiation of 808 nm laser at a power density of 5 kW/m² or simulated solar illumination (Newport AM1.5) at a power density of 12 kW/m². In the case of solar illumination, the solar beam was concentrated using a magnifying lens and illuminated onto the surface of floating sample. The temperature was measured using an IR camera and the weight loss from evaporation was measurement using an electronic microbalance with an accuracy of 0.0001 g. A 1 cm×1 cm GO-coated wood with a thickness of 3 mm was floated on the surface of water in a plastic cuvette with dimensions of 12.5 mm (W)×12.5 mm (D)×45 mm (H). The evaporation efficiency was calculated as described herein.

Example 8. Preparation of a PDA/BNC Aerogel

*Gluconacetobacter hansenii* (ATCC®53582) was cultured in test tubes containing 16 mL of #1765 medium at 30° C. under shaking at 250 rpm. The #1765 medium is composed of 2% (w/v) glucose, 0.5% (w/v) yeast extract, 0.5% (w/v) peptone, 0.27% (w/v) disodium phosphate, and 0.5% (w/v) citric acid. Polydopamine (PDA) particles were prepared using a method reported by Lu and co-workers. To synthesize PDA particles with the size of 1 µm, ammonia solution (NH$_4$OH, 0.14 mL, 28-30%) was mixed with 31.5 mL of nanopure water (~18 MΩ·cm) and 14 mL of ethanol and the above mixture was shaken for 30 minutes. Dopamine hydrochloride solution (3.5 mL, 0.05 g/mL) was added into the above solution and then transferred to a petri dish. After 30 hours of mild shaking at room temperature, the PDA particles were collected by centrifugation (7000 rpm, 20 min) and washed with water for three times and dispersed in nanopure water (40 mL). Bacterial culture solution (3 mL, incubated 3 days) was added to #1765 medium (15 mL) to make a total 18 mL bacterial growth solution. The solution was subsequently transferred to a petri dish (diameter: 6 cm) and incubated at room temperature without disturbance. After 5 days, a thick BNC hydrogel (~4 mm) was obtained. PDA particle solution described above (40 mL) was centrifuged and dispersed in bacterial growth medium (7 mL) and was then added on top of the thick BNC hydrogel. After 12 h, PDA particles formed on the BNC hydrogel and excess medium was removed. After another 12 h, a thin layer of PDA/BNC (~100 µm) was formed on top of the prior thick BNC hydrogel. The bilayered hydrogel was then harvested and washed in boiling water for 2 hours, then dialyzed in nanopure water for one day. The purified PDA/BNC bilayer was then freeze-dried overnight. For PDA/BNC with bigger size, above procedure were simply scaled up and performed in bigger containers.

Microstructure Characterization Methods:

Scanning electron microscope (SEM) images were obtained using a FEI Nova 2300 Field Emission SEM. Transmission electron microscope (TEM) images were obtained using a JEOL JEM-2100F field emission microscopy. Dynamic light scattering (DLS) measurements were performed using Malvern Zetasizer (Nano ZS). Shimadzu UV-1800 spectrophotometer was employed for obtaining UV-vis extinction spectra and transmittance spectra. Reflectance spectra were obtained using a CRAIC micro spectrophotometer (QDI 302) coupled to a Leica optical microscope (DM 4000M) with 20× objective in the range of 450-800 nm with 10 accumulations and 100 ms exposure time in reflection mode. Raman spectra were obtained using a Renishaw inVia confocal Raman spectrometer mounted on a Leica microscope with 20× objective and 785 nm wavelength diode laser as an illumination source. Thermogravimetric analysis (TGA) was performed using TA Instruments Q5000 IR Thermogravimetric Analyzer in air (at rate of 5° C. min-1).

Thermal Conductivity Measurements of Wet/Dry PDA/BNC:

The thermal conductivities of wet/dry PDA/BNC was determined using the procedure described in Example 4 above. The emissivity coefficient of a glass slide and a sample was assumed to be 0.9 to obtain the temperature distribution.

Solar Steam Generation Experiment

A circular bilayer of PDA/BNC with 3 cm diameter and 2.1 mm thickness was floated on water in a 100-ml beaker. The solar beam from a solar simulator (Newport 66921 Arc Lamp) was directly or concentrated using a magnifying lens illuminated onto the PDA/BNC. The power density of the solar beam on the sample surface was controlled to be 1 and 3 kW/m². Each sample was illuminated for 45 min and the weight loss over the entire duration was recorded. For the cycling experiments, a 1 cm×1 cm sample with 4 mm thickness floating on water in a plastic cuvette with dimensions of 12.5 mm (W)×12.5 mm (D)×49 mm (H) was used. The power density of the solar beam at the sample surface for cycling was controlled to be 7 kW/m² (7 sun) for 15 min illumination duration. The temperature was measured using an IR camera and the weight change from evaporation was measured using an electronic mass balance with an accuracy of 0.1 mg. It is assumed that the steam was generated at 100° C. The evaporation efficiency (η) was calculated using the equation in Example 5, wherein h$_{LV}$ is the total enthalpy of sensible heat (294 J/g, from 25° C. to 100° C. with specific heat 4.2 J/g·K) and phase change of liquid to water (2256 J/g), and I is the incident illumination power density.

When introducing elements of the present disclosure or embodiments thereof, the articles "a," "an," "the," and "said" are intended to mean that there are one or more of the elements. The terms "comprising," including," and "having" are intended to be inclusive and mean that there may be additional elements other than the listed elements.

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

What is claimed is:

1. A composition comprising a bilayered structure, wherein the bilayered structure comprises bacterial nanocellulose and at least one nanomaterial in different layers.

2. The composition according to claim 1, wherein the nanomaterial is selected from the group consisting of graphene oxide, reduced graphene oxide, molybdenum disulfide, polydopamine, functionalized multiwalled carbon nanotubes and combinations thereof.

3. The composition according to claim 2, wherein the nanomaterial is selected from the group consisting of graphene oxide, reduced graphene oxide, polydopamine, and combinations thereof.

4. The composition according to claim 1, wherein the composition is biodegradable.

5. The composition according to claim 1, wherein the nanomaterial is polydopamine.

6. The composition according to claim 1, wherein the nanomaterial is selected from the group consisting of graphene oxide, reduced graphene oxide and a combination thereof.

7. A composition comprising a bilayered structure, wherein the bilayered structure comprises cellulose and at least one nanomaterial in different layers, wherein the at least one nanomaterial is selected from the group consisting of graphene oxide, reduced graphene oxide and a combination thereof.

8. The composition according to claim 7, wherein the cellulose is nanocellulose.

9. The composition according to claim 8, wherein the nanocellulose is selected from the group consisting of cellulose nanofibers, microfibrillated cellulose, nanocrystalline cellulose, bacterial nanocellulose and combinations thereof.

10. The composition according to claim 9, wherein the nanocellulose is bacterial nanocellulose.

11. The composition according to claim 7, wherein the composition is biodegradable.

* * * * *